(12) United States Patent
Matsui et al.

(10) Patent No.: US 8,748,113 B2
(45) Date of Patent: Jun. 10, 2014

(54) METHODS FOR DETECTING AND MONITORING CIRCULATING CANCER STEM CELLS

(75) Inventors: William Matsui, Baltimore, MD (US); Richard J. Jones, Baltimore, MD (US); Carol A. Huff, Ellicott City, MD (US)

(73) Assignee: The Johns Hopkins University, Baltimore, MD (US)

( * ) Notice: Subject to any disclaimer, the term of this patent is extended or adjusted under 35 U.S.C. 154(b) by 1035 days.

(21) Appl. No.: 12/743,180

(22) PCT Filed: Nov. 12, 2008

(86) PCT No.: PCT/US2008/083243
§ 371 (c)(1), (2), (4) Date: Jan. 31, 2011

(87) PCT Pub. No.: WO2009/064789
PCT Pub. Date: May 22, 2009

(65) Prior Publication Data
US 2011/0110931 A1    May 12, 2011

Related U.S. Application Data

(60) Provisional application No. 60/988,316, filed on Nov. 15, 2007, provisional application No. 61/016,958, filed on Dec. 27, 2007.

(30) Foreign Application Priority Data

Nov. 15, 2007  (WO) .................. PCT/US2007/08484

(51) Int. Cl.
*G01N 33/574* (2006.01)
*C12Q 1/32* (2006.01)

(52) U.S. Cl.
USPC ............. 435/7.23; 435/7.24; 435/26; 436/64; 436/501

(58) Field of Classification Search
None
See application file for complete search history.

(56) References Cited

U.S. PATENT DOCUMENTS

2007/0243599 A1* 10/2007 Popma ....................... 435/287.1
2008/0187938 A1*  8/2008 Wicha et al. ................... 435/7.4

FOREIGN PATENT DOCUMENTS

| WO | WO-2005/072507 |   | 8/2005 |
| WO | WO-2007/053648 |   | 5/2007 |
| WO | WO2008/030538  | * | 3/2008 |

OTHER PUBLICATIONS

Pearce et al (Stem Cells, 2005, vol. 23, pp. 752-760).*
Cheung et al (Leukemia, 2007, vol. 21, pp. 1423-1430).*
Matsui et al (Blood, 2004, vol. 103, pp. 2332-2336).*
The abstract of Jones et al (Blood, Nov. 16, 2006, vol. 108, No. 11, part 1, p. 143A).*
Al-Hajj et al., "Prospective identification of tumorigenic breast cancer cells," PNAS, 100*7):3983-3988 (2003).
Cho et al., "Recent advances in cancer stem cells," Curr Opin Genet Dev., 18(1):48-53 (2008).
Feldman et al., "Blockade of Hedgehog Signaling Inhibits Pancreatic Cancer Invasion and Metastases: A New Paradigm for Combination Therapy in Solid Cancers," Cancer Research, 67:2187-2196 (2007).
Ginestier et al., "ALDH1 is a marker of normal and malignant human mammary stem cells and a predictor of poor clinical outcome," Cell Stem Cell, 1(5):555-567 (2007).
Hermann et al., "Distinct populations of cancer stem cells determine tumor growth and metastic activity in human pancreatic cancer," Cell Stem Cell, 1(3):313-323 (2007).
Hess et al., "Selection based on CD133 and high aldehyde dehydrogenase activity isolates long-term reconstituting human hematopoietic stem cells," Blood, 107:2162-2169 (2006).
Jelski et al., "Alcohol dehydrogenase (ADH) isoenzymes and aldehyde dehydrogenase (ALDH) activity in the sera of patients with gastric cancer," Dig Dis Sci., 53(8):2101-2105 (2008).
Ponti et al., "Isolation and in vitro Propagation of Tumorigenic Breast Cancer Cells with Stem/Progenitor Cell Properties," Cancer Research, 65:5506-5511 (2005).
Woodward et al., "Cancer stem cells: markers or biomarkers?," Cancer Metastasis Rev., 27(3):459-470 (2008).
International Search Report dated Aug. 18, 2008 from PCT/US2007/084847.
International Search Report dated Jun. 29, 2009 from PCT/US2008/083243.

* cited by examiner

*Primary Examiner* — Karen Canella
(74) *Attorney, Agent, or Firm* — Foley Hoag LLP

(57) ABSTRACT

Provided herein are compositions, methods, and kits useful for detecting whether a subject has or is likely to develop a cancer and for monitoring, staging and examining a cancer patient. Also provide herein are methods for screening compounds.

8 Claims, 10 Drawing Sheets

METHODS FOR DETECTING AND MONITORING CIRCULATING CANCER STEM CELLS

STATEMENT AS TO FEDERALLY SPONSORED RESEARCH

This invention was made with the support of the United States government under Contract Numbers: NIH/NCI.K23 CA107040 by NIH/NCI, NIH/NCI.P01 CA15396 by NIH/NCI, NIH/NCI.P50 CA096888 by NIH/NCI, and NIH/NCI.K23 CA093657 by NIH/NCI. The government has certain rights in the invention.

RELATED APPLICATION

This application is a 371 U.S. National Stage of PCT/US08/083,243 filed Nov. 12, 2008, which claims priority to U.S. provisional application Ser. No. 60/988,316, filed on Nov. 15, 2007, International Application Number of PCT US2007/084847, filed on Nov. 15, 2007, and U.S. provisional application Ser. No. 60/016,958, filed on Dec. 27, 2007. All of the above-referenced applications are incorporated herein in their entirety by this reference.

BACKGROUND OF THE INVENTION

Cancer is the leading cause of death worldwide. In 2005, cancer accounted for 7.6 million (or 13% of all) deaths. Cancer stem cells have been prospectively identified in several human cancers. From a functional standpoint, these cells are highly specialized since they have the unique capacity to undergo long-term proliferation. Therefore, cancer stem cells are thought to represent the cellular component within human cancers that are ultimately responsible for growth during both initial tumor formation and disease relapse.

SUMMARY OF THE INVENTION

Provided herein are methods for detecting, isolating and identifying one or more cancer stem cells.

Provided herein are methods for determining whether a subject has, or is likely to develop a cancer, comprising determining whether the subject has circulating cells that are positive for aldehyde dehydrogenase activity (ALDH$^+$), wherein the presence of ALDH$^+$ circulating cells indicate that the subject has or is likely to develop a cancer. In some embodiments, the determining step comprises the steps of: (a) obtaining a sample from the patient; (b) isolating a predetermined population of cells from the sample, e.g., using at least one of flow cytometry, fluorescence activated cell sorting, antibody-dependent depletion, antibody-dependent solid phase capture, panning, affinity column separation and magnetic selection; and (c) determining whether the isolated cells are ALDH$^+$. In certain embodiments, peripheral blood mononuclear cells (PBMCs) are first isolated. In certain embodiments, the cancer is not Hodgkin's Disease. In certain embodiments, ALDH$^+$ refers to ALDH levels that are similar to those found in normal stem cells, e.g. normal hematopoietic stem cells, which are known to have high ALDH levels of activity, which levels are higher than in more differentiated cells.

Provided herein are methods of treatment of cancer in a subject, comprising administering to a subject in need thereof a therapeutically effective amount of an agent that is cytostatic or cytotoxic to a cancer stem cell such as an agent that targets cell surface molecules of cancer stem cells, e.g., a hematopoietic cancer stem cell.

Provided herein are methods for detecting a cancer in a patient comprising the steps of: (a) obtaining a blood sample from the patient; (b) isolating a predetermined population of cells from the blood sample, e.g., using at least one of flow cytometry, fluorescence activated cell sorting, antibody-dependent depletion, antibody-dependent solid phase capture, panning, affinity column separation and magnetic selection; and (c) determining whether the predetermined population of cells are ALDH$^+$.

Provided herein are methods for detecting a cancer other than multiple myeloma in a patient comprising the steps of: (a) obtaining a blood sample from the patient; (b) isolating a predetermined population of cells from the blood sample, e.g., using at least one of flow cytometry, fluorescence activated cell sorting, antibody-dependent depletion, antibody-dependent solid phase capture, panning, affinity column separation and magnetic selection; and (c) determining whether the isolated cells are ALDH$^+$.

In some embodiments, the sample is from the patient's blood. In some embodiments, the sample is from the patient's bone marrow. In yet other embodiments the sample is from umbilical cord blood, placenta, spleen, lymphnodes or liver.

Provided herein are methods for monitoring the effectiveness of a cancer treatment in a patient comprising the steps of: (a) obtaining a blood sample from the patient; (b) isolating a predetermined population of cells from the blood sample, e.g., using at least one of flow cytometry, fluorescence activated cell sorting, antibody-dependent depletion, antibody-dependent solid phase capture, panning, affinity column separation and magnetic selection; (c) determining whether the isolated cells are ALDH$^+$; and (d) comparing the number of ALDH$^+$ cells with the number of ALDH$^+$ cells determined at an earlier time point, either prior to or after initiation of the cancer treatment.

Provided herein are assays for determining the efficacy of a compound for treating a cancer comprising the steps of: (a) obtaining a blood sample from the patient; (b) isolating a predetermined population of cells from the blood sample, e.g., using at least one of flow cytometry, fluorescence activated cell sorting, antibody-dependent depletion, antibody-dependent solid phase capture, panning, affinity column separation and magnetic selection; and (c) determining whether the isolated cells are ALDH$^+$; thereby determining the efficacy of said compound for treating the cancer.

Provided herein are methods for staging a patient diagnosed with a cancer comprising the steps of: (a) obtaining a blood sample from the patient; (b) isolating a predetermined population of cells from the blood sample, e.g., using at least one of flow cytometry, fluorescence activated cell sorting, antibody-dependent depletion, antibody-dependent solid phase capture, panning, affinity column separation and magnetic selection; and (c) determining the number of undifferentiated cancer cells present in the isolated population of cells; thereby staging the patient. In some embodiments, the method further comprises the step of (d) comparing the number of stem cells present in the isolated population to a predetermined level of stem cells, wherein the predetermined level indicates the extent or severity of cancer in a patient. In some embodiments, the determining step is performed using flow cytometry. In various embodiments the number of isolated stem cells is between 5-50,000 per ml of blood.

Provided herein are methods for monitoring the presence of a cancer in a patient comprising the steps of: (a) obtaining a blood sample from the patient; (b) isolating a predetermined population of cells from the blood sample, e.g., using at least one of flow cytometry, fluorescence activated cell sorting, antibody-dependent depletion, antibody-dependent solid phase capture, panning, affinity column separation and magnetic selection; (c) determining the number of undifferentiated cancer cells present in the isolated population of cells; (d) repeating steps (a) through (c) at least one time; and (e) comparing the results.

Provided herein are methods for identifying a sub-population of undifferentiated cancer cells in a cell sample comprising the steps of: (a) obtaining a blood sample from the patient; (b) isolating a predetermined population of cells from the blood sample, e.g., using at least one of flow cytometry, fluorescence activated cell sorting, antibody-dependent depletion, antibody-dependent solid phase capture, panning, affinity column separation and magnetic selection; and (c) determining which cells in the isolated predetermined population are ALDH$^+$, thereby identifying a sub-population of undifferentiated cancer cells in said cell sample.

Provided herein are methods for monitoring whether or not a cancer treatment is effective, e.g., against a cancer cell, a cancer stem cell and/or a normal cancer cell. In some embodiments, the determining step comprises the steps of: (a) obtaining a sample from the patient; (b) isolating a predetermined population of cells from the sample, e.g., using at least one of flow cytometry, fluorescence activated cell sorting, antibody-dependent depletion, antibody-dependent solid phase capture, panning, affinity column separation and magnetic selection; and (c) determining whether the isolated cells are ALDH$^+$.

Provided herein are isolated predetermined populations of hematopoietic cells, wherein the cell population is defined by a specific set of cell surface markers in addition to the relative level of ALDH activity.

Provided herein are isolated predetermined populations of hematopoietic cells, wherein the cell population is defined by a specific set of cell surface markers in addition to the relative level of ALDH protein.

Cell populations that express very low levels (near background) or undetectable levels of a cell-surface marker are herein indicated by a superscripted (−) symbol following the name of the cell-surface molecule. Cell populations that express levels of a cell-surface marker that are significantly above background, are herein indicated by a superscripted (+) symbol following the name of the cell-surface molecule.

Provided herein are isolated subpopulations of circulating cells wherein the cells are CD138$^-$ (syndecan-1)$^-$ and ALDH$^+$.

Provided herein are isolated subpopulations of circulating cells, wherein the cells are ALDH$^+$ and CD15$^-$ (also known as 3-fucosyl-N-acetyl-lactosamine, FCT3A, ELFT, stage specific embryonic antigen 1, SSEA-1, Lewis x, & LeX).

Provided herein are methods for detecting minimum residual disease in a cancer patient comprising the steps of: (a) obtaining a blood sample from the patient; (b) isolating a predetermined population of cells from the blood sample, e.g., using at least one of flow cytometry, fluorescence activated cell sorting, antibody-dependent depletion, antibody-dependent solid phase capture, panning, affinity column separation and magnetic selection; and (c) determining whether the isolated cells are ALDH; thereby detecting minimum residual disease in the patient.

Provided herein are methods to select a cancer patient who is predicted to benefit from the administration of a chemotherapeutic comprising the steps of: (a) obtaining a blood sample from the patient; (b) isolating a predetermined population of cells from the blood sample, e.g., using at least one of flow cytometry, fluorescence activated cell sorting, antibody-dependent depletion, antibody-dependent solid phase capture, panning, affinity column separation and magnetic selection; and (c) determining whether the isolated cells are ALDH$^+$; wherein the patient is predicted to benefit from the administration of a chemotherapeutic when the isolated cells are ALDH$^+$.

Provided herein are methods of treating cancer in a patient wherein at least one circulating cancer stem cell has been identified comprising the steps of: (a) detecting a circulating cancer stem cell; (b) identifying the cancer; and (c) contacting the circulating cancer stem cell with a therapeutically effective amount of a chemotherapeutic; wherein the patient is predicted to benefit from the administration of a chemotherapeutic when the isolated cells are ALDH$^+$.

Provided herein are kits for detecting or isolating cancer stem cells, comprising one or more reagents for detecting one or more of the following biomarkers: ALDH, CD34 (Hematopoietic progenitor cell antigen CD34 precursor), CD38 (also known as acute lymphoblastic leukemia cell antigen CD38, ADP-ribosyl cyclase 1, cADPr hydrolase 1, Cyclic ADP-ribose hydrolase 1, Lymphocyte differentiation antigen CD38 & T10), CD19 (B4, B-lymphocyte antigen CD19 precursor, B-lymphocyte surface antigen B4, Differentiation antigen CD19, Leu-12, MGC12802), CD20 (B1, B-lymphocyte antigen CD20, B-lymphocyte surface antigen B1, Bp35, Leu-16, LEU-16, MGC3969, MS4A1, MS4A2, S7), CD27 (CD27L receptor, MGC20393, S152, T14, T-cell activation antigen CD27, Tp55, Tumor necrosis factor receptor superfamily member 7 precursor, TNFRSF7), CD15, CD30 (CD30L receptor, D1S166E, KI-1, KI-1 antigen, Lymphocyte activation antigen CD30, Tumor necrosis factor receptor superfamily member 8 precursor, TNFRSF8), CD52 (Cambridge pathology 1 antigen, CAMPATH-1 antigen precursor, CD52 antigen, CDw52, CDW52, Epididymal secretory protein E5, HE5) and CD138. In some embodiments, the cancer stem cells are circulating cancer stem cells. In some embodiments, the cancer stem cells are from bone marrow.

Provided herein are compositions for detecting or isolating cancer stem cells, comprising one or more agents that specifically bind to one or more of the following biomarkers: ALDH, CD34, CD38, CD19, CD20, CD27, CD15, CD30, CD52 and CD138.

Provided herein are methods for identifying an agent that is cytostatic or cytotoxic toward a cancer stem cell, comprising contacting an isolated cancer stem cell with a test agent and determining whether the test agent inhibits the proliferation of or is toxic to the cancer stem cell, wherein the isolated cancer stem cell is ALDH$^+$. In some embodiments the isolated cancer stem cells are CD34$^-$ and CD138$^-$. In some embodiments (e.g., in certain embodiments of leukemia), the isolated cancer stem cells are CD34$^+$ and CD38$^-$. In some embodiments, the isolated cancer stem cells are CD19$^+$, CD20$^+$, CD27$^+$, CD15$^-$ and CD30$^-$. In some embodiments, the isolated cancer stem cells are CD138$^-$, CD27$^+$, CD19$^+$ and CD20$^+$. In some embodiments, the isolated cancer stem cells are CD19$^+$ and CD20$^+$. In some embodiments, the isolated cancer stem cells are CD52$^+$. In some embodiments, the isolated cancer stem cells are ALDH$^+$ and positive for one or more of the above-referenced markers, in particular one of the combinations of markers.

Provided herein are methods of treatment of cancer in a subject, comprising administering to a subject in need thereof a therapeutically effective amount of a first agent that is cytostatic or cytotoxic to a cancer stem cell and a therapeutically effective amount of a second agent that decreases tumor burden. In some embodiments, the first agent and the second agent are different. The first agent may be any agent that targets cell surface molecules of cancer stem cells, e.g., a hematopoietic cancer stem cell. In certain embodiments of such treatment methods, the first agent is a monoclonal antibody specific for CD20, e.g., rituximab. In certain embodiments of such treatment methods, the first agent is a monoclonal antibody specific for CD52, e.g., alemtuzumab. The second agent may be any agent that is known for reducing the tumor mass of a cancer, e.g., a B cell malignancy. Such treatment not only includes chemotherapy, but also radiation therapy and anti-angiogenic therapy among others.

In some embodiments of the compositions, methods and kits provided herein, the cancer treatment is a stem-cell targeted therapy. In some embodiments, the cancer treatment involves induction of terminal differentiation. In some embodiments, the cancer treatment involves inhibition of telomerase. In some embodiments, the cancer treatment involves inhibition of developmental signaling pathways. In some embodiments, the cancer treatment involves inhibition of intracellular signal transduction pathways. In some embodiments, the cancer treatment involves induction of active immunity to cellular antigens. In some embodiments, the cancer treatment involves induction of passive immunity to cellular antigens.

In some embodiments of the compositions, methods and kits provided herein, the cancer treatment is for leukemia and the isolated cells are CD34$^+$ and CD38$^-$.

In some embodiments of the compositions, methods and kits provided herein, the cancer treatment is for Hodgkin's Lymphoma and the isolated cells are CD19$^+$, CD20$^+$, CD27$^+$, CD15$^-$ and CD30$^-$.

In some embodiments of the compositions, methods and kits provided herein, the cancer treatment is for Multiple Myeloma and the isolated cells are CD138$^-$, CD27$^+$, CD19$^+$ and CD20$^+$.

In some embodiments of the compositions, methods and kits provided herein, the cancer treatment is for Multiple Myeloma and the isolated cells are CD138$^-$, CD34$^-$, CD27$^+$, CD19$^+$ and CD20$^+$.

In some embodiments of the compositions, methods and kits provided herein, the cancer treatment is for Multiple Myeloma and the isolated cells are CD138$^-$, CD34$^-$, CD27$^+$, CD19$^+$, CD20$^+$ and CD52$^+$.

In some embodiments of the compositions, methods and kits provided herein, the cancer treatment is for Non Hodgkin's Lymphoma and the isolated cells are CD19 'and CD20'.

In some embodiments of the compositions, methods and kits provided herein, the cancer treatment is for Leukemia and the isolated cells are CD34$^+$ and CD38$^-$.

In some embodiments of the compositions, methods and kits provided herein, the circulating cells are derived from a patient with cancer. In some embodiments, the circulating cells are isolated from a patient with cancer.

In some embodiments of the compositions, methods and kits provided herein, the chemotherapeutic is a stem-cell targeted therapy. In some embodiments, the chemotherapeutic induces terminal differentiation. In some embodiments, the chemotherapeutic inhibits telomerase. In some embodiments, the chemotherapeutic inhibits at least one developmental signaling pathway. In some embodiments, the chemotherapeutic inhibits at least one intracellular signal transduction pathway. In some embodiments, the chemotherapeutic induces passive immunity to cellular antigens. In some embodiments, the chemotherapeutic induces active immunity to cellular antigens. In some embodiments, the chemotherapeutic is a hedgehog inhibitor. In some embodiments, the chemotherapeutic is a telomerase inhibitor. In some embodiment, the chemotherapeutic is a cytotoxic agent, an antiproliferative, a targeting agent or a biologic agent. In some embodiments, the targeting agent is a kinase inhibitor or a cell cycle regulator. In some embodiments, the biologic agent is a cytokine, vaccine, viral agent or immunostimulant. In some embodiments, the chemotherapeutic is an HDAC inhibitor. In certain embodiments the chemotherapeutic is rituximab or alemtuzumab.

In some embodiments of the compositions, methods and kits provided herein, the isolated cells are CD138$^-$. In some embodiments, the isolated cells are CD20. In some embodiments, the isolated cells are CD19$^+$. In some embodiments, the isolated cells are CD27. In some embodiments, the isolated cells are Hoechst$^-$. In some embodiments, the isolated cells are CD15. In some embodiments, the isolated cells are CD30$^-$. In some embodiments (e.g., in certain embodiments of leukemia), the isolated cells are CD34$^+$. In other embodiments (e.g., in certain embodiments of multiple myeloma), the isolated cells are CD34$^-$.

In some embodiments of the compositions, methods and kits provided herein, the isolated cells have relatively higher levels of ALDH activity compared to the mature tumor cells. In some embodiments, these cells have a high level of Aldehyde Dehydrogenase (ALDH high), e.g., relative to the level of ALHD in corresponding normal cells, such as in normal stem cells (e.g., normal hematological stem cells). "High" includes differences of at least about 25%, 50%, 2 fold, 5 fold, 10 fold, or any statistically significant difference. "ALDH high" may be high ALDH protein or activity levels.

In some embodiments of the methods described herein, the method comprises two or more depletion steps.

In some embodiments of the compositions, methods and kits provided herein, the biomarker comprises ALDH.

In some embodiments of the kits provided herein, the kit is for identifying leukemia and the biomarkers are ALDH, CD34 and CD38. In some embodiments, the kit is for identifying Hodgkin's Lymphoma and the biomarkers are ALDH, CD19, CD20, CD27, CD15 and CD30. In some embodiments, the kit is for identifying Multiple Myeloma and the biomarkers are ALDH, CD138, CD27, CD19 and CD20. In some embodiments, the kit is for identifying Non Hodgkin's Lymphoma and the biomarkers are ALDH, CD19 and CD20.

In some embodiments of the compositions, methods and kits provided herein, the cancer is a hematological cancer, such as a B-cell malignancy. In some embodiments, the cancer is a hematological cancer, such as a B-cell, respectfully, with the proviso that the disease is not Hodgkin's lymphoma. In certain embodiments, e.g., in which a bone marrow cell is detected and/or isolated, the cancer is a hematological cancer, such as a B-cell, with the proviso that the disease is not multiple myeloma.

INCORPORATION BY REFERENCE

All publications and patent applications mentioned in this specification are herein incorporated by reference to the same extent as if each individual publication or patent application was specifically and individually indicated to be incorporated by reference. In case of conflict, the definitions and information provided in this application govern.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

DETAILED DESCRIPTION OF THE INVENTION

Figure 1:
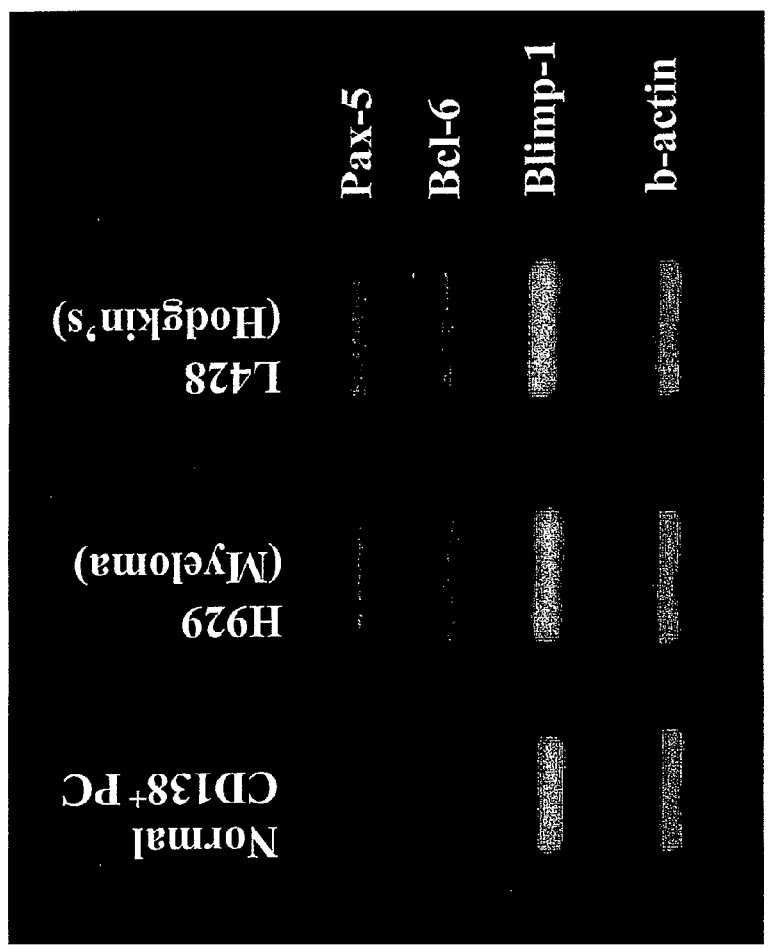
FIG. 1 is an image of an electrophoresis gel showing that Reed-Sternberg (Hodgkin's Lymphoma) cell lines H929 and L428 have similar expression patterns to normal and myeloma plasma cells.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

Despite their erroneous growth potential, cancer stem cells in most diseases have been difficult to study because they are rare and account for as few as 1 in 10,000 to 100,000 total cancer cells. This rarity has important implications for the clinical evaluation of therapeutic strategies designed to target cancer stem cells, in particular circulating cancer stem cells. Specifically, effective strategies that target and inhibit cancer stem cells are not likely to produce immediate clinical responses using standard response criteria since these parameters largely measure tumor bulk.

Described herein are methods to detect, analyze and/or quantify rare circulating cancer stem cells within the peripheral blood. Such methods can be used to monitor cancer stem cells in patients undergoing treatment and for relapse of disease. In addition, such methods can be useful for monitoring cancer stem cell targeted therapies, and can be used to help predict long-term clinical outcomes.

Certain Terminology

Unless defined otherwise, all technical and scientific terms used herein have the same meaning as is commonly understood by one of skill in the art to which the claimed subject matter belongs. In the event that there is a plurality of definitions for terms herein, those in this section prevail.

It is to be understood that the foregoing general description and the following detailed description are exemplary and explanatory only and are not restrictive of any subject matter claimed. In this application, the use of the singular includes the plural unless specifically stated otherwise. It must be noted that, as used in the specification and the appended claims, the singular forms "a", "an" and "the" include plural referents unless the context clearly dictates otherwise. It should also be noted that use of "or" means "and/or" unless stated otherwise. Furthermore, use of the term "including" as well as other forms, such as "include", "includes", and "included" is not limiting.

The term "cancer stem cell" as used herein refers to cells that are precursors to mature cancer cells. In certain embodiments, mature cancer cells do not proliferate. In some embodiments, the cancer stem cells are resistant to cancer therapy that is effective for the mature cancer cells. In some embodiments, these cells have a high level of Aldehyde Dehydrogenase (ALDH$^{high}$). In some embodiments, the cells are ALDH positive (ALDH$^+$). In some embodiments (e.g., in certain embodiments of multiple myeloma), the cancer stem cells are CD138⁻ and the mature cancer cells are CD138⁺. In some embodiments (e.g., in certain embodiments of Hodgkin's lymphoma), the cancer stem cells are CD15⁻ and the mature cancer cells are CD15⁺. In some embodiments (e.g., in certain embodiments of Hodgkin's lymphoma), the cancer stem cells are CD30⁻ and the mature cancer cells are CD30⁺. In some embodiments (e.g., in certain embodiments of Hodgkin's lymphoma and multiple myeloma), the cancer stem cells are CD19⁺. In some embodiments (e.g., in certain embodiments of Hodgkin's lymphoma and multiple myeloma), the cancer stem cells are CD20⁺. In some embodiments (e.g., in certain embodiments of Hodgkin's lymphoma and multiple myeloma), the cancer stem cells are CD27⁺. In some embodiments (e.g., in certain embodiments of Hodgkin's lymphoma and multiple myeloma), the cancer stem cells are CD52⁺. In some embodiments (e.g., in certain embodiments of leukemia), the cancer stem cells are CD34⁺. In some embodiments (e.g., in certain embodiments of leukemia), the cancer stem cells are CD38⁻.

As used herein the verb "isolate", as used in the context of "isolating a predetermined population of cells", may be used interchangably with the verbs select, purify, enrich and identify.

The term "antibody" as used herein refers to antibody fragments, Fab fragments, antibody conjugates, single-chain antibodies, antiserum, serum, immunoglobulin, monoclonal antibodies, polyclonal antibodies, antigen or epitope-specific binding fragments, CDR fragments and any of the above as obtained from any species including a virus or phage, provided that these bind specifically to an antigen. It is understood that antibody, as defined by all of the above terms, may include chimeras from different species or antibodies for fragments thereof that are modified, isotype switched, conjugated, coupled, chemically synthesized or derived from phage display technology, provided that these bind specifically to an antigen.

The term "subject", "patient" or "individual" as used herein in reference to individuals suffering from a disorder, and the like, encompasses mammals and non-mammals. Examples of mammals include, but are not limited to, any member of the Mammalian class: humans, non-human primates such as chimpanzees, and other apes and monkey species; farm animals such as cattle, horses, sheep, goats, swine; domestic animals such as rabbits, dogs, and cats; laboratory animals including rodents, such as rats, mice and guinea pigs, and the like. Examples of non-mammals include, but are not limited to, birds, fish and the like. In one embodiment of the methods and compositions provided herein, the mammal is a human.

The terms "treat," "treating" or "treatment," and other grammatical equivalents as used herein, include alleviating, abating or ameliorating a disease or condition symptoms, ameliorating the underlying metabolic causes of symptoms, inhibiting the disease or condition, e.g., arresting the development of the disease or condition, relieving the disease or condition, causing regression of the disease or condition, relieving a condition caused by the disease or condition, or stopping the symptoms of the disease or condition. The terms further include achieving a therapeutic benefit. By therapeutic benefit is meant eradication or amelioration of the underlying disorder being treated. Also, a therapeutic benefit is achieved with the eradication or amelioration of one or more of the physiological symptoms associated with the underlying disorder such that an improvement is observed in the patient, notwithstanding that the patient may still be afflicted with the underlying disorder.

The terms "prevent," "preventing" or "prevention," and other grammatical equivalents as used herein, include preventing additional symptoms, preventing the underlying metabolic causes of symptoms, inhibiting the disease or condition, e.g., arresting the development of the disease or condition and are intended to include prophylaxis. The terms further include achieving a prophylactic benefit. For prophylactic benefit, the compositions may be administered to a patient at risk of developing a particular disease, or to a patient reporting one or more of the physiological symptoms of a disease, even though a diagnosis of this disease may not have been made.

Where combination treatments are contemplated, it is not intended that the agents described herein be limited by the particular nature of the combination. For example, the agents described herein may be administered in combination as simple mixtures as well as chemical hybrids. An example of the latter is where the agent is covalently linked to a targeting carrier or to an active pharmaceutical. Covalent binding can be accomplished in many ways, such as, though not limited to, the use of a commercially available cross-linking agent.

As used herein, the terms "pharmaceutical combination", "administering an additional therapy", "administering an additional therapeutic agent" and the like refer to a pharmaceutical therapy resulting from the mixing or combining of more than one active ingredient and includes both fixed and non-fixed combinations of the active ingredients. The term "fixed combination" means that at least one of the agents described herein, and at least one co-agent, are both administered to a patient simultaneously in the form of a single entity or dosage. The term "non-fixed combination" means that at least one of the agents described herein, and at least one co-agent, are administered to a patient as separate entities either simultaneously, concurrently or sequentially with variable intervening time limits, wherein such administration provides effective levels of the two or more agents in the body of the patient. These also apply to cocktail therapies, e.g. the administration of three or more active ingredients.

As used herein, the terms "co-administration", "administered in combination with" and their grammatical equivalents or the like are meant to encompass administration of the selected therapeutic agents to a single patient, and are intended to include treatment regimens in which the agents are administered by the same or different route of administration or at the same or different times. In some embodiments the agents described herein will be co-administered with other agents. These terms encompass administration of two or more agents to an animal so that both agents and/or their metabolites are present in the animal at the same time. They include simultaneous administration in separate compositions, administration at different times in separate compositions, and/or administration in a composition in which both agents are present. Thus, in some embodiments, the agents described herein and the other agent(s) are administered in a single composition. In some embodiments, the agents described herein and the other agent(s) are admixed in the composition.

The terms "effective amount", "therapeutically effective amount" or "pharmaceutically effective amount" as used herein, refer to a sufficient amount of at least one agent being administered which will relieve to some extent one or more of the symptoms of the disease or condition being treated. The result can be reduction and/or alleviation of the signs, symptoms, or causes of a disease, or any other desired alteration of a biological system. For example, an "effective amount" for therapeutic uses is the amount of the composition comprising an agent as set forth herein required to provide a clinically significant decrease in a disease. An appropriate "effective" amount in any individual case may be determined using techniques, such as a dose escalation study.

The terms "administer," "administering", "administration," and the like, as used herein, refer to the methods that may be used to enable delivery of agents or compositions to the desired site of biological action. These methods include, but are not limited to, oral routes, intraduodenal routes, parenteral injection (including intravenous, subcutaneous, intraperitoneal, intramuscular, intravascular or infusion), topical and rectal administration. Those of skill in the art are familiar with administration techniques that can be employed with the agents and methods described herein, e.g., as discussed in Goodman and Gilman, The Pharmacological Basis of Therapeutics, current ed.; Pergamon; and Remington's, Pharmaceutical *Sciences* (current edition), Mack Publishing Co., Easton, Pa. In certain embodiments, the agents and compositions described herein are administered orally.

The term "acceptable" as used herein, with respect to a formulation, composition or ingredient, means having no persistent detrimental effect on the general health of the subject being treated.

The term "pharmaceutically acceptable" as used herein, refers to a material, such as a carrier or diluent, which does not abrogate the biological activity or properties of the agents described herein, and is relatively nontoxic, i.e., the material may be administered to an individual without causing undesirable biological effects or interacting in a deleterious manner with any of the components of the composition in which it is contained.

The terms "enhance" or "enhancing," as used herein, means to increase or prolong either in potency or duration a desired effect. Thus, in regard to enhancing the effect of therapeutic agents, the term "enhancing" refers to the ability to increase or prolong, either in potency or duration, the effect of other therapeutic agents on a system. An "enhancing-effective amount," as used herein, refers to an amount adequate to enhance the effect of another therapeutic agent in a desired system.

As used herein, the terms "cancer treatment", "cancer therapy" and the like encompasses treatments such as surgery (such as cutting, abrading, ablating (by physical or chemical means or a combination of physical or chemical means), suturing, lasering or otherwise physically changing body tissues and organs), radiation therapy, administration of chemotherapeutic agents and combinations of any two or all of these methods. Combination treatments may occur sequentially or concurrently. Treatments(s), such as radiation therapy and/or chemotherapy, that is administered prior to surgery, is referred to as neoadjuvant therapy. Treatments(s), such as radiation therapy and/or chemotherapy, administered after surgery is referred to herein as adjuvant therapy.

Many chemotherapeutic agents are known and may operate via a wide variety of modes of action. In some nonlimiting embodiments of the present invention, the chemotherapeutic agent is a cytotoxic agent, an antiproliferative, a targeting agent (such as kinase inhibitors and cell cycle regulators), or a biologic agent (such as cytokines, vaccines, viral agents, and other immunostimulants such as BCG, hormones, monocolonal antibodies and siRNA). The nature of a combination therapy involving administration of a chemotherapeutic agent will depend upon the type of agent being used.

Methods

Described herein are methods to detect, analyze and/or quantify rare circulating cancer stem cells within the peripheral blood. Such methods can be used to monitor cancer stem cells in patients undergoing treatment and for relapse of disease. In addition, such methods can be useful for monitoring cancer stem cell targeted therapies, and can be used to help predict long-term clinical outcomes.

The methods used to detect, analyze, isolate and quantify undifferentiated cells, including circulating cancer stem cells, may involve one or at least two of the following steps:

a) Isolation of a population of undifferentiated cells using cell sorting/separation techniques such as, by way of example only, Immunomagnetic techniques, Flow Cytometric techniques, Fluorescence Activate Cell Sorting (FACS), panning, affinity column separation, or combination thereof;

b) Enrichment of at least one specific phenotype from the isolated population of undifferentiated cells using cell sorting/separtion techniques such as, by way of example only, Immunomagnetic techniques, Flow Cytometric techniques, Fluorescence Activate Cell Sorting (FACS), panning, affinity column separation, or combination thereof;

c) Determination of expression level of aldehyde dehydrogenase (ALDH);

d) Determination of drug resistance and/or drug sensitivity using efflux of compounds and/or lipophilic dyes such as Hoechst 33342 dye;

e) Determination of presence of immunoglobulin (Ig).

In certain embodiments, the methods described herein use at least three of these steps, while in other embodiments the methods use at least four of these steps. In certain embodiments, the methods described herein use all of these steps. In various embodiments the isolation and/or enrichment steps are repeated more than once before the expression level of ALDH is determined. For example, the isolation and/or enrichment steps can be repeated using the same or different techniques two times, three times, four times, five times, etc., depending on the cell-type being isolated.

Isolation of a Population of Undifferentiated Cells

Various methods and various combinations of methods may be applied to identify and isolate a predetermined population of cells including, but not limited to, a population of circulating undifferentiated cells or circulating cancer stem cells. In some embodiments, the circulating cells are circulating in the blood. Such methods include, but are not limited to, immunomagnetic techniques, flow cytometric techniques, fluorescence activated cell sorting (FACS), panning, affinity column separation, antibody-dependent depletion, antibody-dependent solid phase capture, viability selection, cell cycle selection and whole-cell ELISA (enzyme linked immunosorbent assay) or combinations thereof. For example a predetermined population of cells may be (a) isolated by depletion of CD138, CD34, CD3 and CD15 positive cells by use of marker specific antibodies and complement followed by, (b) solid phase capture with an anti-CD20 antibody and (c) subsequent detection of ALDH activity by use of a colormetric assay. It should be noted that for the purposes of this invention the verb "isolate", as used in the context of "isolating a predetermined population of cells", may be used interchangably with the verbs select, purify, enrich and identify.

Prior to using such sorting/separation techniques a blood sample can be optionally centrifuged using a density centrifugation to obtain mononuclear cells, erythrocytes and granulocytes. In certain embodiments specific cell types, including but not limited to B cells and/or T cells are obtained using density centrifugation. In certain embodiments, such density centrifugation can be achieved using a Ficoll gradient.

Immunomagnetic Isolation/Enrichment

A population of circulating undifferentiated cells, including but not limited to cancer stem cells, can be isolated from blood using immunomagnetic techniques including, but not limited to magnetic activated cell sorting (MACS). Using such techniques a bulk cell population obtained from a patient sample (e.g., a blood sample and/or a bone marrow sample) is contacted with magnetic microbeads coupled to an antibody. A population of magnetic antibody-labeled cells is magnetically separated from the bulk population by magnetic retention on a column and the unlabeled cell population passes through the column. The retained cells can then be later eluted from the column after removal of the magnet. Thus, populations of labeled and unlabeled cells can be obtained. The population of unlabeled cells has been depleted of cells specific to the particular antibody coupled to the magnetic microbeads, and is herein referred to as a first antibody negative (−) population. The later eluted population of magnetic antibody-labeled cells is enriched with cells that are specific to the particular antibody coupled to the magnetic microbeads, and is herein referred to as a first antibody positive ($^+$) population.

In certain embodiments, a second immunomagnetic separation is used to isolate a population of cells having a specific phenoytpe form the unlabeled cell population obtained from a first immunomagnetic separation. In such embodiments a second (different) antibody coupled to magnetic microbeads is added to the unlabeled cell population obtained from a first immunomagnetic separation and a population of cells that is positive for the second antibody can be separated from the unlabeled population by magnetic retention on a column. This retained population of cells is positive for the second antibody is also negative for the first antibody, and is herein referred to as a first antibody negative (−)/second antibody positive population (−/$^+$ population). The population of unlabeled cells that is not retained on the column during this second immunomagnetic separation step is depleted of cells that are positive for the first antibody and cells that are positive for the second antibody, and this second unlabeled cell population is herein referred to as a first antibody negative (−)/second antibody negative population (−/− population).

In certain embodiments, a second immunomagnetic separation is used to isolate a population of cells having a specific phenoytpe from the antibody labeled cell population obtained from a first immunomagnetic separation. In such embodiments, the first magnetic microbeads coupled with the antibody are cleaved and magnetically removed from the cells during elution from a column. The resulting unlabeled cells are then contacted with a second (different) antibody coupled to magnetic microbeads and a population of cells that is positive for the second antibody can be separated from the unlabeled population by magnetic retention on a column. This retained population of cells is positive for the second antibody, is also positive for the first antibody, and is herein referred to as a first antibody positive ($^+$)/second antibody positive population ($^+$/$^+$ population). The population of unlabeled cells that is not retained on the column during this second immunomagnetic separation step is positive for the first antibody but depleted of cells that are positive for the second antibody. This second unlabeled cell population is herein referred to as a first antibody positive ($^+$)/second antibody negative population ($^+$/−) population.

In other embodiments of the methods disclosed herein, a third immunoagnetic separation step using a third (different) antibody coupled to magnetic microbeads can be used to further isolate cells with specific cell phenotypes. In other embodiments of the methods disclosed herein, a fourth, immunoagnetic separation step using a fourth (different) antibody coupled to magnetic microbeads can be used to further isolate cells with specific cell phenotypes.

Various antibody couple magnetic microbeads can be used to deplete a bulk population and thereby yielding an enriched population. Such antibodies include, but are not limited to, CD3, CD15, CD17, CD18, CD19, CD20, CD27, CD30, CD34, CD38, CD52 and CD138. Various antibody couple magnetic microbeads can be used as the second antibody for enrichment/depletion of labeled and unlabeled fractions obtained from a first immunomagnetic separation step. Such antibodies include, but are not limited to, CD3, CD15, CD17, CD18, CD19, CD20, CD27, CD30, CD34, CD38, CD52 and CD138. Various antibody couple magnetic microbeads can be used as the third antibody for enrichment/depletion of labeled and unlabeled fractions obtained from a second immunomagnetic separation step. Such antibodies include, but are not limited to, CD3, CD15, CD17, CD18, CD19, CD20, CD27, CD30, CD34, CD38, CD52 and CD138. Various antibody couple magnetic microbeads can be used as the fourth antibody for enrichment/depletion of labeled and unlabeled fractions obtained from a third immunomagnetic separation step. Such antibodies include, but are not limited to, CD3, CD15, CD17, CD18, CD19, CD20, CD27, CD30, CD34, CD38, CD52 and CD138.

In certain embodiments of the methods disclosed herein, a population of CD138$^-$ circulating cells can be isolated from blood using such immunomagnetic techniques described herein. In such embodiments a patient sample (e.g., a blood sample and/or a bone marrow sample), optionally fractionated using density centrifugation, is labeled with CD138 antibody coupled to magnetic microbeads. The magnetic CD138 antibody-labeled cells are magnetically separated from the bulk population by magnetic retention on a column and the unlabeled population of CD138$^-$ cells passes through the column. The retained CD138 cells can then be later eluted from the column after removal from the magnet. This immunomagnetic separation step results in the isolation of a population of undifferentiated CD138$^-$ cells, including cancer stem cells that are CD138$^-$.

In other embodiments, a second antibody coupled to magnetic microbeads can be added to the unlabeled CD138$^-$ cells fraction obtained from a first magnetic separation. A second retained population of cells that is positive for the second antibody can be separated from the unlabeled population by magnetic retention on a column. This retained population is negative for CD138 but positive for the second antibody, i.e. the population is CD138$^-$/second antibody$^+$. The second non-retained, unlabeled population of cells is depleted of cells that are positive for the first antibody and depleted of cells that are positive for the second antibody. This second unlabeled population is negative for CD138 and negative for the second antibody, i.e. the population is CD138$^-$/second antibody.

In certain embodiments, a second antibody coupled to magnetic microbeads can be added to the retained CD138 labeled fraction obtained from a first magnetic separation after the CD138 labeled magnetic microbeads have been cleaved and removed from the cell population. A second retained population of cells that is positive for the second antibody can then be separated by magnetic retention on a column. This retained population is positive for CD138 and positive for the second antibody, i.e. the population is CD138$^+$/second antibody$^+$. The second non-retained CD138$^+$ population is depleted of the cells positive for the second antibody resulting in a CD138$^+$/second antibody population, i.e. the population is CD138$^+$/second antibody.

In certain embodiments of the methods disclosed herein, two immunomagnetic separations are used wherein the first separation uses CD138 antibody coupled to magnetic microbeads and the second separation uses CD3 antibody coupled to magnetic microbeads. In such embodiments populations of cells that are isolated and identified are CD138⁻/CD3⁻, CD138⁻/CD3⁺, CD138⁺/CD3⁻ and CD138⁺/CD3⁺.

In certain embodiments of the methods disclosed herein, two immunomagnetic separations are used wherein the first separation uses CD138 antibody coupled to magnetic microbeads and the second separation uses CD15 antibody coupled to magnetic microbeads. In such embodiments populations of cells that are isolated and identified are CD138⁻/CD15⁻, CD138⁻/CD15 CD138⁺/CD15⁻ and CD138⁺/CD15⁺.

In certain embodiments of the methods disclosed herein, two immunomagnetic separations are used wherein the first separation uses CD138 antibody coupled to magnetic microbeads and the second separation uses CD17 antibody coupled to magnetic microbeads. In such embodiments, populations of cells that are isolated and identified are CD138⁻/CD17⁻, CD138⁻/CD17 CD138⁺/CD17⁻ and CD138⁺/CD17⁺.

In certain embodiments of the methods disclosed herein, two immunomagnetic separations are used wherein the first separation uses CD138 antibody coupled to magnetic microbeads and the second separation uses CD18 antibody coupled to magnetic microbeads. In such embodiments populations of cells that are isolated and identified are CD138⁻/CD18⁻, CD138⁻/CD18 CD138⁺/CD18⁻ and CD138⁺/CD18⁺.

In certain embodiments of the methods disclosed herein, two immunomagnetic separations are used wherein the first separation uses CD138 antibody coupled to magnetic microbeads and the second separation uses CD19 antibody coupled to magnetic microbeads. In such embodiments, populations of cells that are isolated and identified are CD138⁻/CD19⁻, CD138⁻/CD19 CD138⁺/CD19⁻ and CD138⁺/CD19⁺.

In certain embodiments of the methods disclosed herein, two immunomagnetic separations are used wherein the first separation uses CD138 antibody coupled to magnetic microbeads and the second separation uses CD20 antibody coupled to magnetic microbeads. In such embodiments populations of cells that are isolated and identified are CD138⁻/CD20⁻, CD138⁻/CD20 CD138⁺/CD20⁻ and CD138⁺/CD20⁺.

In certain embodiments of the methods disclosed herein, two immunomagnetic separations are used wherein the first separation uses CD138 antibody coupled to magnetic microbeads and the second separation uses CD27 antibody coupled to magnetic microbeads. In such embodiments, populations of cells that are isolated and identified are CD138⁻/CD27⁻, CD138⁻/CD27 CD138⁺/CD27⁻ and CD138⁺/CD27⁺.

In certain embodiments of the methods disclosed herein, two immunomagnetic separations are used wherein the first separation uses CD138 antibody coupled to magnetic microbeads and the second separation uses CD30 antibody coupled to magnetic microbeads. In such embodiments populations of cells that are isolated and identified are CD138⁻/CD30⁻, CD138⁻/CD30 CD138⁺/CD30⁻ and CD138⁺/CD30⁺ isolated and identified are.

In certain embodiments of the methods disclosed herein, two immunomagnetic separations are used wherein the first separation uses CD138 antibody coupled to magnetic microbeads and the second separation uses CD34 antibody coupled to magnetic microbeads. In such embodiments, populations of cells that are isolated and identified are CD138⁻/CD34⁻, CD138⁻/CD34 CD138⁺/CD34⁻ and CD138⁺/CD34⁺. In certain embodiments of the methods disclosed herein, two immunomagnetic separations are used wherein the first separation uses CD38 antibody coupled to magnetic microbeads and the second separation uses CD34 antibody coupled to magnetic microbeads. In such embodiments, populations of cells that are isolated and identified are CD38⁻/CD34⁻, CD38⁻/CD34 CD38⁺/CD34⁻ and CD38⁺/CD34⁺.

Fluorescence Activated Cell Sorting (FACS)

A population of circulating undifferentiated cells, including but not limited to cancer stem cells, can be isolated from blood using flow cytometric techniques including, but not limited to Fluorescence Activated Cell Sorting (FACS). Using such techniques a bulk cell population obtained from a patient sample (e.g., a blood sample and/or a bone marrow sample) is contacted with fluorescently labeled antibody. A population of fluorescently-labeled cells is separated from the unlabeled population by cell sorting using a FACS. Thus, populations of fluorescently labeled and unlabeled cells can be obtained. The population of unlabeled cells has been depleted of cells specific to the particular fluorescently labeled antibody, and is herein referred to as a first antibody negative (−) population. The fluorescently-labeled cell population is enriched with cells that are specific to the particular fluorescently labeled antibody, and is herein referred to as a first antibody positive (⁺) population.

In certain embodiments, a second flow cytometric, including, but not limited to Fluorescence Activated Cell Sorting (FACS) separation is used to isolate a population of cells having a specific phenotype from the unlabeled cell population obtained from a first FACS separation. In such embodiments a second different antibody labeled with a different fluorescent dye is added to the unlabeled cell population obtained from a first FACS separation, and a population of cells that is positive for the second antibody can be separated from the unlabeled population by cell sorting using a FACS. The isolated population labeled with the second fluorescent dye is positive for the second antibody, but is negative for the first antibody, and is herein referred to as a first antibody negative (⁻)/second antibody positive population (⁻/⁺ population). The population of isolated unlabeled cells obtained from the secon FACS sorting step is depleted of cells that are positive for the first antibody and depleted of cells that are positive for the second antibody. This second unlabeled cell population is herein referred to as a first antibody negative (⁻)/second antibody negative population (⁻/⁻ population).

In certain embodiments, a second flow cytometric, including, but not limited to Fluorescence Activated Cell Sorting (FACS) separation is used to isolate a population of cells having a specific phenoytpe from the fluorescently-labeled cell population obtained from a FACS separation. In such embodiments, a second antibody labeled with a different fluorescent dye is added to the cell population labeled with the first fluorescent dye. The cells that are positive for the second antibody are then labeled with two fluorescent dyes and are separated from the population that is negative for the second antibody by FACS sorting. This bi-labeled population of cells is positive for the second antibody and positive for the first antibody, and is herein referred to as a first antibody positive (⁺)/second antibody positive population (⁺/⁺ population). The isolated population of cells fluorescently labelled with the first dye is positive for the first antibody but depleted of cells that are positive for the second antibody, and is herein referred to as a first antibody positive (⁺)/second antibody negative population (⁺/⁻ population).

In other embodiments of the methods disclosed herein, a third flow cytometric, including, but not limited to Fluorescence Activated Cell Sorting (FACS), separation using a third (different) antibody labeled with a third different fluorescent dye can be used to further isolate cells with specific cell phenotypes. In other embodiments of the methods disclosed herein, a fourth flow cytometric, including, but not limited to Fluorescence Activated Cell Sorting (FACS), separation using a fourth (different) antibody labeled with a fourth different fluorescent dye can be used to further isolate cells with specific cell phenotypes.

Various fluorescently labeled antibodies can be used to in the flow cytometric, including, but not limited to Fluorescence Activated Cell Sorting (FACS), separation described herein. Such antibodies include, but are not limited to, CD3, CD15, CD17, CD18, CD19, CD20, CD27, CD30, CD34, CD38, CD52 and CD138. Various fluorescently labeled antibodies can be used as the second antibody in the flow cytometric, including, but not limited to Fluorescence Activated Cell Sorting (FACS), separation described herein. Such antibodies include, but are not limited to, CD3, CD15, CD17, CD18, CD19, CD20, CD27, CD30, CD34, CD38, CD52 and CD138. Various fluorescently labeled antibodies can be used as the third antibody in the flow cytometric, including, but not limited to Fluorescence Activated Cell Sorting (FACS), separation described herein. Such antibodies include, but are not limited to, CD3, CD15, CD17, CD18, CD19, CD20, CD27, CD30, CD34, CD38, CD52 and CD138. Various fluorescently labeled antibodies can be used as the fourth antibody in the flow cytometric, including, but not limited to Fluorescence Activated Cell Sorting (FACS), separation described herein. Such antibodies include, but are not limited to, CD3, CD15, CD17, CD18, CD19, CD20, CD27, CD30, CD34, CD38, CD52 and CD138.

Various fluorescent dyes can be used to label the antibodies used in the flow cytometric methods described herein, Such fluorescent dyes include, but are not limited to, Cascade Blue, Fluorescein, Phycoerythrin, R-Phycoerythrin, CY® dyes, Cy5, Cy3, Cy7, Texas Red, RPE-Texas Red, Allophycocyanin, FITC, GFP, Bodipy dyes, TOTO dyes, TO-PRO® dyes, calcein, Alexa dyes, Fluo-3, Fluo-4, DCFH, CFSE, FMLP, PI, TOTO-1, TO-PRO®-1, TOTO-3, TO-PRO®-3, JC-1/DiOC$_2$(3), DYECYCLE™ Green, DYECYCLE™ Orange, Rhodamine 123, YO-PRO dyes, YO-PRO®-1, Propidium Iodide, SNARF® dyes, SYTOX dyes, SYTOX® Red, FURA-RED™, AmCyan, PerCp, Indo-1, Calcein Blue, DAPI, 7-AAD, Pacific Blue, ALEXA FLUOR® 405, ALEXA FLUOR® 488, ALEXA FLUOR® 546, ALEXA FLUOR® 610, RPE-ALEXA FLUOR® 610, ALEXA FLUOR® 647, ALEXA FLUOR® 700, RPE-ALEXA FLUOR® 700, ALEXA FLUOR® 750, APC-ALEXA FLUOR® 750, RPE-ALEXA FLUOR® 750, Pacific Orange, Quanum Dots, QDOT® 525 nanocrystals, QDOT® 565 nanocrystals, QDOT® 585 nanocrystals, QDOT® 605 nanocrystals, QDOT® 655 nanocrystals, QDOT® 705 nanocrystals, QDOT® 800 nanocrystals, RPE-CY®5 nanocrystals, and RPE-CY®7 nanocrystals.

In certain embodiments of the methods disclosed herein, a population of CD138$^-$ circulating cells can be isolated from blood using such flow cytometric methods described herein. In such embodiments a patient sample (e.g., a blood sample and/or a bone marrow sample), optionally fractionated using density centrifugation, is labeled with fluorescently labeled-CD138 antibody. The fluorescent-CD138 labeled cells are separated from the non-fluorescent bulk population by FACS sorting, resulting in an unlabeled population of undifferentiated CD138$^-$ cells, such as cancer stem cells, and a population of fluorescent CD138$^+$ cells.

In other embodiments, a second antibody labeled with a second fluorescent dye is added to the unlabeled CD138$^-$ cells fraction obtained from a first FACS separation. A population of cells that is positive for the second antibody can be separated from the unlabeled population by a second FACS sorting step. This second population labeled with the second fluorescent dye is negative for CD138 but positive for the second antibody, i.e. the population is CD138$^-$/second antibody. The second unlabeled population of cells is depleted of cells that are positive for the first antibody and depleted of cells that are positive for the second antibody. This second unlabeled population is negative for CD138 and negative for the second antibody, i.e. the population is CD138$^-$/second antibody.

In certain embodiments, a second antibody coupled to magnetic microbeads can be added to the fluorescently labeled CD138$^+$ fraction obtained from a first FACS separation. A population of cells that is positive for the second antibody is labeled with a first and a second fluorescent dye and can be separated form the population labeled only with the first fluorescent dye using a second FACS sorting step. This bi-labeled population is positive for CD138 and positive for the second antibody, i.e. the population is CD138$^+$/second antibody, whereas the mono-labeled CD138$^+$ population is depleted of the cells positive for the second antibody resulting in a CD138$^+$/second antibody population, i.e. the population is CD138$^+$/second antibody.

In certain embodiments of the methods disclosed herein, two FACS separations are used wherein the first separation uses CD138 antibody labeled with a first fluorescent dye and the second separation uses CD3 antibody labeled with a second fluorescent dye. In such embodiments, populations of cells that are isolated and identified are CD138$^-$/CD3$^-$, CD138$^-$/CD3$^+$, CD138$^+$/CD3$^-$ and CD138$^+$/CD3$^+$.

In certain embodiments of the methods disclosed herein, two FACS separations are used wherein the first separation uses CD138 antibody labeled with a first fluorescent dye and the second separation uses CD15 antibody labeled with a second fluorescent dye. In such embodiments populations of cells that are isolated and identified areCD138$^-$/CD15$^-$, CD138$^-$/CD15$^+$, CD138$^+$/CD15$^-$ and CD138$^+$/CD15$^+$.

In certain embodiments of the methods disclosed herein, two FACS separations are used wherein the first separation uses CD138 antibody labeled with a first fluorescent dye and the second separation uses CD17 antibody labeled with a second fluorescent dye. In such embodiments, populations of cells that are isolated and identified are CD138$^-$/CD17$^-$, CD138$^-$/CD17$^+$, CD138$^+$/CD17$^-$ and CD138$^+$/CD17$^+$.

In certain embodiments of the methods disclosed herein, two FACS separations are used wherein the first separation uses CD138 antibody labeled with a first fluorescent dye and the second separation uses CD18 antibody labeled with a second fluorescent dye. In such embodiments, populations of cells that are isolated and identified are CD138$^-$/CD18$^-$, CD138$^-$/CD18$^+$, CD138$^+$/CD18$^-$ and CD138$^+$/CD18$^+$.

In certain embodiments of the methods disclosed herein, two FACS separations are used wherein the first separation uses CD138 antibody labeled with a first fluorescent dye and the second separation uses CD19 antibody labeled with a second fluorescent dye. In such embodiments, populations of cells that are isolated and identified are CD138$^-$/CD19$^-$, CD138$^-$/CD19$^+$, CD138$^+$/CD19$^-$ and CD138$^+$/CD19$^+$.

In certain embodiments of the methods disclosed herein, two FACS separations are used wherein the first separation uses CD138 antibody labeled with a first fluorescent dye and the second separation uses CD20 antibody labeled with a second fluorescent dye. In such embodiments, populations of cells that are isolated and identified are CD138$^-$/CD20$^-$, CD138$^-$/CD20 CD138$^+$/CD20$^-$ and CD138$^+$/CD20$^+$.

In certain embodiments of the methods disclosed herein, two FACS separations are used wherein the first separation uses CD138 antibody labeled with a first fluorescent dye and the second separation uses CD27 antibody labeled with a second fluorescent dye. In such embodiments, populations of cells that are isolated and identified are CD138⁻/CD27⁻, CD138⁻/CD27 CD138⁺/CD27⁻ and CD138⁺/CD27⁺.

In certain embodiments of the methods disclosed herein, two FACS separations are used wherein the first separation uses CD138 antibody labeled with a first fluorescent dye and the second separation uses CD30 antibody labeled with a first fluorescent dye. In such embodiments, populations of cells that are isolated and identified are CD138⁻/CD30⁻, CD138⁻/CD30 CD138⁺/CD30⁻ and CD138⁺/CD30⁺.

In certain embodiments of the methods disclosed herein, two FACS separations are used wherein the first separation uses CD138 antibody labeled with a first fluorescent dye and the second separation uses CD34 antibody labeled with a first fluorescent dye. In such embodiments, populations of cells that are isolated and identified are CD138⁻/CD34⁻, CD138⁻/CD34 CD138⁺/CD34⁻ and CD138⁺/CD34⁺. In certain embodiments of the methods disclosed herein, two FACS separations are used wherein the first separation uses CD38 antibody labeled with a first fluorescent dye and the second separation uses CD34 antibody labeled with a first fluorescent dye. In such embodiments, populations of cells that are isolated and identified are CD38⁻/CD34⁻, CD38⁻/CD34 CD38⁺/CD34⁻ and CD38⁺/CD34⁺.

Various fluorescent dyes can be used to label the antibodies used such embodiments. Such fluorescent dyes include, but are not limited to, Cascade Blue, Fluorescein, Phycoerythrin, R-Phycoerythrin, CY® dyes, Cy5, Cy3, Cy7, Texas Red, RPE-Texas Red, Allophycocyanin, FITC, GFP, Bodipy dyes, TOTO dyes, TO-PRO® dyes, calcein, Alexa dyes, Fluo-3, Fluo-4, DCFH, CFSE, FMLP, PI, TOTO-1, TO-PRO®-1, TOTO-3, TO-PRO®-3, JC-1/DiOC$_2$(3), DYECYCLE™ Green, DYECYCLE™ Orange, Rhodamine 123, YO-PRO dyes, YO-PRO®-1, Propidium Iodide, SNARF® dyes, SYTOX dyes, SYTOX® Red, FURA-RED™, AmCyan, PerCp, Indo-1, Calcein Blue, DAPI, 7-AAD, Pacific Blue, ALEXA FLUOR® 405, ALEXA FLUOR® 488, ALEXA FLUOR® 546, ALEXA FLUOR® 610, RPE-ALEXA FLUOR® 610, ALEXA FLUOR® 647, ALEXA FLUOR® 700, RPE-ALEXA FLUOR® 700, ALEXA FLUOR® 750, APC-ALEXA FLUOR® 750, RPE-ALEXA FLUOR® 750, Pacific Orange, Quanum Dots, QDOT® 525 nanocrystals, QDOT® 565 nanocrystals, QDOT® 585 nanocrystals, QDOT® 605 nanocrystals, QDOT® 655 nanocrystals, QDOT® 705 nanocrystals, QDOT® 800 nanocrystals, RPE-CY®5 nanocrystals, and RPE-CY®7 nanocrystals.

Aldehyde Dehydrogenase (ALDH) Expression Analysis

Stem cells can be identified based on their aldehyde dehydrogenase (ALDH) activity. ALDH is a cytosolic enzyme that oxidizes a variety of aldehydes, including vitamin A. The enzyme ALDH is highly expressed in cells having stem cell properties, including, but not limited to, the capacity to produce differentiated progeny and undergo self-renewal.

Methods to identify and quantify the expression levels of ALDH involve the use of fluorescently labeled substrates or fluorogenic substrates that become fluorescent upon reaction with ALDH. By way of example only, the reagent ALDEFLUOR® can be used to identify and quantify the expression levels of ALDH in stem cells and progenitor cells. The fluorescent ALDEFLUOR® substrate can be used in conjunction with flow cytometry, including but not limited to FACS, to identify and isolate stem and progenitor cell populations. Specifically, the enzyme ALDH converts the ALDH substrate (ALDEFLUOR®), BAAA (BODIPY®-aminoacetaldehyde), into the fluorescent product BAA (BODIPY®-aminoacetate). BAAA is uncharged and is taken up by living cells through passive diffusion, whereas BAA is negatively charged and is retained within the cells. Therefore, cells expressing high levels of ALDH become brightly fluorescent (ALDH$^{high}$, also referred to herein as ALDH⁺) and can be identified and enumerated using a standard flow cytometer, such as FACS. In some embodiments, these cells have a high level of Aldehyde Dehydrogenase (ALDH high), e.g., relative to the level of ALHD in corresponding normal cells, such as in normal stem cells (e.g., normal hematological stem cells). "High" includes differences of at least about 25%, 50%, 2 fold, 5 fold, 10 fold, or any statistically significant difference. "ALDH high" includes both high ALDH protein or activity levels.

Cells expressing low levels of ALDH are not brightly fluorescent and are referred to as ALDH$^{low}$ or as ALDH⁻. Since only cells with an intact cellular membrane can retain the ALDEFLUOR® reaction product, only viable ALDH$^{high}$ cells are identified. Dead and/or dying cells without intact cellular membranes will not be counted.

The expression levels of aldehyde dehydrogenase (ALDH) ALDH of the various cell populations obtained using the cell separation/sorting methods disclosed above can be determined using such ALDH activity detection methods. In certain embodiments the populations of cells are CD138⁻/CD3⁻, CD138⁻/CD3 CD138⁺/CD3⁻ and CD138⁺/CD3⁺ and the expression level of ALDH of such cells is obtained using the methods described herein, including but not limited to the use of the reagent ALDEFLUOR®. In certain embodiments the populations of cells are CD138⁻/CD15⁻, CD138⁻/CD15 CD138⁺/CD15⁻ and CD138⁺/CD15⁺ and the expression level of ALDH of such cells is obtained using the methods described herein, including but not limited to the use of the reagent ALDEFLUOR®. In certain embodiments the populations of cells are CD138⁻/CD17⁻, CD138⁻/CD17 CD138⁺/CD17⁻ and CD138⁺/CD17⁺ and the expression level of ALDH of such cells is obtained using the methods described herein, including but not limited to the use of the reagent ALDEFLUOR®. In certain embodiments the populations of cells are CD138⁻/CD18⁻, CD138⁻/CD18⁺, CD138⁺/CD18⁻ and CD138⁺/CD18⁺ and the expression level of ALDH of such cells is obtained using the methods described herein, including but not limited to the use of the reagent ALDEFLUOR®. In certain embodiments the populations of cells are CD138⁻/CD19⁻, CD138⁻/CD19⁺/CD138⁺/CD19⁻ and CD138⁺/CD19 and the expression level of ALDH of such cells is obtained using the methods described herein, including but not limited to the use of the reagent ALDEFLUOR®. In certain embodiments the populations of cells are CD138⁻/CD20⁻, CD138⁻/CD20⁺, CD138⁺/CD20⁻ and CD138⁺/CD20⁺ and the expression level of ALDH of such cells is obtained using the methods described herein, including but not limited to the use of the reagent ALDEFLUOR®. In certain embodiments the populations of cells are CD138⁻/CD27⁻, CD138⁻/CD27⁺, CD138⁺/CD27⁻ and CD138⁺/CD27⁺ and the expression level of ALDH of such cells is obtained using the methods described herein, including but not limited to the use of the reagent ALDEFLUOR®. In certain embodiments the populations of cells are CD138⁻/CD30⁻, CD138⁻/CD30 CD138⁺/CD30⁻ and CD138⁺/CD30⁺ and the expression level of ALDH of such cells is obtained using the methods described herein, including but not limited to the use of the reagent ALDEFLUOR®. In certain embodiments the populations of cells are CD38⁻/CD34⁻, CD38⁻/CD34⁺, CD38⁺/CD34⁻ and CD38⁺/CD34⁺ and the expression level of ALDH of such cells is obtained using the methods described herein, including but not limited to the use of the reagent ALDEFLUOR®. In certain embodiments the populations of cells are CD138⁻/CD34⁻, CD138⁻/CD34⁺, CD138⁺/CD34⁻ and CD138⁺/CD34⁺ and the expression level of ALDH of such cells is obtained using the methods described herein, including but not limited to the use of the reagent ALDEFLUOR®.

Determination of Drug Resistance and/or Drug Sensitivity Using Efflux of Lipophilic Dyes A subset of stem cells, also referred to herein as the side population, can be identified by their ability to maintain a high efflux of capability for lipophilic dyes and antimitotic drugs. Cell populations that are drug resistant and/or drug sensitive have the capability for high efflux of lipophilic dyes, such as Hoechst 33342 dye. Additional dyes include but are not limited to cationic lipophilic dyes such as Vyebrant®DyeCycle™ stains. Further, additional assays for ABCG2/BCRP transporter activity are well-established in the art and contemplated herein. Exemplary assays include monitoring efflux of compounds such as, but not limited to, mitoxantrone, topotecan, and/or doxorubicin. Numerous assays for determining ABCG2/BCRP activity via monitoring the efflux of antimitotic drugs and dyes exist. The efflux capability of the various cell populations disclosed herein obtained using the cell separation/sorting methods and/or analyzed for ALDH expression levels can be determined using such analysis methods.

Determination of Presence of Immunoglobulin (Ig)

The presence of cells having memory B cell properties such as clonal Ig gene rearrangement or Ig light chain restriction can be determined by various detection methods and assays. In one embodiment, polymerase chain reaction amplification (PCR) is used to identify the extent and type of clonal Ig gene rearrangement. Various established methods of performing PCR can be employed and are contemplated herein. In a non-limiting example of PCR analysis, PCR amplified products of Ig heavy chain and/or light chain DNA are subjected to capillary electrophoresis (e.g. ABI Prism 3100 genetic analyzer) and evaluated using appropriate software (e.g. Genescan 2.1). Additionally, detection and/or identification of Ig on B cells can be performed using a variety of established detection assays. Non-limiting examples of such assays include use of antibodies that specifically bind known Ig determinants on the cell surface, including but not limited to immuno-fluorescent staining, ELISA-based assays, and FACS as described above. In one embodiment, clonal surface Ig light-chain restriction of a desired B-cell population is determined by staining the cells with kappa and/or lambda specific fluorescent antibodies followed by identification and/ or sorting using FACS. Thus, the presence of Ig and/or clonal Ig gene rearrangement of the various cell populations disclosed herein and obtained using the cell separation/sorting methods and/or analyzed for ALDH expression levels can be determined using such analysis methods.

Cancers

Described herein are methods to detect, analyze and/or quantify rare circulating cancer stem cells within the peripheral blood. Such methods can be used to monitor cancer stem cells in patients undergoing treatment and for relapse of disease. In addition, such methods can be useful for monitoring cancer stem cell targeted therapies, and can be used to help predict long-term clinical outcomes.

In some embodiments, the cancer is, by way of non-limiting example, brain cancer, breast cancer, lung cancer, ovarian cancer, pancreatic cancer, prostate cancer, renal cancer, colorectal cancer, leukemia, myeloid leukemia, acute myeloid leukemia (AML), glioblastoma, follicular lymphoma, pre-B acute leukemia, chronic lymphocytic B-leukemia, mesothelioma or small cell lung cancer. Additional cancers to be treated with the methods and compositions described herein include hematologic and non-hematologic cancers. Hematologic cancer includes multiple myeloma, leukemias, and lymphomas, acute leukemia, acute lymphocytic leukemia (ALL) and acute nonlymphocytic leukemia (ANLL), chronic lymphocytic leukemia (CLL) and chronic myelogenous leukemia (CML). Lymphoma further includes Hodgkin's lymphoma and non-Hodgkin's lymphoma, cutaneous t-cell lymphoma (CTCL), pediatric acute leukemia, pediatric acute myeloid leukemia, pediatric acute lymphoid leukemia, and mantle cell lymphoma (MCL). Non-hematologic cancer includes brain cancer, cancers of the head and neck, lung cancer, breast cancer, cancers of the reproductive system, cancers of the gastro-intestinal system, pancreatic cancer, and cancers of the urinary system, cancer of the upper digestive tract or colorectal cancer, bladder cancer or renal cell carcinoma, and prostate cancer.

Additional cancers include: cancers of oral cavity and pharynx, cancers of the respiratory system, cancers of bones and joints, cancers of soft tissue, skin cancers, cancers of the genital system, cancers of the eye and orbit, cancers of the nervous system, cancers of the lymphatic system, and cancers of the endocrine system. These cancers further include cancer of the tongue, mouth, pharynx, or other oral cavity; esophageal cancer, stomach cancer, or cancer of the small intestine; colon cancer or rectal, anal, or anorectal cancer; cancer of the liver, intrahepatic bile duct, gallbladder, pancreas, or other biliary or digestive organs; laryngeal, bronchial, and other cancers of the respiratory organs; heart cancer, melanoma, metastatic melanoma, basal cell carcinoma, squamous cell carcinoma, other non-epithelial skin cancer; uterine or cervical cancer; uterine corpus cancer; ovarian, vulvar, vaginal, or other female genital cancer; prostate, testicular, penile or other male genital cancer; urinary bladder cancer; cancer of the kidney; renal, pelvic, or urethral cancer or other cancer of the genito-urinary organs; thyroid cancer or other endocrine cancer; chronic lymphocytic leukemia; and cutaneous T-cell lymphoma, both granulocytic and monocytic.

Yet other cancers which are included herein include: adenocarcinoma, angiosarcoma, astrocytoma, acoustic neuroma, anaplastic astrocytoma, basal cell carcinoma, blastoglioma, chondrosarcoma, choriocarcinoma, chordoma, craniopharyngioma, cutaneous melanoma, cystadenocarcinoma, endotheliosarcoma, embryonal carcinoma, ependymoma, Ewing's tumor, epithelial carcinoma, fibrosarcoma, gastric cancer, genitourinary tract cancers, glioblastoma multiforme, hemangioblastoma, hepatocellular carcinoma, hepatoma, Kaposi's sarcoma, large cell carcinoma, leiomyosarcoma, liposarcoma, lymphangiosarcoma, lymphangioendotheliosarcoma, medullary thyroid carcinoma, medulloblastoma, meningioma mesothelioma, myelomas, myxosarcoma neuroblastoma, neurofibrosarcoma, oligodendroglioma, osteogenic sarcoma, epithelial ovarian cancer, papillary carcinoma, papillary adenocarcinomas, parathyroid tumors, pheochromocytoma, pinealoma, plasmacytomas, retinoblastoma, rhabdomyosarcoma, sebaceous gland carcinoma, seminoma, skin cancers, melanoma, small cell lung carcinoma, squamous cell carcinoma, sweat gland carcinoma, synovioma, thyroid cancer, uveal melanoma, and Wilm's tumor.

The methods disclosed herein can be used to detect, analyze, isolate and quantify cancer stem cells from hematologic malignancies including, but not limited to, lymphoma (including, but not limited to, Hodgkin's lymphoma, diffuse large b-cell lymphoma (DLBCL) also know as immunoblastic lymphoma, aggressive lymphomas also known as intermediate and high grade lymphomas, indolent lymphomas also known as low grade lymphomas, mantle cell lymphoma, follicular lymphoma), leukemia, acute promyelocytic leukemia, acute myeloid leukaemia, chronic myeloid leukaemia, chronic lymphocytic leukemia, Hodgkin's disease, multiple myeloma, myelodysplasia, and myeloproliferative disease.

In some embodiments, the methods disclosed herein can be used to detect, analyze, isolate and quantify cancer stem cells from human B cell malignancies including, but not limited to, non-Hodgkin's lymphoma, Hodgkin's disease and multiple myeloma. The methods disclosed herein utilize defined phenotypic and functional characteristics to identify and quantify such B cell malignancies.

The methods described herein can be used to detect, analyze, isolate and quantify cancer stem cells from cancers of epithelial origin including, but not limited to, actinic keratoses, arsenic keratoses, xeroderma pigmentosum, Bowen's disease, leukoplakias, metaplasias, dysplasias and papillomas of mucous membranes, e.g. of the mouth, tongue, pharynx and larynx, precancerous changes of the bronchial mucous membrane such as metaplasias and dysplasias (especially frequent in heavy smokers and people who work with asbestos and/or uranium), dysplasias and leukoplakias of the cervix uteri, vulval dystrophy, precancerous changes of the bladder, e.g. metaplasias and dysplasias, papillomas of the bladder as well as polyps of the intestinal tract. Non-limiting examples of semi-malignant or malignant cancers/tumors of the epithelial origin are breast cancer, skin cancer (e.g., basal cell carcinomas), bladder cancer (e.g., superficial bladder carcinomas), colon cancer, gastro-intestinal (GI) cancer, prostate cancer, uterine cancer, cervical cancer, ovarian cancer, esophageal cancer, stomach cancer, laryngeal cancer and lung cancer.

The methods described herein can be used to detect, analyze, isolate and quantify cancer stem cells from a neuroendocrine cancer, including but not limited to, lung and pancreatic cancers as well as neuroendocrine tumors of the digestive system. More specifically, these types of cancer may be called gastrinoma, insulinoma, glucagonoma, vasoactive intestinal peptideoma (VIPoma), PPoma, somatostatinoma, CRHoma, calcitoninoma, GHRHoma, ACTHoma, and GRFoma. Additional examples of neuroendocrine cancers include medullary carcinoma of the thyroid, Merkel cell cancer, small-cell lung cancer (SCLC), large-cell neuroendocrine carcinoma of the lung, neuroendocrine carcinoma of the cervix, Multiple Endocrine Neoplasia type 1 (MEN-1 or MEN1), Multiple Endocrine Neoplasia type 2 (MEN-2 or MEN2), neurofibromatosis type 1, tuberous sclerosis, von Hippel-Lindau (VHL) disease, neuroblastoma, pheochromocytoma (phaeochromocytoma), paraganglioma, neuroendocrine tumor of the anterior pituitary, and Carney's complex.

Hodgkin's Lymphoma

Figure 2:
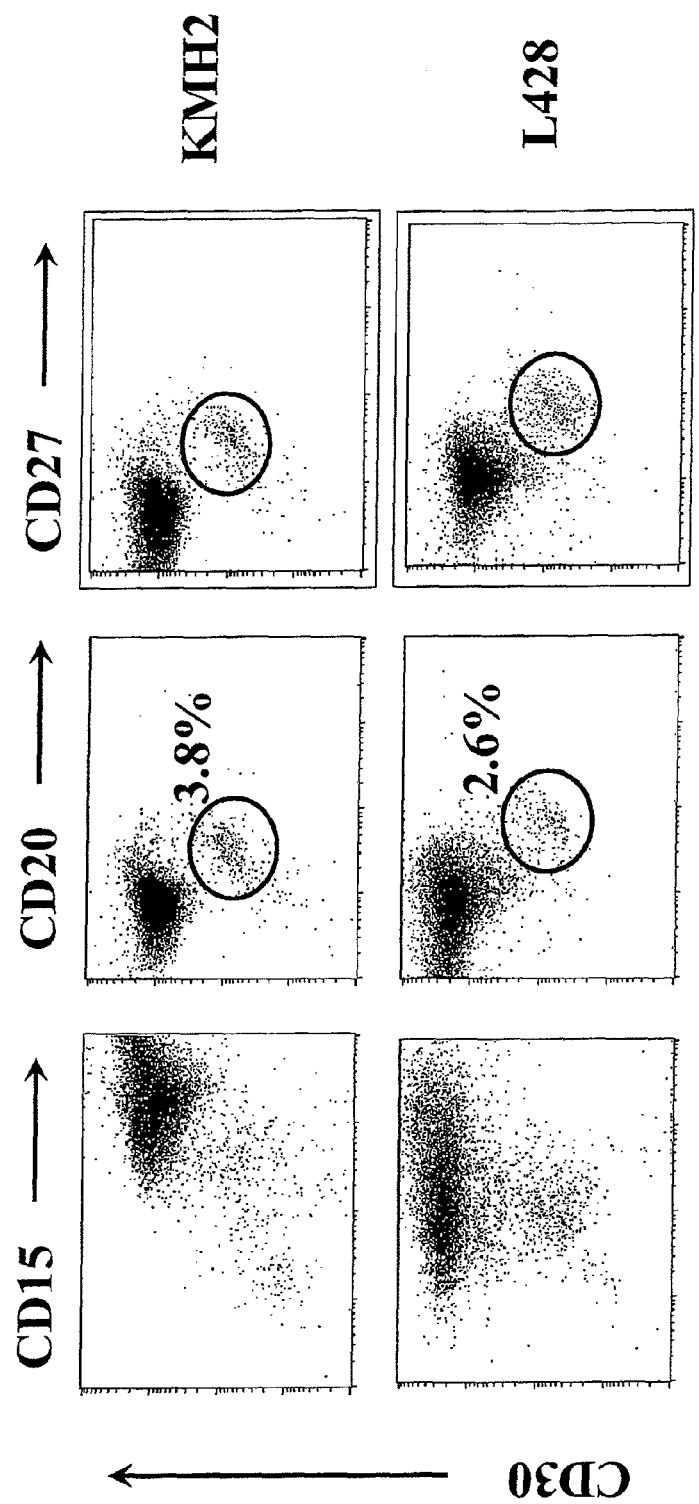
FIG. 2 are plots obtained from FACS analysis showing that Hodgkin's Lymphoma cell lines KMH2 and L428 contain distinct B cell populations.
Figure 3:
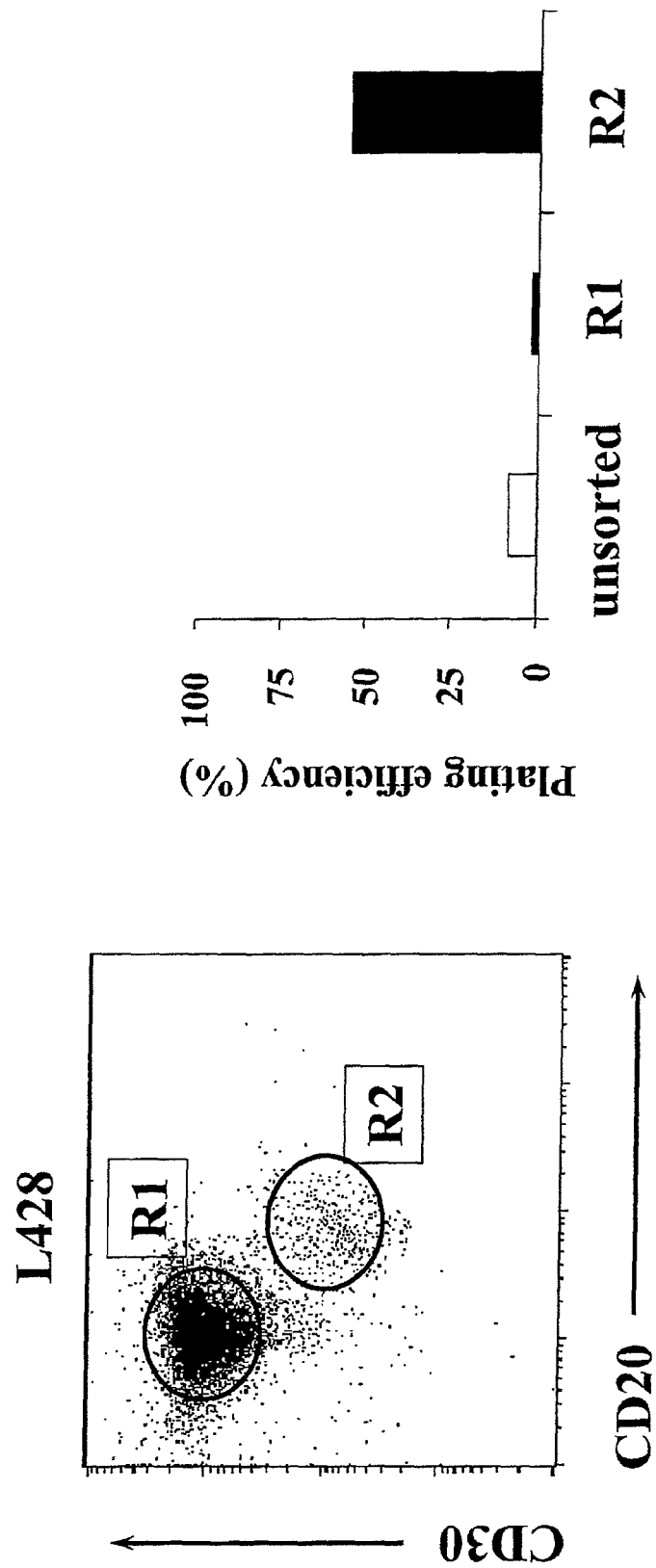
FIG. 3 are plots obtained from FACS analysis and a plating analysis showing that the phenotypic B cells from Hodgkin's Lymphoma cell line L428 are clonogenic.
Figure 4:
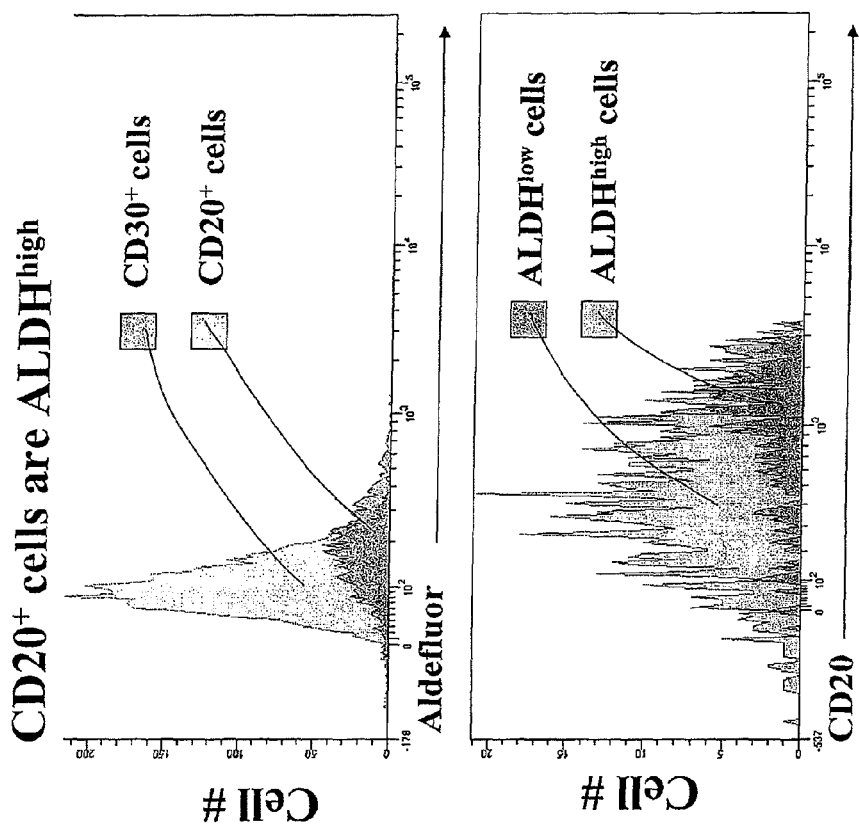
FIG. 4 are plots obtained from FACS analysis showing that the phenotypic B cells from Hodgkin's Lymphoma cell line L428 that are CD20 are also ALDH$^{high}$.
Figure 5:
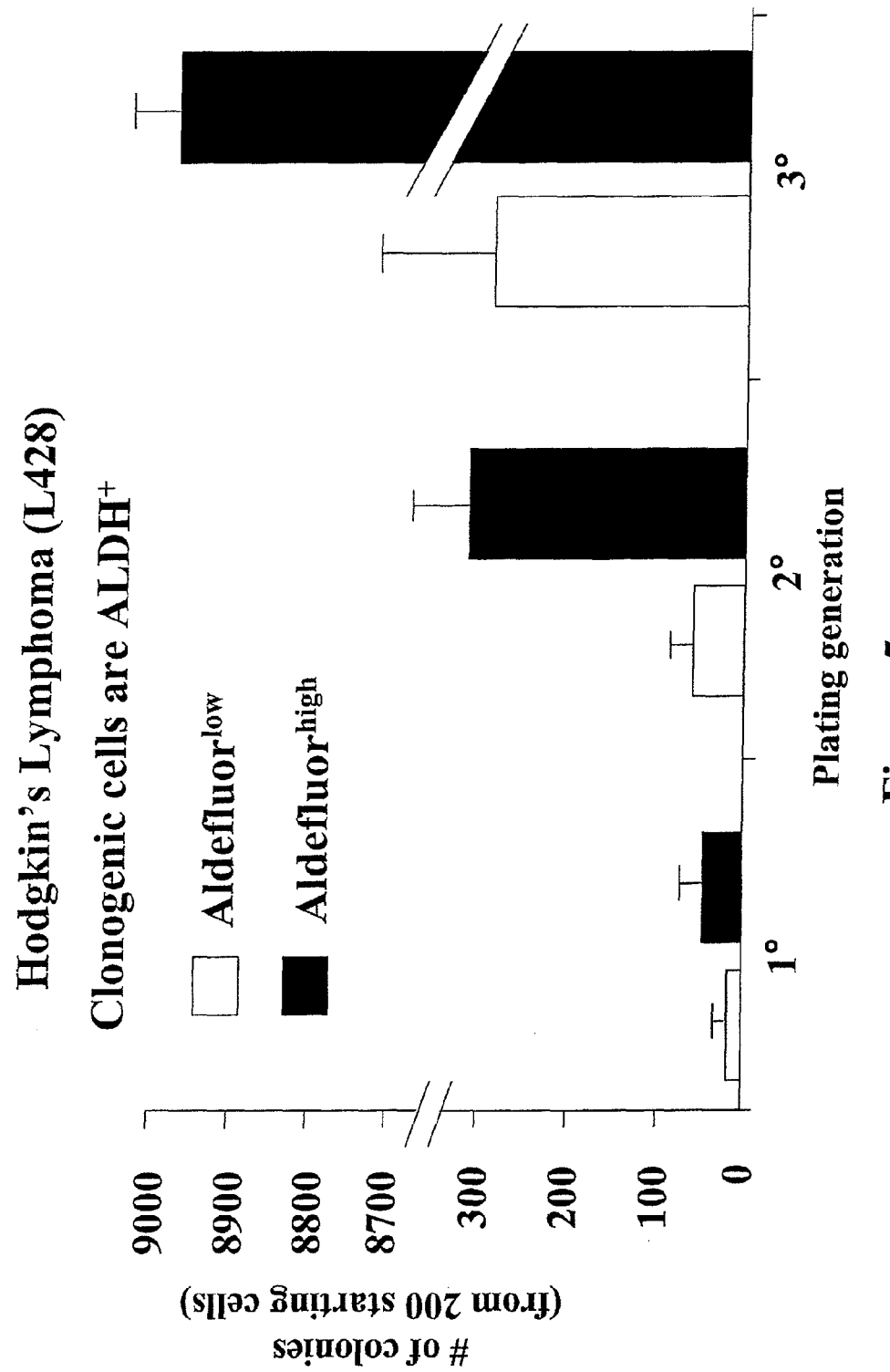
FIG. 5 is a plot obtained from a plating analysis showing that the phenotypic B cells from Hodgkin's Lymphoma cell line L428 that are CD20 and ALDH$^{high}$ are also clonogenic.

Using the separation and identification methods disclosed herein HL cell lines (L428, KM-H2) were found to contain a small (<5%) subpopulation of cells that do not express the Reed-Sternberg (RS) markers CD15 and CD30, but rather resembled memory B cells (markers $CD19^+$ $CD20^+$ and $CD27^+$) (FIG. 2). FIG. 3 shows that these phenotypic B cell subpopulation are clonogenic. In addition, the RS cells were found to express the plasma cell (PC) cell surface antigen CD138 (syndecan-1). Therefore, using the methods disclosed herein, populations of CD138+ and CD138− were obtained from HL cell lines, which were further isolated into population of $CD138^+/CD15^+$, $CD138^-/CD15^-$, $CD138^+/CD30^+$, $CD138^-/CD30^-$, $CD138^-/CD19^+$, $CD138^-/CD20^+$ and $CD138^-/CD27^+$. These populations were then analyzed for ALDH expression levels and it was found that the clonogenic subpopulation that resembled memory B cells expressed high ALDH activity and monoclonal immunoglobulin light chain expression, while the predominant RS cells exhibit low activity (see FIG. 4, comparing ALDH expression levels for $CD30^+$ cells to $CD20^+$ cells). Furthermore, the $ALDH^{high}$ cells were able to self-renew as seen by the increase in colony number indicating these cells behave as stem cells. (FIG. 5)

Figure 6:
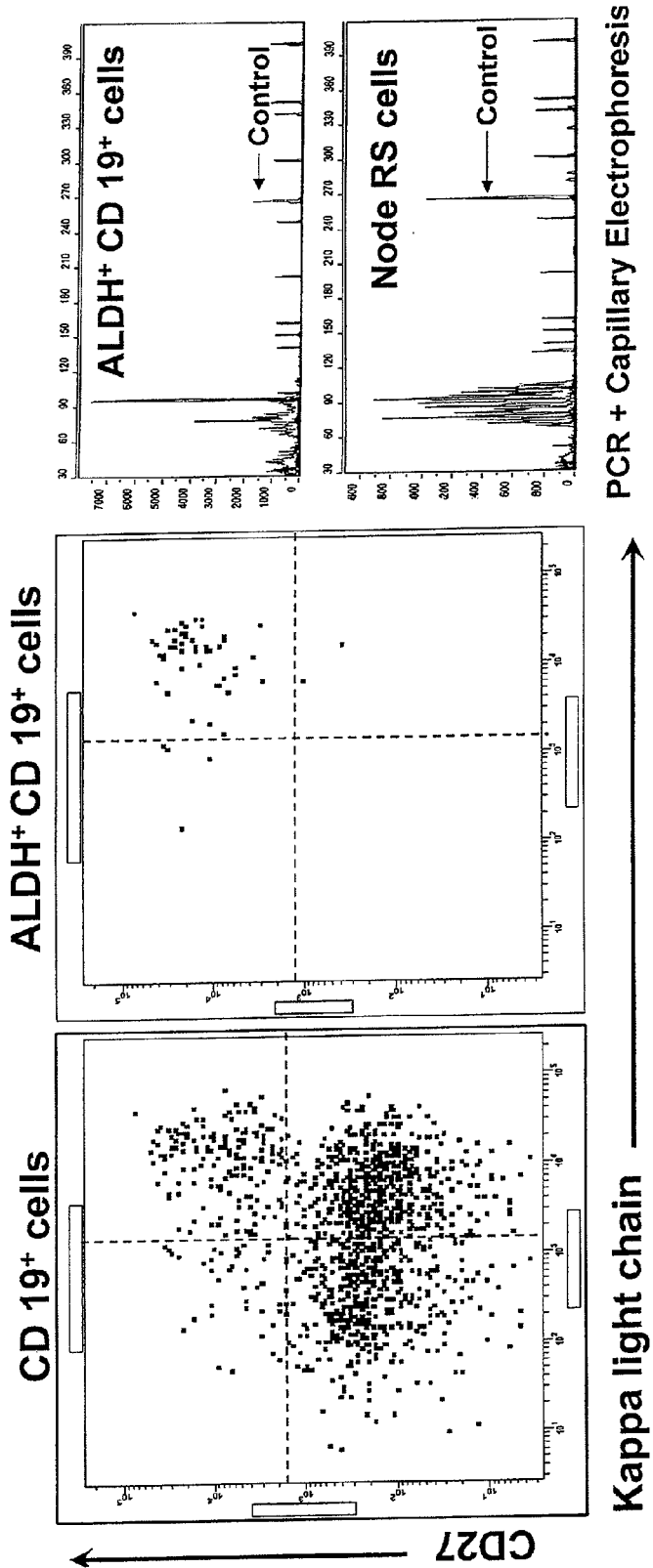
FIG. 6 are plots obtained from FACS analysis, PCR and capillary electrophoresis showing that the clonotypic B cells from Hodgkin's Lymphoma circulate.

Using the separation and identification methods described herein, such clonotypic memory B cells were found to circulate even in early stage HL patients. Specifically, $CD19^+$ cells were isolated from patient marrow or blood. The bulk CD19 cells and those that are $ALDH^{low}$, isolated from HL patients were a mixture of non-clonal naive and memory B cells. However, the $ALDH^{high}$ $CD19^+$ cells were a highly enriched population of immunoglobulin (Ig) light chain-restricted $CD27^+$ memory B cells that represented 0.7 to 3% of the circulating $CD19^+$ cells (FIG. 6). The $ALDH^{high}$ $CD19^+$ cells also displayed clonal Ig gene rearrangement by polymerase chain reaction (PCR) amplification. CD15 $CD30^+$ RS cells isolated from fresh diagnostic lymph nodes contained clonal Ig gene rearrangement as seen in circulating $ALDH^{high}$ $CD19^+$ B cells. Therefore, clonotypic memory B cells can be found in both HL cell lines and patients.

Multiple Myeloma

Figure 7:
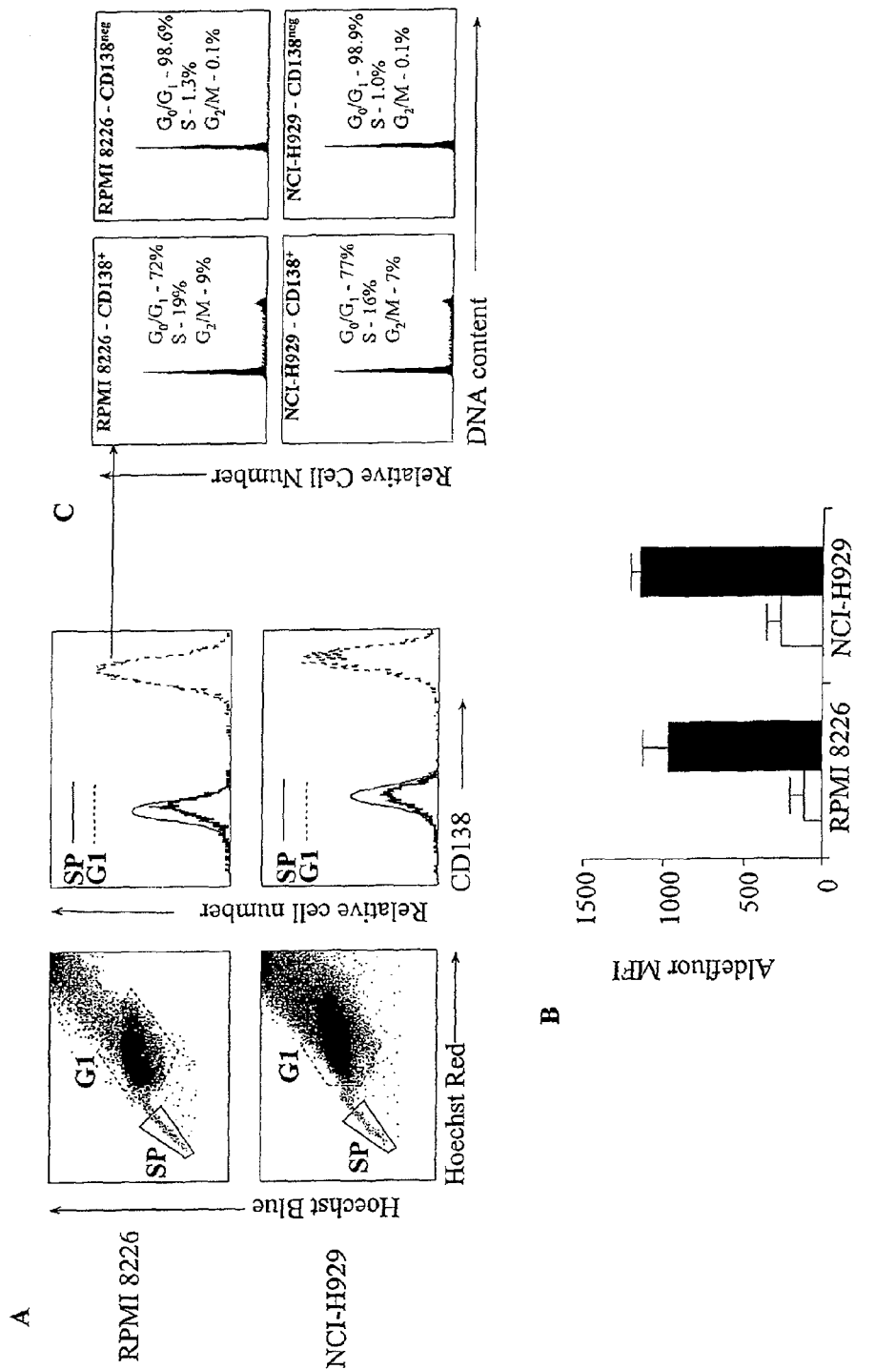
FIG. 7 illustrates that MM precursors display stem cell characteristics. (A) Expression of CD138 by RPMI 8226 and NCI-H929 side population (SP) or non-side population (G1) cells labelled with Hoechst 33342 and anti-human CD138. Shaded histogram represents staining with an isotype control antibody. (B) Relative mean fluorescence intensity (MFI) of Aldefluor by RPMI 8226 and NCI-H929 CD138$^+$ (open bars) and CD138$^-$ (black bars) cells. Values are mean±SEM of 4 experiments. (C) Cell cycle profile of RPMI 8226 and NCI-H929 CD138$^+$ and CD138$^-$ cells following PI staining.

Normal tissue-restricted adult stem cells are highly resistant to toxic injury that appears to be multi-factorial in nature. In addition, some of these processes serve as the basis for flow cytometric assays that can enrich for adult stem cells, and we examined whether these assays could distinguish cellular compartments in MM. The ATP binding cassette family of membrane transporters actively export xenobiotics thereby limiting the intracellular accumulation of these compounds. Furthermore, efflux of the DNA binding dye Hoechst 33342 by the ABCG2/BCRP transporter is required for detection of the "side population" phenotype that is characteristic of stem cells from many tissues. To examine whether the side population assay could identify clonogenic MM precursors, two human MM cell lines, RPMI 8226 and NCI-H929, were stained with Hoechst 33342 and found that each contained small populations of side population cells (0.8-1.9% of total cells, FIG. 7A). Furthermore, co-staining for CD138 demonstrated that the side population cells were almost exclusively $CD138^-$ (>97%) in comparison to the bulk of the population which was $CD138^+$ (FIG. 7A).

Normal adult stem cells typically exhibit higher relative levels of ALDH activity than their differentiated progeny, and the fluorescently labeled ALDH substrate ALDEFLUOR® can be used to isolate stem cells from a number of adult tissues. Staining of RPMI 8226 and NCI-H929 cells revealed small populations of $ALDH^+$ cells accounting for 3.7% and 4.3% of cells, respectively. Furthermore, co-staining cells for CD138 expression demonstrated that the $CD138^-$ cells had significantly higher levels of ALDH activity than $CD138^+$ plasma cells (FIG. 7B).

Cellular quiescence is exhibited by most normal adult stem cells, and this property is thought to be a major mechanism of drug resistance. To determine whether MM precursors are relatively quiescent, immature $CD138^-$ cells or $CD138^+$ plasma cells were isolated from the RPMI 8226 and NCI-H929 cell lines and stained with propidium iodide (PI) to evaluate their cell cycle status. Nearly all (>98%) of the $CD138^-$ cells in both cell lines were in G0/G1, compared to only 72% or 77% of the $CD138^+$ cells (FIG. 7C).

Clonogenic MM precursors resemble memory B cells in depleted primary bone marrow specimens of cells expressing the B cell surface antigen CD20 and the memory B cell surface marker CD27. Compared to the starting population of $CD138^-$ $CD34^-$ cells, depletion of CD20 or CD27 from the $CD138^-$ $CD34^-$ cell population significantly limited clonogenic MM growth (88% and 83%, respectively, FIG. 8A;

P<0.001). In contrast, the removal of CD3 T cells did not have a significant effect on the clonogenic recovery of MM colonies (FIG. 8A; P>0.1). Thus, the phenotype of MM cells with in vitro clonogenic potential, CD138$^-$ CD20$^+$ CD27$^+$, parallels normal memory B cells.

Rituximab and alemtuzumab, two humanized monoclonal antibodies that target the B-cell antigens CD20 and CD52, respectively, inhibit clonogenic MM cells. CD138$^-$ precursors or CD138$^+$ plasma cells were isolated from the RPMI 8226 or NCI-H929 cell lines and treated with each of the two humanized monoclonal antibodies, rituximab or alemtuzumab, and in combination with human complement that strongly enhances their in vitro activity through complement dependent cytoxicity. Neither complement alone nor the monoclonal antibodies with or without complement affected the clonogenic growth of CD138$^+$ plasma cells that lack the target antigens (FIG. 8B; P>0.3 for all groups compared to the untreated control). However, both antibodies significantly inhibited the clonogenic recovery of CD138$^-$ mM progenitors from both cell lines when combined with complement (FIG. 8B; P<0.01 for each combination compared to the complement alone or untreated control groups). Similarly, each combination of monoclonal B cell antibody and complement significantly inhibited the clonogenic recovery of CD138$^-$ mM progenitors isolated from 4 primary patient specimens (FIG. 8C; P<0.001).

Figure 8:
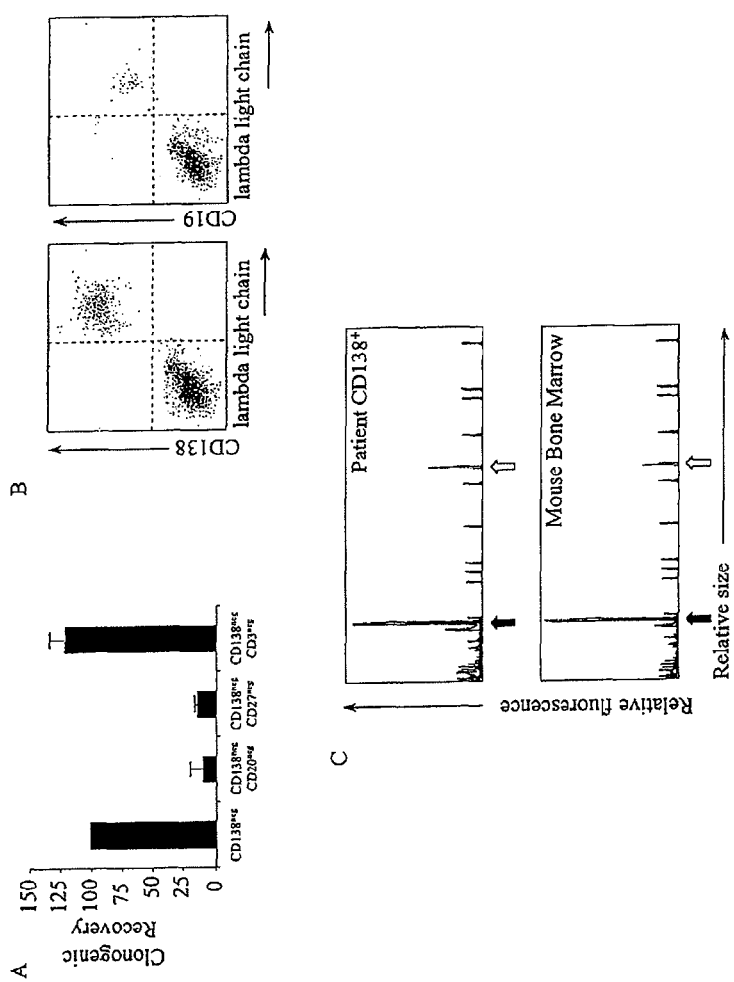
FIG. 8 illustrates that MM progenitors resemble normal memory B cells and display properties typical of normal stem cells. (A) Relative colony formation by CD138$^-$ CD34$^-$ bone marrow mononuclear cells (CD138$^{neg}$) isolated from 4 patients with MM following depletion of additional cells expressing CD20, CD27 or CD3. Values represent the mean±SEM. (B) Clonogenic recovery of CD138$^+$ (open bars) or CD138$^-$ (black bars) cells from the MM cell lines RPMI 8226 and NCI-H929 following treatment with rituximab (Ritux), alemtuzumab (Alemtuz) and/or human complement (C). Values represent means±SEM of 4 experiments. (C) Clonogenic recovery of CD138$^-$ mM progenitors derived from primary clinical specimens following antibody treatment without (open bars) or with (black bars) human complement. (D) Engraftment of NOD/SCID mice with peripheral blood memory B cells derived from patients with MM. Flow cytometric analysis of NOD/SCID mouse bone marrow cells for expression of human CD138 and intracellular Ig lambda light chain (left panel) or CD19 and surface Ig lambda light chain (right panel) following injection of peripheral blood memory B cells. (E) Comparison of capillary electorphoretic profiles of Ig heavy chain CDR3 amplification products (black arrow) obtained by PCR of CD138$^+$ MM plasma cells isolated from the primary clinical bone marrow specimen or from bone marrow cells collected from a mouse injected with memory B cells from the same patient. The open arrow represents a control PCR reaction product.

The functional growth capacity of clonotypic memory B cells to engraft NOD/SCID mice was evaluated. CD19$^+$ CD27$^+$ B cells isolated from the peripheral blood of 4 patients with MM were injected into NOD/SCID mice. All recipient animals developed hind limb paralysis, along with detectable human CD138 plasma cells (6.6-15% of the total bone marrow cells) 4 to 6 months after injection. In contrast, no engraftment was detected following the injection of 1×10$^7$ of the corresponding CD138$^+$ plasma cells isolated from each MM patient. The human plasma cells recovered from the mice were found to be clonally related to the original human MM plasma cells by Ig light chain expression (FIG. 8D), Ig heavy chain gene CDR3 length restriction (FIG. 8E) and CDR3 DNA sequence. Small populations of Ig light chain-restricted CD19$^+$CD27$^+$ cells were also detected (0.01-0.06% of total bone marrow cells; FIG. 8D), and injection of these cells (10.8–100×10$^3$ cells) into secondary recipients similarly produced MM engraftment after 4 to 6 months.

Figure 9:
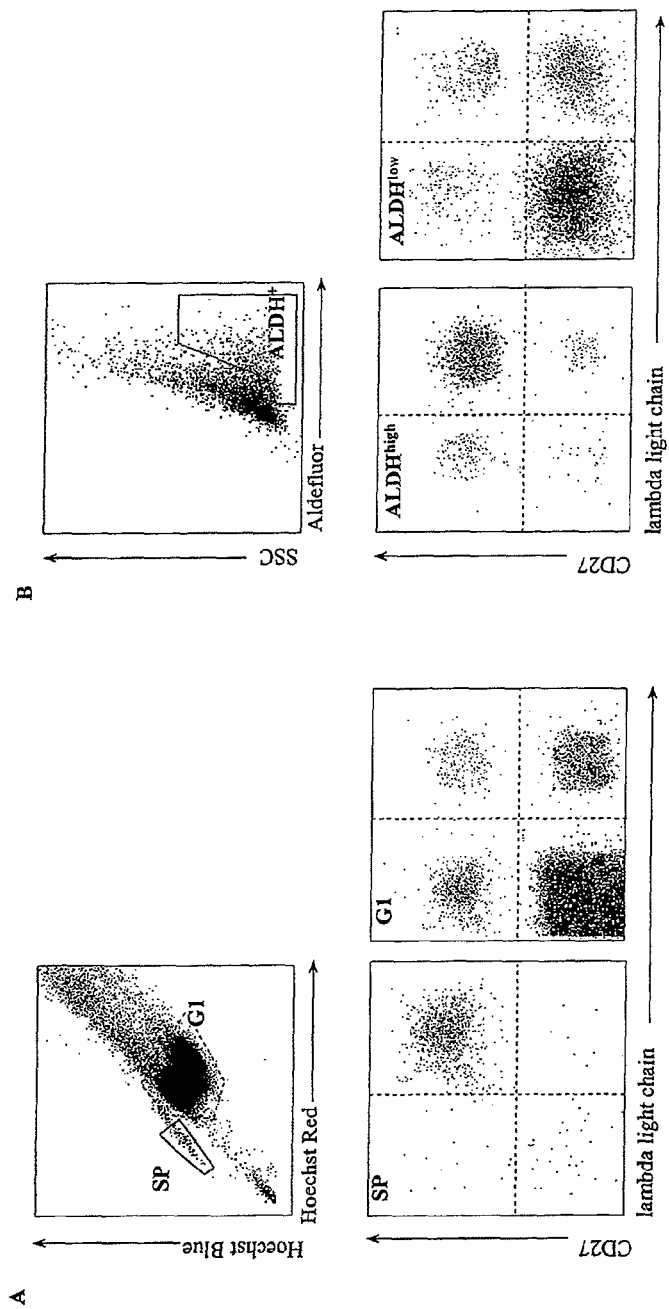
FIG. 9. Circulating MM stem cells display properties typical of normal stem cells. (A) Expression of CD27 and surface Ig light chain expression by peripheral blood B cells with the side population (SP) or non-side population (G1) phenotype derived from a representative MM patient. (B) Expression of CD27 and surface immunoglobulin light chain expression by peripheral blood B cells with high or low Aldefluor fluorescence derived from a representative MM patient.

Using the methods described herein, including side population and ALDH assays, CD138$^-$ precursors were identified within MM cell lines. Similarly, these methods were used to identify MM precursors in primary clinical specimens. CD19$^+$ B cells isolated from the peripheral blood of 4 mM patients were stained with Hoechst 33342 and a small numbers of side population cells were detected (0.18-0.83% of total B cells; FIG. 9A). Further surface staining demonstrated that the majority (89-97%) of the side population B cells expressed CD27 and clonal surface Ig light chain restriction that matched each patient's MM plasma cells (FIG. 9A). In contrast, non-side population cells contained a mixture of CD27$^+$ memory and CD27$^-$ naïve B cells expressing both Ig light chains (G1, FIG. 9A). These peripheral blood CD19$^+$ B cells were also stained with ALDEFLUOR® and small populations of ALDH$^+$ cells were identified. Similar to the side population B cells, most (86-93%) of the ALDH$^+$ B cells expressed CD27 and clonotypic surface Ig light chain (FIG. 9B). In contrast, ALDH$^-$ cells contained a mixture of non-clonal CD27 positive and negative cells expressing both kappa and lambda Ig light chains (FIG. 9B).

Methods of Use

Detection of Cancer

Methods for determining whether a subject has, or is likely to develop a cancer, comprising determining whether the subject has cells that are ALDH$^+$ in the patients blood or in the patients stem cells, wherein the presence of ALDH$^+$ cells indicates that the subject has or is likely to develop a cancer, are described herein. In some embodiments, although not all, the determining step comprises the steps of obtaining a sample from the patient; isolating a predetermined population of cells from the sample using at least one of flow cytometry, fluorescence activated cell sorting, panning, affinity column separation and magnetic selection; and determining whether the isolated cells are ALDH$^+$. The step of isolating the population of cells can be performed by any method known in the art, including the separation methods described herein such as flow cytometry, fluorescence activated cell sorting, antibody-dependent depletion, antibody-dependent solid phase capture, panning, affinity column separation and magnetic selection. In various embodiments, the presence of a high expression of ALDH (ALDH$^{high}$) is used to determine the presence of circulating undifferentiated cells, including circulating cancer stem cells. In some embodiments, the cancer is one of the cancers described in the above section.

Also provided herein are methods for isolating and identifying undifferentiated cells, including circulating cancer stem cells, disclosed herein that can be used for the detection of a cancer in a patient. In some embodiments, the undifferentiated cells are from the patient's blood. In other embodiments, the undifferentiated cells are from the patient's bone marrow. Such methods include the steps of first obtaining a sample from a patient (e.g., a blood sample and/or a bone marrow sample); then isolating a predetermined population of cells from the blood sample using at least one of the separation methods described herein. Such separation methods include, but are not limited to, flow cytometry, fluorescence activated cell sorting, antibody-dependent depletion, antibody-dependent solid phase capture, panning, affinity column separation and magnetic selection. The expression level of ALDH in the isolated predetermined population is then obtained. The presence of a high expression of ALDH (ALDH$^{high}$) is used to determine the presence of circulating undifferentiated cells, including circulating cancer stem cells. In some embodiments, the cancer is one of the cancers described in the above section.

In certain embodiments of such methods, the cancer is a B cell malignancy, while in other embodiments the cancer is multiple myeloma. In certain embodiments of such methods, the cancer is Hodgkin's disease, while in other embodiments the cancer is non-Hodgkin's lymphoma. In certain embodiments of such methods, the cancer is not multiple myeloma. In certain embodiments of such methods, the cancer is not Hodgkin's disease, while in other embodiments the cancer is not non-Hodgkin's lymphoma.

In certain embodiments of such methods, the predetermined population of cells comprise one or more of the following markers: Hoechst (i.e. Hoechst Side Population), CD138$^-$, CD30$^-$, CD3$^-$, CD52$^+$, CD27$^+$, CD20$^+$, and CD19$^+$. While in other embodiments the predetermined population of cells comprise two or more of the following markers: Hoechst (i.e. Hoechst Side Population), CD138$^-$, CD30$^-$, CD3$^-$, CD52$^+$, CD27$^+$, CD20$^+$, and CD19$^+$. While in other embodiments the predetermined population of cells comprise three or more of the following markers: Hoechst (i.e. Hoechst Side Population), CD138$^-$, CD30$^-$, CD3$^-$, CD52$^+$, CD27$^+$, CD20$^+$, and CD19$^+$. While in other embodiments the predetermined population of cells comprise four or more of the following markers: Hoechst (i.e. Hoechst Side Population), CD138$^-$, CD30$^-$, CD3$^-$, CD52$^+$, CD27$^+$, CD20$^+$, and CD19$^+$.

While in other embodiments the predetermined population of cells comprise five or more of the following markers: Hoechst (i.e. Hoechst Side Population), $CD138^-$, $CD30^-$, $CD3^-$, $CD52^+$, $CD27^+$, $CD20^+$, and $CD19^+$. While in other embodiments the predetermined population of cells are $CD20^+$. In certain embodiments of such methods, the predetermined population of cells are $CD19^+$, while in other embodiments the predetermined population of cells are $CD27^+$. In certain embodiments of such methods, the predetermined population of cells are Hoechst, while in other embodiments the isolated cells are $ALDH^+$. In certain embodiments of such methods, the predetermined population of cells are $CD15^-$, while in other embodiments the predetermined population of cells are $CD30^-$. In certain embodiments of such methods (e.g., in certain embodiments of leukemia), the predetermined population of cells are $CD34^+$. In other embodiments of such methods (e.g., in certain embodiments of multiple myeloma), the predetermined population of cells are $CD34^-$. In certain embodiments of such methods, the isolated cells are $ALDH^+$, while in other embodiments the isolated cells are $CD138^-$.

In certain embodiments of such methods, the cancer is Hodgkin's Lymphoma (HL) and the cancer stem cells are $CD138^-/CD19$; $CD138^-/CD20$; $CD138^-/CD27$; $CD138^-/CD15^-$, $CD138^-/CD52^+$ and/or $CD138^-/CD30^-$. In certain embodiments of such methods, the cancer is Hodgkin's Lymphoma (HL) and the cancer stem cells are $ALDH^+/CD138^-/CD19^+$; $ALDH^+/CD138^-/CD20^+$; $ALDH^+/CD138^-/CD27^+$; $ALDH^+/CD138^-/CD15^-$, $ALDH^+/CD138^-/CD52^+$ and/or $ALDH^+/CD138^-/CD30^-$. In some embodiments, the cancer is Hodgkin's Lymphoma and the cancer stem cells are $CD19^+$, $CD20^+$, $CD27^+$, $CD15^-$, $CD52^+$ and/or $CD30^-$.

In certain embodiments of such methods, the cancer is Multiple Myeloma and the cancer stem cells are $CD138^-/CD27$; $CD138^-/CD34^-$, $CD138^-/CD19^+$, $CD138^-/CD52^+$ and/or $CD138^-/CD20^+$. In certain embodiments of such methods, the cancer is Multiple Myeloma and the cancer stem cells are $ALDH^+/CD138^-/CD27^+$, $ALDH^+/CD138^-/CD34^-$, $ALDH^+/CD138^-/CD52^+$, $ALDH^+/CD138^-/CD19^+$, and/or $ALDH^+/CD138^-/CD20^+$. In some embodiments, the cancer is Multiple Myeloma and the cancer stem cells are $CD138^-$, $CD27^+$, $CD19^+$ and/or $CD20^+$.

In certain embodiments of such methods, the cancer is leukemia and the cancer stem cells are $CD138^-/CD34^+$ and/or $CD138^-/CD38^-$. In certain embodiments of such methods, the cancer is leukemia and the cancer stem cells are $ALDH^+/CD138^-/CD34^+$ and/or $ALDH^+/CD138^-/CD38^-$. In some embodiments, the cancer is leukemia and the cancer stem cells are $ALDH^+/CD34^+$, $ALDH^+/CD138^-$, $CD34^+$ or $CD138^-$.

In certain embodiments of such methods, the cancer is Non Hodgkin's Lymphoma and the cancer stem cells are $CD138^-/CD19^+$ and/or $CD138^-/CD20^+$. In certain embodiments of such methods, the cancer is Non Hodgkin's Lymphoma and the cancer stem cells are $ALDH^+/CD138^-/CD19^+$ and/or $ALDH^+/CD138^-/CD20^+$. In certain embodiments of such methods, the cancer is Non Hodgkin's Lymphoma and the cancer stem cells are $ALDH^+/CD19^+$ and/or $ALDH^+/CD20^+$.

In certain embodiments the sample is from the patient's blood, while certain embodiments the sample is from the patient's bone marrow.

Identifying Cancer Stem Cells

The methods for isolating and identifying circulating undifferentiated cells, including circulating cancer stem cells, disclosed herein can be used for monitoring the effectiveness of a cancer treatment in a patient. Such methods include the steps of first obtaining a sample from a patient (e.g., a blood sample and/or a bone marrow sample); then isolating a predetermined population of cells from the blood sample using at least one of the separation methods described herein. Such separation methods include, but are not limited to, flow cytometry, fluorescence activated cell sorting, antibody-dependent depletion, antibody-dependent solid phase capture, panning, affinity column separation and magnetic selection. The expression level of ALDH in the isolated predetermined population is then obtained. The presence of a high expression of ALDH ($ALDH^{high}$) is used to determine the presence of circulating undifferentiated cells, including circulating cancer stem cells. Finally, the number of $ALDH^{high}$ cells is compared to the number of $ALDH^{high}$ cells determined at an earlier time in the cancer treatment.

In certain embodiments of such methods, the cancer is a B cell malignancy, while in other embodiments the cancer is multiple myeloma. In certain embodiments of such methods, the cancer is Hodgkin's disease, while in other embodiments the cancer is non-Hodgkin's lymphoma. In certain embodiments of such methods, the cancer is not multiple myeloma. In certain embodiments of such methods, the cancer is not Hodgkin's disease, while in other embodiments the cancer is not non-Hodgkin's lymphoma.

In certain embodiments of such methods, the predetermined population of cells comprise one or more of the following markers: Hoechst (i.e. Hoechst Side Population), $CD138^-$, $CD30^-$, $CD3^-$, $CD52^+$, $CD27^+$, $CD20^+$, and $CD19^+$. While in other embodiments the predetermined population of cells comprise two or more of the following markers: Hoechst (i.e. Hoechst Side Population), $CD138^-$, $CD30^-$, $CD3^-$, $CD52^+$, $CD27^+$, $CD20^+$, and $CD19^+$. While in other embodiments the predetermined population of cells comprise three or more of the following markers: Hoechst (i.e. Hoechst Side Population), $CD138^-$, $CD30^-$, $CD3^-$, $CD52^+$, $CD27^+$, $CD20^+$, and $CD19^+$. While in other embodiments the predetermined population of cells comprise four or more of the following markers: Hoechst (i.e. Hoechst Side Population), $CD138^-$, $CD30^-$, $CD3^-$, $CD52^+$, $CD27^+$, $CD20^+$, and $CD19^+$. While in other embodiments the predetermined population of cells comprise five or more of the following markers: Hoechst (i.e. Hoechst Side Population), $CD138^-$, $CD30^-$, $CD3^-$, $CD52^+$, $CD27^+$, $CD20^+$, and $CD19^+$. While in other embodiments the predetermined population of cells are $CD20^+$. In certain embodiments of such methods, the predetermined population of cells are $CD19^+$, while in other embodiments the predetermined population of cells are $CD27^+$. In certain embodiments of such methods, the predetermined population of cells are Hoechst, while in other embodiments the isolated cells are $ALDH^+$. In certain embodiments of such methods, the predetermined population of cells are $CD15^-$, while in other embodiments the predetermined population of cells are $CD30^-$. In certain embodiments of such methods (e.g., in certain embodiments of leukemia), the predetermined population of cells are $CD34^+$. In other embodiments of such methods (e.g., in certain embodiments of multiple myeloma), the predetermined population of cells are $CD34^-$. In certain embodiments of such methods, the isolated cells are $ALDH^+$, while in other embodiments the isolated cells are $CD138^-$.

In certain embodiments of such methods, the cancer is Hodgkin's Lymphoma (HL) and the cancer stem cells are $CD138^-/CD19$; $CD138^-/CD20$; $CD138^-/CD27$; $CD138^-/CD15^-$, $CD138^-/CD52^+$ and/or $CD138^-/CD30^-$. In certain embodiments of such methods, the cancer is Hodgkin's Lymphoma (HL) and the cancer stem cells are $ALDH^+/CD138^-/CD19^+$; $ALDH^+/CD138^-/CD20^+$; $ALDH^+/CD138^-/CD27^+$; $ALDH^+/CD138^-/CD15^-$, $ALDH^+/CD138^-/CD52^+$ and/or $ALDH^+/CD138^-/CD30^-$. In some embodiments, the cancer is Hodgkin's Lymphoma and the cancer stem cells are CD19$^+$, CD20$^+$, CD27$^+$, CD15$^-$, CD52$^+$ and/or CD30$^-$.

In certain embodiments of such methods, the cancer is Multiple Myeloma and the cancer stem cells are CD138$^-$/CD27; CD138$^-$/CD34$^-$, CD138$^-$/CD19$^+$, CD138$^-$/CD52$^+$ and/or CD138$^-$/CD20$^+$. In certain embodiments of such methods, the cancer is Multiple Myeloma and the cancer stem cells are ALDH$^+$/CD138$^-$/CD27$^+$, ALDH$^+$/CD138$^-$/CD34$^-$, ALDH$^+$/CD138$^-$/CD52$^+$, ALDH$^+$/CD138$^-$/CD19$^+$, and/or ALDH$^+$/CD138$^-$/CD20$^+$. In some embodiments, the cancer is Multiple Myeloma and the cancer stem cells are CD138$^-$, CD27$^+$, CD19$^+$ and/or CD20$^+$.

In certain embodiments of such methods, the cancer is leukemia and the cancer stem cells are CD138$^-$/CD34$^+$ and/or CD138$^-$/CD38$^-$. In certain embodiments of such methods, the cancer is leukemia and the cancer stem cells are ALDH$^+$/CD38$^-$/CD34$^+$ and/or ALDH$^+$/CD38$^-$/CD38$^-$. In some embodiments, the cancer is leukemia and the cancer stem cells are ALDH$^+$/CD34$^+$, ALDH$^+$/CD38$^-$, CD34$^+$ or CD38$^-$.

In certain embodiments of such methods, the cancer is Non Hodgkin's Lymphoma and the cancer stem cells are CD138$^-$/CD19$^+$ and/or CD138$^-$/CD20$^+$. In certain embodiments of such methods, the cancer is Non Hodgkin's Lymphoma and the cancer stem cells are ALDH$^+$/CD138$^-$/CD19$^+$ and/or ALDH$^+$/CD138$^-$/CD20$^+$. In certain embodiments of such methods, the cancer is Non Hodgkin's Lymphoma and the cancer stem cells are ALDH$^+$/CD19$^+$ and/or ALDH$^+$/CD20$^+$.

In certain embodiments the sample is from the patient's blood, while certain embodiments the sample is from the patient's bone marrow.

In certain embodiments of such methods, the cancer treatment is a stem-cell targeted therapy, while in other embodiments the cancer treatment involves induction of terminal differentiation. In certain embodiments of such methods, the cancer treatment involves inhibition of telomerase, while in other embodiments the cancer treatment involves inhibition of developmental signaling pathways. In certain embodiments of such methods, the cancer treatment involves inhibition of intracellular signal transduction pathways, while in other embodiments the cancer treatment involves induction of active immunity to cellular antigens. In certain embodiments of such methods, the cancer treatment involves induction of passive immunity to cellular antigens, while in other embodiments the cancer treatment is for leukemia and the isolated cells are CD34$^+$ and CD38$^-$. In certain embodiments of such methods, the cancer treatment is for Hodgkin's Lymphoma and the isolated cells are CD19$^+$, CD20$^+$, CD27$^+$, CD15– and/or CD30–. In certain embodiments of such methods, the cancer treatment is for Multiple Myeloma and the isolated cells are CD138$^-$, CD27$^+$, CD19$^+$ and/or CD20$^+$. In certain embodiments of such methods, the cancer treatment is for Non Hodgkin's Lymphoma and the isolated cells are CD19$^+$ and/or CD20$^+$.

In various embodiments the presence of a high expression of ALDH (ALDH$^{high}$) determines the presence of circulating undifferentiated cells, including circulating cancer stem cells.

Detecting Minimal Residual Disease

The methods for isolating and identifying circulating undifferentiated cells, including circulating cancer stem cells, disclosed herein can be used for the detection of minimal residual disease in a cancer patient. Such methods include the steps of first obtaining a sample from a patient (e.g., a blood sample and/or a bone marrow sample); then isolating a predetermined population of cells from the blood sample using at least one of the separation methods described herein. Such separation methods include, but are not limited to, flow cytometry, fluorescence activated cell sorting, antibody-dependent depletion, antibody-dependent solid phase capture, panning, affinity column separation and magnetic selection. The expression level of ALDH in the isolated predetermined population is then obtained. The presence of a high expression of ALDH (ALDH$^{high}$) is used to determine the presence of circulating undifferentiated cells, including circulating cancer stem cells. The number of (ALDH$^{high}$) cells present is an indication of the minimal residual disease of a cancer specified by the predetermined isolated population of cells.

In certain embodiments of such methods, the cancer is a B cell malignancy, while in other embodiments the cancer is multiple myeloma. In certain embodiments of such methods, the cancer is Hodgkin's disease, while in other embodiments the cancer is non-Hodgkin's lymphoma. In certain embodiments of such methods, the cancer is not multiple myeloma. In certain embodiments of such methods, the cancer is not Hodgkin's disease, while in other embodiments the cancer is not non-Hodgkin's lymphoma.

In certain embodiments of such methods, the predetermined population of cells comprise one or more of the following markers: Hoechst (i.e. Hoechst Side Population), CD138$^-$, CD30$^-$, CD3$^-$, CD52$^+$, CD27$^+$, CD20$^+$, and CD19$^+$. While in other embodiments the predetermined population of cells comprise two or more of the following markers: Hoechst (i.e. Hoechst Side Population), CD138$^-$, CD30$^-$, CD3$^-$, CD52$^+$, CD27$^+$, CD20$^+$, and CD19$^+$. While in other embodiments the predetermined population of cells comprise three or more of the following markers: Hoechst (i.e. Hoechst Side Population), CD138$^-$, CD30$^-$, CD3$^-$, CD52$^+$, CD27$^+$, CD20$^+$, and CD19$^+$. While in other embodiments the predetermined population of cells comprise four or more of the following markers: Hoechst (i.e. Hoechst Side Population), CD138$^-$, CD30$^-$, CD3$^-$, CD52$^+$, CD27$^+$, CD20$^+$, and CD19$^+$. While in other embodiments the predetermined population of cells comprise five or more of the following markers: Hoechst (i.e. Hoechst Side Population), CD138$^-$, CD30$^-$, CD3$^-$, CD52$^+$, CD27$^+$, CD20$^+$, and CD19$^+$. While in other embodiments the predetermined population of cells are CD20$^+$. In certain embodiments of such methods, the predetermined population of cells are CD19$^+$, while in other embodiments the predetermined population of cells are CD27$^+$. In certain embodiments of such methods, the predetermined population of cells are Hoechst, while in other embodiments the isolated cells are ALDH$^+$. In certain embodiments of such methods, the predetermined population of cells are CD15$^-$, while in other embodiments the predetermined population of cells are CD30$^-$. In certain embodiments of such methods (e.g., in certain embodiments of leukemia), the predetermined population of cells are CD34$^+$. In other embodiments of such methods (e.g., in certain embodiments of multiple myeloma), the predetermined population of cells are CD34$^-$. In certain embodiments of such methods, the isolated cells are ALDH$^+$, while in other embodiments the isolated cells are CD138$^-$.

In certain embodiments of such methods, the cancer is Hodgkin's Lymphoma (HL) and the cancer stem cells are CD138$^-$/CD19; CD138$^-$/CD20; CD138$^-$/CD27; CD138$^-$/CD15$^-$, CD138$^-$/CD52$^+$ and/or CD138$^-$/CD30$^-$. In certain embodiments of such methods, the cancer is Hodgkin's Lymphoma (HL) and the cancer stem cells are ALDH$^+$/CD138$^-$/CD19$^+$; ALDH$^+$/CD138$^-$/CD20$^+$; ALDH$^+$/CD138$^-$/CD27$^+$; ALDH$^+$/CD138$^-$/CD15$^-$, ALDH$^+$/CD138$^-$/CD52$^+$ and/or ALDH$^+$/CD138$^-$/CD30$^-$. In some embodiments, the cancer is Hodgkin's Lymphoma and the cancer stem cells are CD19$^+$, CD20$^+$, CD27$^+$, CD15$^-$, CD52$^+$ and/or CD30$^-$.

In certain embodiments of such methods, the cancer is Multiple Myeloma and the cancer stem cells are CD138$^-$/CD27; CD138$^-$/CD34$^-$, CD138$^-$/CD19$^+$, CD138$^-$/CD52$^+$ and/or CD138$^-$/CD20$^+$. In certain embodiments of such methods, the cancer is Multiple Myeloma and the cancer stem cells are ALDH$^+$/CD138$^-$/CD27$^+$, ALDH$^+$/CD138$^-$/CD34$^-$, ALDH$^+$/CD138$^-$/CD52$^+$, ALDH$^+$/CD138$^-$/CD19$^+$, and/or ALDH$^+$/CD138$^-$/CD20$^+$. In some embodiments, the cancer is Multiple Myeloma and the cancer stem cells are CD138$^-$, CD27$^+$, CD19$^+$ and/or CD20$^+$.

In certain embodiments of such methods, the cancer is leukemia and the cancer stem cells are CD38$^-$/CD34$^+$. In certain embodiments of such methods, the cancer is leukemia and the cancer stem cells are ALDH$^+$/CD38$^-$/CD34$^+$ and/or ALDH$^+$/CD38$^-$. In some embodiments, the cancer is leukemia and the cancer stem cells are ALDH$^+$/CD34$^+$, ALDH$^+$/CD38$^-$, CD34$^+$ or CD38$^-$.

In certain embodiments of such methods, the cancer is Non Hodgkin's Lymphoma and the cancer stem cells are CD138$^-$/CD19$^+$ and/or CD138$^-$/CD20$^+$. In certain embodiments of such methods, the cancer is Non Hodgkin's Lymphoma and the cancer stem cells are ALDH$^+$/CD138$^-$/CD19$^+$ and/or ALDH$^+$/CD138$^-$/CD20$^+$. In certain embodiments of such methods, the cancer is Non Hodgkin's Lymphoma and the cancer stem cells are ALDH$^+$/CD19$^+$ and/or ALDH$^+$/CD20$^+$.

In certain embodiments the sample is from the patient's blood, while certain embodiments the sample is from the patient's bone marrow.

In various embodiments of such methods, the presence of a high expression of ALDH (ALDH$^{high}$) determines the presence of circulating undifferentiated cells, including circulating cancer stem cells. In other embodiments of such methods, the number of ALDH$^{high}$ cells present is an indication of the minimal residual disease of a cancer specified by the predetermined isolated population of cells. In certain embodiments of such methods, a low number of ALDH$^{high}$ cells present indicate the minimal residual disease of a cancer specified by the predetermined isolated population of cells. In other embodiments of such methods, a high number of ALDH$^{high}$ cells present indicate the minimal residual disease of a cancer specified by the predetermined isolated population of cells.

Determining Efficacy of a Compound to a Cancer

The methods for isolating and identifying circulating undifferentiated cells, including circulating cancer stem cells, disclosed herein can be used for determining/assaying the efficacy of a compound to a cancer. Such methods include the steps of first obtaining a sample from a patient (e.g., a blood sample and/or a bone marrow sample); then isolating a predetermined population of cells from the blood sample using at least one of the separation methods described herein. Such separation methods include, but are not limited to, flow cytometry, fluorescence activated cell sorting, antibody-dependent depletion, antibody-dependent solid phase capture, panning, affinity column separation and magnetic selection. The expression level of ALDH in the isolated predetermined population is then obtained. The presence of a high expression of ALDH (ALDH$^{high}$) is used to determine the presence of circulating undifferentiated cells, including circulating cancer stem cells. The number of (ALDH$^{high}$) cells present is an indication of the efficacy of the compound towards a cancer specified by the predetermined isolated population of cells.

In certain embodiments of such methods, the cancer is a B cell malignancy, while in other embodiments the cancer is multiple myeloma. In certain embodiments of such methods, the cancer is Hodgkin's disease, while in other embodiments the cancer is non-Hodgkin's lymphoma. In certain embodiments of such methods, the cancer is not multiple myeloma. In certain embodiments of such methods, the cancer is not Hodgkin's disease, while in other embodiments the cancer is not non-Hodgkin's lymphoma.

In certain embodiments of such methods, the predetermined population of cells comprise one or more of the following markers: Hoechst (i.e. Hoechst Side Population), CD138$^-$, CD30$^-$, CD3$^-$, CD52$^+$, CD27$^+$, CD20$^+$, and CD19$^+$. While in other embodiments the predetermined population of cells comprise two or more of the following markers: Hoechst (i.e. Hoechst Side Population), CD138$^-$, CD30$^-$, CD3$^-$, CD52$^+$, CD27$^+$, CD20$^+$, and CD19$^+$. While in other embodiments the predetermined population of cells comprise three or more of the following markers: Hoechst (i.e. Hoechst Side Population), CD138$^-$, CD30$^-$, CD3$^-$, CD52$^+$, CD27$^+$, CD20$^+$, and CD19$^+$. While in other embodiments the predetermined population of cells comprise four or more of the following markers: Hoechst (i.e. Hoechst Side Population), CD138$^-$, CD30$^-$, CD3$^-$, CD52$^+$, CD27$^+$, CD20$^+$, and CD19$^+$. While in other embodiments the predetermined population of cells comprise five or more of the following markers: Hoechst (i.e. Hoechst Side Population), CD138$^-$, CD30$^-$, CD3$^-$, CD52$^+$, CD27$^+$, CD20$^+$, and CD19$^+$. While in other embodiments the predetermined population of cells are CD20$^+$. In certain embodiments of such methods, the predetermined population of cells are CD19$^+$, while in other embodiments the predetermined population of cells are CD27$^+$. In certain embodiments of such methods, the predetermined population of cells are Hoechst, while in other embodiments the isolated cells are ALDH$^+$. In certain embodiments of such methods, the predetermined population of cells are CD15$^-$, while in other embodiments the predetermined population of cells are CD30$^-$. In certain embodiments of such methods (e.g., in certain embodiments of leukemia), the predetermined population of cells are CD34$^+$. In other embodiments of such methods (e.g., in certain embodiments of multiple myeloma), the predetermined population of cells are CD34$^-$. In certain embodiments of such methods, the isolated cells are ALDH$^+$, while in other embodiments the isolated cells are CD38$^-$ or CD138$^+$.

In certain embodiments of such methods, the cancer is Hodgkin's Lymphoma (HL) and the cancer stem cells are CD138$^-$/CD19$^+$; CD138$^-$/CD20; CD138$^-$/CD27$^+$; CD138$^-$/CD15$^-$, CD138$^-$/CD52$^+$ and/or CD138$^-$/CD30$^-$. In certain embodiments of such methods, the cancer is Hodgkin's Lymphoma (HL) and the cancer stem cells are ALDH$^+$/CD138$^-$/CD19$^+$; ALDH$^+$/CD138$^-$/CD20$^+$; ALDH$^+$/CD138$^-$/CD27$^+$; ALDH$^+$/CD138$^-$/CD15$^-$, ALDH$^+$/CD138$^-$/CD52$^+$ and/or ALDH$^+$/CD138$^-$/CD30$^-$. In some embodiments, the cancer is Hodgkin's Lymphoma and the cancer stem cells are CD19$^+$, CD20$^+$, CD27$^+$, CD15$^-$, CD52$^+$ and/or CD30$^-$.

In certain embodiments of such methods, the cancer is Multiple Myeloma and the cancer stem cells are CD138$^-$/CD27$^+$; CD138$^-$/CD34$^-$, CD138$^-$/CD19$^+$, CD138$^-$/CD52$^+$ and/or CD138$^-$/CD20$^+$. In certain embodiments of such methods, the cancer is Multiple Myeloma and the cancer stem cells are ALDH$^+$/CD138$^-$/CD27$^+$, ALDH$^+$/CD138$^-$/CD34$^-$, ALDH$^+$/CD138$^-$/CD52$^+$, ALDH$^+$/CD138$^-$/CD19$^+$, and/or ALDH$^+$/CD138$^-$/CD20$^+$. In some embodiments, the cancer is Multiple Myeloma and the cancer stem cells are CD138$^-$, CD27$^+$, CD19$^+$ and/or CD20$^+$.

In certain embodiments of such methods, the cancer is leukemia and the cancer stem cells are CD38$^-$/CD34$^+$. In certain embodiments of such methods, the cancer is leukemia and the cancer stem cells are ALDH$^+$/CD38$^-$/CD34$^+$ and/or ALDH$^+$/CD38$^-$. In some embodiments, the cancer is leukemia and the cancer stem cells are ALDH$^+$/CD34$^+$, ALDH$^+$/CD38$^-$, CD34$^+$ or CD38$^-$.

In certain embodiments of such methods, the cancer is Non Hodgkin's Lymphoma and the cancer stem cells are CD138⁻/CD19⁺ and/or CD138⁻/CD20⁺. In certain embodiments of such methods, the cancer is Non Hodgkin's Lymphoma and the cancer stem cells are ALDH⁺/CD138⁻/CD19⁺ and/or ALDH⁺/CD138⁻/CD20⁺. In certain embodiments of such methods, the cancer is Non Hodgkin's Lymphoma and the cancer stem cells are ALDH⁺/CD19⁺ and/or ALDH⁺/CD20⁺.

In certain embodiments the sample is from the patient's blood, while certain embodiments the sample is from the patient's bone marrow.

In certain embodiments of such methods, the presence of a high expression of ALDH (ALDH$^{high}$) is used to determine the presence of circulating undifferentiated cells, including circulating cancer stem cells. In other embodiments of such methods, the number of ALDH$^{high}$ cells present is an indication of the efficacy of the compound towards a cancer specified by the predetermined isolated population of cells. In other embodiments of such methods, a low number of ALDH$^{high}$ cells present indicate the efficacy of the compound towards a cancer specified by the predetermined isolated population of cells. In other embodiments of such methods, a high number of ALDH$^{high}$ cells present indicates the efficacy of the compound towards a cancer specified by the predetermined isolated population of cells.

Staging a Patient

The methods for isolating and identifying circulating undifferentiated cells, including circulating cancer stem cells, disclosed herein can be used for staging a patient diagnosed with a cancer. Such methods include the steps of first obtaining a sample from a patient (e.g., a blood sample and/or a bone marrow sample); then isolating a predetermined population of cells from the blood sample using at least one of the separation methods described herein. Such separation methods include, but are not limited to, flow cytometry, fluorescence activated cell sorting, antibody-dependent depletion, antibody-dependent solid phase capture, panning, affinity column separation and magnetic selection. The expression level of ALDH in the isolated predetermined population is then obtained. The presence of a high expression of ALDH (ALDH$^{high}$) is used to determine the presence of circulating undifferentiated cells, including circulating cancer stem cells.

The number of undifferentiated cancer cells, as indicated by the number of (ALDH$^{high}$) cells, present in the predetermined isolated population of cells is then determined. In certain embodiments, the stage of the cancer is indicated by the number of stem cells between 1-50,000 stem cells per ml of blood. In certain embodiments, the stage of the cancer is indicated by the number of stem cells between 1-40,000 stem cells per ml of blood. In certain embodiments, the stage of the cancer is indicated by the number of stem cells between 1-30,000 stem cells per ml of blood. In certain embodiments, the stage of the cancer is indicated by the number of stem cells between 1-20,000 stem cells per ml of blood. In certain embodiments, the stage of the cancer is indicated by the number of stem cells between 1-10,000 stem cells per ml of blood. In certain embodiments, the stage of the cancer is indicated by the number of stem cells between 1-5000 stem cells per ml of blood. In certain embodiments, the stage of the cancer is indicated by the number of stem cells between 1-1000 stem cells per ml of blood. In certain embodiments, the stage of the cancer is indicated by the number of stem cells between 1-500 stem cells per ml of blood. In certain embodiments, the stage of the cancer is indicated by the number of stem cells between 1-100 stem cells per ml of blood.

In certain embodiments, the method also includes the step of comparing the number of stem cells (i.e. ALDH$^{high}$ cells) present in the isolated population to a predetermined level of stem cells, wherein the predetermined level indicates the extent or severity of cancer in a patient. In certain embodiments, predetermined level of stem cells is 50,000 stem cells per ml of blood. In certain embodiments, predetermined level of stem cells is 40,000 stem cells per ml of blood. In certain embodiments, predetermined level of stem cells is 30,000 stem cells per ml of blood. In certain embodiments, predetermined level of stem cells is 20,000 stem cells per ml of blood. In certain embodiments, predetermined level of stem cells is 10,000 stem cells per ml of blood. In certain embodiments, predetermined level of stem cells is 5000 stem cells per ml of blood. In certain embodiments, predetermined level of stem cells is 1000 stem cells per ml of blood. In certain embodiments, predetermined level of stem cells is 500 stem cells per ml of blood. In certain embodiments, predetermined level of stem cells is 100 stem cells stem cells per ml of blood.

In certain embodiments of such methods the number of undifferentiated cancer cells is determined using flow cytometry, while in other embodiments the number of undifferentiated cancer cells is determined using a fluorescence activated cell sorter (FACS).

In certain embodiments of such methods, the cancer is a B cell malignancy, while in other embodiments the cancer is multiple myeloma. In certain embodiments of such methods, the cancer is Hodgkin's disease, while in other embodiments the cancer is non-Hodgkin's lymphoma. In certain embodiments of such methods, the cancer is not multiple myeloma. In certain embodiments of such methods, the cancer is not Hodgkin's disease, while in other embodiments the cancer is not non-Hodgkin's lymphoma.

In certain embodiments of such methods, the predetermined population of cells comprise one or more of the following markers: Hoechst (i.e. Hoechst Side Population), CD138⁻, CD30⁻, CD3⁻, CD52⁺, CD27⁺, CD20⁺, and CD19⁺. While in other embodiments the predetermined population of cells comprise two or more of the following markers: Hoechst (i.e. Hoechst Side Population), CD138⁻, CD30⁻, CD3⁻, CD52⁺, CD27⁺, CD20⁺, and CD19⁺. While in other embodiments the predetermined population of cells comprise three or more of the following markers: Hoechst (i.e. Hoechst Side Population), CD138⁻, CD30⁻, CD3⁻, CD52⁺, CD27⁺, CD20⁺, and CD19⁺. While in other embodiments the predetermined population of cells comprise four or more of the following markers: Hoechst (i.e. Hoechst Side Population), CD138⁻, CD30⁻, CD3⁻, CD52⁺, CD27⁺, CD20⁺, and CD19⁺. While in other embodiments the predetermined population of cells comprise five or more of the following markers: Hoechst (i.e. Hoechst Side Population), CD138⁻, CD30⁻, CD3⁻, CD52⁺, CD27⁺, CD20⁺, and CD19⁺. While in other embodiments the predetermined population of cells are CD20⁺. In certain embodiments of such methods, the predetermined population of cells are CD19⁺, while in other embodiments the predetermined population of cells are CD27⁺. In certain embodiments of such methods, the predetermined population of cells are Hoechst⁻, while in other embodiments the isolated cells are ALDH⁺. In certain embodiments of such methods, the predetermined population of cells are CD15⁻, while in other embodiments the predetermined population of cells are CD30⁻. In certain embodiments of such methods (e.g., in certain embodiments of leukemia), the predetermined population of cells are CD34⁺. In other embodiments of such methods (e.g., in certain embodiments of multiple myeloma), the predetermined population of cells are CD34⁻. In certain embodiments of such methods, the isolated cells are ALDH⁺, while in other embodiments the isolated cells are CD138⁻ or CD38⁻.

In certain embodiments of such methods, the cancer is Hodgkin's Lymphoma (HL) and the cancer stem cells are CD138$^-$/CD19; CD138$^-$/CD20; CD138$^-$/CD27; CD138$^-$/CD15$^-$, CD138$^-$/CD52$^+$ and/or CD138$^-$/CD30$^-$. In certain embodiments of such methods, the cancer is Hodgkin's Lymphoma (HL) and the cancer stem cells are ALDH$^+$/CD138$^-$/CD19$^+$; ALDH$^+$/CD138$^-$/CD20$^+$; ALDH$^+$/CD138$^-$/CD27$^+$; ALDH$^+$/CD138$^-$/CD15$^-$, ALDH$^+$/CD138$^-$/CD52$^+$ and/or ALDH$^+$/CD138$^-$/CD30$^-$. In some embodiments, the cancer is Hodgkin's Lymphoma and the cancer stem cells are CD19$^+$, CD20$^+$, CD27$^+$, CD15$^-$, CD52$^+$ and/or CD30$^-$.

In certain embodiments of such methods, the cancer is Multiple Myeloma and the cancer stem cells are CD138$^-$/CD27; CD138$^-$/CD34$^-$, CD138$^-$/CD19$^+$, CD138$^-$/CD52$^+$ and/or CD138$^-$/CD20$^+$. In certain embodiments of such methods, the cancer is Multiple Myeloma and the cancer stem cells are ALDH$^+$/CD138$^-$/CD27$^+$, ALDH$^+$/CD138$^-$/CD34$^-$, ALDH$^+$/CD138$^-$/CD52$^+$, ALDH$^+$/CD138$^-$/CD19$^+$, and/or ALDH$^+$/CD138$^-$/CD20$^+$. In some embodiments, the cancer is Multiple Myeloma and the cancer stem cells are CD138$^-$, CD27$^+$, CD19$^+$ and/or CD20$^+$.

In certain embodiments of such methods, the cancer is leukemia and the cancer stem cells are CD38$^-$/CD34$^+$. In certain embodiments of such methods, the cancer is leukemia and the cancer stem cells are ALDH$^+$/CD38$^-$/CD34$^+$ and/or ALDH$^+$/CD38$^-$. In some embodiments, the cancer is leukemia and the cancer stem cells are ALDH$^+$/CD34$^+$, ALDH$^+$/CD38$^-$, CD34$^+$ or CD38$^-$.

In certain embodiments of such methods, the cancer is Non Hodgkin's Lymphoma and the cancer stem cells are CD138$^-$/CD19$^+$ and/or CD138$^-$/CD20$^+$. In certain embodiments of such methods, the cancer is Non Hodgkin's Lymphoma and the cancer stem cells are ALDH$^+$/CD138$^-$/CD19$^+$ and/or ALDH$^+$/CD138$^-$/CD20$^+$. In certain embodiments of such methods, the cancer is Non Hodgkin's Lymphoma and the cancer stem cells are ALDH$^+$/CD19$^+$ and/or ALDH$^+$/CD20$^+$.

In certain embodiments the sample is from the patient's blood, while certain embodiments the sample is from the patient's bone marrow.

In various embodiments of such methods, the presence of a high expression of ALDH (ALDH$^{high}$) determines the presence of circulating undifferentiated cells, including circulating cancer stem cells. In other embodiments of such methods, the number of ALDH$^{high}$ cells present is an indication of the minimal residual disease of a cancer specified by the predetermined isolated population of cells. In certain embodiments of such methods, a low number of ALDH$^{high}$ cells present indicate the minimal residual disease of a cancer specified by the predetermined isolated population of cells. In other embodiments of such methods, a high number of ALDH$^{high}$ cells present indicate the minimal residual disease of a cancer specified by the predetermined isolated population of cells.

Monitoring a Cancer Patient

The methods for isolating and identifying circulating undifferentiated cells, including circulating cancer stem cells, disclosed herein can be used for monitoring the presence of a cancer in a patient. Such methods include the steps of (a) obtaining a sample from the patient;
(b) isolating a predetermined population of cells from the blood sample;
(c) determining the number of undifferentiated cancer cells present in the isolated population of cells;
(d) repeating steps (a) through (c) at least one time; and
(e) comparing the results.

The predetermined population can be isolated using cell separation methods including, but are not limited to, flow cytometry, fluorescence activated cell sorting, antibody-dependent depletion, antibody-dependent solid phase capture, panning, affinity column separation and magnetic selection. The expression level of ALDH in the isolated predetermined population is then obtained. The presence of a high expression of ALDH (ALDH$^{high}$) is used to determine the presence and number of circulating undifferentiated cells, including circulating cancer stem cells. The number of undifferentiated cancer cells, as indicated by the number of (ALDH$^{high}$) cells, present in the predetermined isolated population of cells is then determined and compared.

In certain embodiments of such methods, the cancer is a B cell malignancy, while in other embodiments the cancer is multiple myeloma. In certain embodiments of such methods, the cancer is Hodgkin's disease, while in other embodiments the cancer is non-Hodgkin's lymphoma. In certain embodiments of such methods, the cancer is not multiple myeloma. In certain embodiments of such methods, the cancer is not Hodgkin's disease, while in other embodiments the cancer is not non-Hodgkin's lymphoma.

In certain embodiments of such methods, the predetermined population of cells comprise one or more of the following markers: Hoechst (i.e. Hoechst Side Population), CD138$^-$, CD30$^-$, CD3$^-$, CD52$^+$, CD27$^+$, CD20$^+$, and CD19$^+$. While in other embodiments the predetermined population of cells comprise two or more of the following markers: Hoechst (i.e. Hoechst Side Population), CD138$^-$, CD30$^-$, CD3$^-$, CD52$^+$, CD27$^+$, CD20$^+$, and CD19$^+$. While in other embodiments the predetermined population of cells comprise three or more of the following markers: Hoechst (i.e. Hoechst Side Population), CD138$^-$, CD30$^-$, CD3$^-$, CD52$^+$, CD27$^+$, CD20$^+$, and CD19$^+$. While in other embodiments the predetermined population of cells comprise four or more of the following markers: Hoechst (i.e. Hoechst Side Population), CD138$^-$, CD30$^-$, CD3$^-$, CD52$^+$, CD27$^+$, CD20$^+$, and CD19$^+$. While in other embodiments the predetermined population of cells comprise five or more of the following markers: Hoechst (i.e. Hoechst Side Population), CD138$^-$, CD30$^-$, CD3$^-$, CD52$^+$, CD27$^+$, CD20$^+$, and CD19$^+$. While in other embodiments the predetermined population of cells are CD20$^+$. In certain embodiments of such methods, the predetermined population of cells are CD19$^+$, while in other embodiments the predetermined population of cells are CD27$^+$. In certain embodiments of such methods, the predetermined population of cells are Hoechst, while in other embodiments the isolated cells are ALDH$^+$. In certain embodiments of such methods, the predetermined population of cells are CD15$^-$, while in other embodiments the predetermined population of cells are CD30$^-$. In certain embodiments of such methods (e.g., in certain embodiments of leukemia), the predetermined population of cells are CD34$^+$. In other embodiments of such methods (e.g., in certain embodiments of multiple myeloma), the predetermined population of cells are CD34$^-$. In certain embodiments of such methods, the isolated cells are ALDH$^+$, while in other embodiments the isolated cells are CD138$^-$ or CD38$^-$.

In certain embodiments of such methods, the cancer is Hodgkin's Lymphoma (HL) and the cancer stem cells are CD138$^-$/CD19$^+$; CD138$^-$/CD20$^+$; CD138$^-$/CD27$^+$; CD138$^-$/CD15$^-$, CD138$^-$/CD52$^+$ and/or CD138$^-$/CD30$^-$. In certain embodiments of such methods, the cancer is Hodgkin's Lymphoma (HL) and the cancer stem cells are ALDH$^+$/CD138$^-$/CD19$^+$; ALDH$^+$/CD138$^-$/CD20$^+$; ALDH$^+$/CD138$^-$/CD27$^+$; ALDH$^+$/CD138$^-$/CD15$^-$, ALDH$^+$/CD138$^-$/CD52$^+$ and/or ALDH$^+$/CD138$^-$/CD30$^-$. In some embodiments, the cancer is Hodgkin's Lymphoma and the cancer stem cells are CD19$^+$, CD20$^+$, CD27$^+$, CD15$^-$, CD52$^+$ and/or CD30$^-$.

In certain embodiments of such methods, the cancer is Multiple Myeloma and the cancer stem cells are CD138$^-$/CD27$^+$; CD138$^-$/CD34$^-$, CD138$^-$/CD19$^+$, CD138$^-$/CD52$^+$ and/or CD138$^-$/CD20$^+$. In certain embodiments of such methods, the cancer is Multiple Myeloma and the cancer stem cells are ALDH$^+$/CD138$^-$/CD27$^+$, ALDH$^+$/CD138$^-$/CD34$^-$, ALDH$^+$/CD138$^-$/CD52$^+$, ALDH$^+$/CD138$^-$/CD19$^+$, and/or ALDH$^+$/CD138$^-$/CD20$^+$. In some embodiments, the cancer is Multiple Myeloma and the cancer stem cells are CD138$^-$, CD27$^+$, CD19$^+$ and/or CD20$^+$.

In certain embodiments of such methods, the cancer is leukemia and the cancer stem cells are CD138$^-$/CD34$^+$ and/or CD138$^-$/CD38$^-$. In certain embodiments of such methods, the cancer is leukemia and the cancer stem cells are ALDH$^+$/CD38$^-$/CD34$^+$ and/or ALDH$^+$/CD38$^-$. In some embodiments, the cancer is leukemia and the cancer stem cells are ALDH$^+$/CD34$^+$, ALDH$^+$/CD38$^-$, CD34$^+$ or CD38$^-$.

In certain embodiments of such methods, the cancer is Non Hodgkin's Lymphoma and the cancer stem cells are CD138$^-$/CD19$^+$ and/or CD138$^-$/CD20$^+$. In certain embodiments of such methods, the cancer is Non Hodgkin's Lymphoma and the cancer stem cells are ALDH$^+$/CD138$^-$/CD19$^+$ and/or ALDH$^+$/CD138$^-$/CD20$^+$. In certain embodiments of such methods, the cancer is Non Hodgkin's Lymphoma and the cancer stem cells are ALDH$^+$/CD19$^+$ and/or ALDH$^+$/CD20$^+$.

In certain embodiments the sample is from the patient's blood, while certain embodiments the sample is from the patient's bone marrow.

In certain embodiments of such methods the number of high expression of ALDH (ALDH$^{high}$) decreases when compared to an earlier result. In certain embodiments of such methods the number of high expression of ALDH (ALDH$^{high}$) increases when compared to an earlier result. In certain embodiments of such methods the number of high expression of ALDH (ALDH$^{high}$) remains the same when compared to an earlier result.

Isolating and/or Identifying a Subpopulation of Cells

The methods for isolating and identifying circulating undifferentiated cells, including circulating cancer stem cells, disclosed herein can be used for identifying a sub-population of undifferentiated cells, including cancer stem cells, in a sample. Such methods include the steps of first obtaining a sample from a patient (e.g., a blood sample and/or a bone marrow sample); then isolating a predetermined population of cells from the blood sample using at least one of the separation methods described herein. Such separation methods include, but are not limited to, flow cytometry, fluorescence activated cell sorting, antibody-dependent depletion, antibody-dependent solid phase capture, panning, affinity column separation and magnetic selection.

The methods for isolating and identifying circulating undifferentiated cells, including circulating cancer stem cells, disclosed herein can be used to obtain an isolated subpopulation of circulating undifferentiated cells. Such methods include the steps of first obtaining a sample from a patient (e.g., a blood sample and/or a bone marrow sample); then isolating a predetermined population of cells from the blood sample using at least one of the separation methods described herein.

In certain embodiments of such methods, the cancer is a B cell malignancy, while in other embodiments the cancer is multiple myeloma. In certain embodiments of such methods, the cancer is Hodgkin's disease, while in other embodiments the cancer is non-Hodgkin's lymphoma. In certain embodiments of such methods, the cancer is not multiple myeloma. In certain embodiments of such methods, the cancer is not Hodgkin's disease, while in other embodiments the cancer is not non-Hodgkin's lymphoma.

In certain embodiments of such methods, the predetermined population of cells comprise one or more of the following markers: Hoechst (i.e. Hoechst Side Population), CD138$^-$, CD30$^-$, CD3$^-$, CD52$^+$, CD27$^+$, CD20$^+$, and CD19$^+$. While in other embodiments the predetermined population of cells comprise two or more of the following markers: Hoechst (i.e. Hoechst Side Population), CD138$^-$, CD30$^-$, CD3$^-$, CD52$^+$, CD27$^+$, CD20$^+$, and CD19$^+$. While in other embodiments the predetermined population of cells comprise three or more of the following markers: Hoechst (i.e. Hoechst Side Population), CD138$^-$, CD30$^-$, CD3$^-$, CD52$^+$, CD27$^+$, CD20$^+$, and CD19$^+$. While in other embodiments the predetermined population of cells comprise four or more of the following markers: Hoechst (i.e. Hoechst Side Population), CD138$^-$, CD30$^-$, CD3$^-$, CD52$^+$, CD27$^+$, CD20$^+$, and CD19$^+$. While in other embodiments the predetermined population of cells comprise five or more of the following markers: Hoechst (i.e. Hoechst Side Population), CD138$^-$, CD30$^-$, CD3$^-$, CD52$^+$, CD27$^+$, CD20$^+$, and CD19$^+$. While in other embodiments the predetermined population of cells are CD20$^+$. In certain embodiments of such methods, the predetermined population of cells are CD19$^+$, while in other embodiments the predetermined population of cells are CD27$^+$. In certain embodiments of such methods, the predetermined population of cells are Hoechst, while in other embodiments the isolated cells are ALDH$^+$. In certain embodiments of such methods, the predetermined population of cells are CD15$^-$, while in other embodiments the predetermined population of cells are CD30$^-$. In certain embodiments of such methods (e.g., in certain embodiments of leukemia), the predetermined population of cells are CD34$^+$. In other embodiments of such methods (e.g., in certain embodiments of multiple myeloma), the predetermined population of cells are CD34$^-$. In certain embodiments of such methods, the isolated cells are ALDH$^+$, while in other embodiments the isolated cells are CD138$^-$ or CD38$^-$.

In certain embodiments of such methods, the cancer is Hodgkin's Lymphoma (HL) and the cancer stem cells are CD138$^-$/CD19; CD138$^-$/CD20; CD138$^-$/CD27; CD138$^-$/CD15$^-$, CD138$^-$/CD52$^+$ and/or CD138$^-$/CD30$^-$. In certain embodiments of such methods, the cancer is Hodgkin's Lymphoma (HL) and the cancer stem cells are ALDH$^+$/CD138$^-$/CD19$^+$; ALDH$^+$/CD138$^-$/CD20$^+$; ALDH$^+$/CD138$^-$/CD27$^+$; ALDH$^+$/CD138$^-$/CD15$^-$, ALDH$^+$/CD138$^-$/CD52$^+$ and/or ALDH$^+$/CD138$^-$/CD30$^-$. In some embodiments, the cancer is Hodgkin's Lymphoma and the cancer stem cells are CD19$^+$, CD20$^+$, CD27$^+$, CD15$^-$, CD52$^+$ and/or CD30$^-$.

In certain embodiments of such methods, the cancer is Multiple Myeloma and the cancer stem cells are CD138$^-$/CD27$^+$; CD138$^-$/CD34$^-$, CD138$^-$/CD19$^+$, CD138$^-$/CD52$^+$ and/or CD138$^-$/CD20$^+$. In certain embodiments of such methods, the cancer is Multiple Myeloma and the cancer stem cells are ALDH$^+$/CD138$^-$/CD27$^+$, ALDH$^+$/CD138$^-$/CD34$^-$, ALDH$^+$/CD138$^-$/CD52$^+$, ALDH$^+$/CD138$^-$/CD19$^+$, and/or ALDH$^+$/CD138$^-$/CD20$^+$. In some embodiments, the cancer is Multiple Myeloma and the cancer stem cells are CD138$^-$, CD27$^+$, CD19$^+$ and/or CD20$^+$.

In certain embodiments of such methods, the cancer is leukemia and the cancer stem cells are CD38$^-$/CD34$^+$ and/or CD38$^-$. In certain embodiments of such methods, the cancer is leukemia and the cancer stem cells are ALDH$^+$/CD38$^-$/CD34$^+$ and/or ALDH$^+$/CD38$^-$. In some embodiments, the cancer is leukemia and the cancer stem cells are ALDH$^+$/CD34$^+$, ALDH$^+$/CD38$^-$, CD34$^+$ or CD38$^-$.

In certain embodiments of such methods, the cancer is Non Hodgkin's Lymphoma and the cancer stem cells are CD138$^-$/CD19$^+$ and/or CD138$^-$/CD20$^+$. In certain embodiments of such methods, the cancer is Non Hodgkin's Lymphoma and the cancer stem cells are ALDH$^+$/CD138$^-$/CD19$^+$ and/or ALDH$^+$/CD138$^-$/CD20$^+$. In certain embodiments of such methods, the cancer is Non Hodgkin's Lymphoma and the cancer stem cells are ALDH$^+$/CD19$^+$ and/or ALDH$^+$/CD20$^+$.

In certain embodiments the sample is from the patient's blood, while certain embodiments the sample is from the patient's bone marrow.

Selecting a Cancer Patient

The methods for isolating and identifying circulating undifferentiated cells, including circulating cancer stem cells, disclosed herein can be used to select a cancer patient who is predicted to benefit from the administration of a chemotherapeutic. Such methods include the steps of first obtaining a sample from a patient (e.g., a blood sample and/or a bone marrow sample); then isolating a predetermined population of cells from the blood sample using at least one of the separation methods described herein. Such separation methods include, but are not limited to, flow cytometry, fluorescence activated cell sorting, antibody-dependent depletion, antibody-dependent solid phase capture, panning, affinity column separation and magnetic selection. The expression level of ALDH in the isolated population is then determined and used to predict the therapeutic benefit for the administration of a chemotherapeutic. Patients having cells with high ALDH (ALDH$^{high}$) expression levels are predicted to benefit from the administration of the chemotherapeutic.

In certain embodiments of such methods, the cancer is a B cell malignancy, while in other embodiments the cancer is multiple myeloma. In certain embodiments of such methods, the cancer is Hodgkin's disease, while in other embodiments the cancer is non-Hodgkin's lymphoma. In certain embodiments of such methods, the cancer is not multiple myeloma. In certain embodiments of such methods, the cancer is not Hodgkin's disease, while in other embodiments the cancer is not non-Hodgkin's lymphoma.

In certain embodiments of such methods, the predetermined population of cells comprise one or more of the following markers: Hoechst (i.e. Hoechst Side Population), CD138$^-$, CD30$^-$, CD3$^-$, CD52$^+$, CD27$^+$, CD20$^+$, and CD19$^+$. While in other embodiments the predetermined population of cells comprise two or more of the following markers: Hoechst (i.e. Hoechst Side Population), CD138$^-$, CD30$^-$, CD3$^-$, CD52$^+$, CD27$^+$, CD20$^+$, and CD19$^+$. While in other embodiments the predetermined population of cells comprise three or more of the following markers: Hoechst (i.e. Hoechst Side Population), CD138$^-$, CD30$^-$, CD3$^-$, CD52$^+$, CD27$^+$, CD20$^+$, and CD19$^+$. While in other embodiments the predetermined population of cells comprise four or more of the following markers: Hoechst (i.e. Hoechst Side Population), CD138$^-$, CD30$^-$, CD3$^-$, CD52$^+$, CD27$^+$, CD20$^+$, and CD19$^+$. While in other embodiments the predetermined population of cells comprise five or more of the following markers: Hoechst (i.e. Hoechst Side Population), CD138$^-$, CD30$^-$, CD3$^-$, CD52$^+$, CD27$^+$, CD20$^+$, and CD19$^+$. While in other embodiments the predetermined population of cells are CD20$^+$. In certain embodiments of such methods, the predetermined population of cells are CD19$^+$, while in other embodiments the predetermined population of cells are CD27$^+$. In certain embodiments of such methods, the predetermined population of cells are Hoechst, while in other embodiments the isolated cells are ALDH$^+$. In certain embodiments of such methods, the predetermined population of cells are CD15$^-$, while in other embodiments the predetermined population of cells are CD30$^-$. In certain embodiments of such methods (e.g., in certain embodiments of leukemia), the predetermined population of cells are CD34$^+$. In other embodiments of such methods (e.g., in certain embodiments of multiple myeloma), the predetermined population of cells are CD34$^-$. In certain embodiments of such methods, the isolated cells are ALDH$^+$, while in other embodiments the isolated cells are CD138$^-$ or CD38$^-$.

In certain embodiments of such methods, the cancer is Hodgkin's Lymphoma (HL) and the cancer stem cells are CD138$^-$/CD19; CD138$^-$/CD20; CD138$^-$/CD27; CD138$^-$/CD15$^-$, CD138$^-$/CD52$^+$ and/or CD138$^-$/CD30$^-$. In certain embodiments of such methods, the cancer is Hodgkin's Lymphoma (HL) and the cancer stem cells are ALDH$^+$/CD138$^-$/CD19$^+$; ALDH$^+$/CD138$^-$/CD20$^+$; ALDH$^+$/CD138$^-$/CD27$^+$; ALDH$^+$/CD138$^-$/CD15$^-$, ALDH$^+$/CD138$^-$/CD52$^+$ and/or ALDH$^+$/CD138$^-$/CD30$^-$. In some embodiments, the cancer is Hodgkin's Lymphoma and the cancer stem cells are CD19$^+$, CD20$^+$, CD27$^+$, CD15$^-$, CD52$^+$ and/or CD30$^-$.

In certain embodiments of such methods, the cancer is Multiple Myeloma and the cancer stem cells are CD138$^-$/CD27; CD138$^-$/CD34$^-$, CD138$^-$/CD19$^+$, CD138$^-$/CD52$^+$ and/or CD138$^-$/CD20$^+$. In certain embodiments of such methods, the cancer is Multiple Myeloma and the cancer stem cells are ALDH$^+$/CD138$^-$/CD27$^+$, ALDH$^+$/CD138$^-$/CD34$^-$, ALDH$^+$/CD138$^-$/CD52$^+$, ALDH$^+$/CD138$^-$/CD19$^+$, and/or ALDH$^+$/CD138$^-$/CD20$^+$. In some embodiments, the cancer is Multiple Myeloma and the cancer stem cells are CD138$^-$, CD27$^+$, CD19$^+$ and/or CD20$^+$.

In certain embodiments of such methods, the cancer is leukemia and the cancer stem cells are CD38$^-$/CD34$^+$ and/or CD38$^-$. In certain embodiments of such methods, the cancer is leukemia and the cancer stem cells are ALDH$^+$/CD38$^-$/CD34$^+$ and/or ALDH$^+$/CD38$^-$. In some embodiments, the cancer is leukemia and the cancer stem cells are ALDH$^+$/CD34$^+$, ALDH$^+$/CD38$^-$, CD34$^+$ or CD38$^-$.

In certain embodiments of such methods, the cancer is Non Hodgkin's Lymphoma and the cancer stem cells are CD138$^-$/CD19$^+$ and/or CD138$^-$/CD20$^+$. In certain embodiments of such methods, the cancer is Non Hodgkin's Lymphoma and the cancer stem cells are ALDH$^+$/CD138$^-$/CD19$^+$ and/or ALDH$^+$/CD138$^-$/CD20$^+$. In certain embodiments of such methods, the cancer is Non Hodgkin's Lymphoma and the cancer stem cells are ALDH$^+$/CD19$^+$ and/or ALDH$^+$/CD20$^+$.

In certain embodiments the sample is from the patient's blood, while certain embodiments the sample is from the patient's bone marrow.

In certain embodiments of such methods the chemotherapeutic is a cytotoxic agent, an antiproliferative, a targeting agent, a biologic agent, or combination thereof. In certain embodiments the targeting agent is a kinase inhibitor or cell cycle regulator. In certain embodiments the biologic agent is a cytokine, vaccine, viral agent or immunostimulant, while in other embodiments the immunostimulant is a BCG, hormone, monoclonal antibody or siRNA. In certain embodiments of such methods, the chemotherapeutic is an HDAC inhibitor.

In certain embodiments of such methods, the cancer treatment is a stem-cell targeted therapy, while in other embodiments the cancer treatment involves induction of terminal differentiation. In certain embodiments of such methods, the cancer treatment involves inhibition of telomerase, while in other embodiments the cancer treatment involves inhibition of developmental signaling pathways. In certain embodiments of such methods, the cancer treatment involves inhibition of intracellular signal transduction pathways, while in other embodiments the cancer treatment involves induction of active immunity to cellular antigens. In certain embodiments of such methods, the cancer treatment involves induction of passive immunity to cellular antigens. In certain embodiments of such methods the chemotherapeutic is a hedgehog inhibitor, while in other embodiments the chemotherapeutic is a telomerase inhibitor. In certain embodiments the chemotherapeutic is rituximab. In certain embodiments the chemotherapeutic is alemtuzumab.

In certain embodiments of such methods, a high expression level of ALDH in the isolated population predicts a therapeutic benefit for the administration of a chemotherapeutic, while in other embodiments of such methods, a high expression level of ALDH in the isolated population predicts no therapeutic benefit for the administration of a chemotherapeutic. In certain embodiments of such methods, a low expression level of ALDH in the isolated population predicts a therapeutic benefit for the administration of a chemotherapeutic, while in other embodiments of such methods, a low expression level of ALDH in the isolated population predicts no therapeutic benefit for the administration of a chemotherapeutic.

Methods of Treatment

The methods for isolating and identifying circulating undifferentiated cells, including circulating cancer stem cells, disclosed herein can be used in a method to treating cancer in a patient wherein at least one circulating cancer stem cell has been identified. Such treatment methods include the steps of detecting a circulating cancer stem cell and optionally determining the ALDH expression level of such cancer stem cells, identifying the cancer; and contacting the circulating cancer stem cell with a therapeutically effective amount of a chemotherapeutic. In certain embodiments the expression level of ALDH is used to predict the therapeutic benefit for the administration of the chemotherapeutic. Patients having cells with high ALDH (ALDH$^{high}$) expression levels are predicted to benefit from the administration of the chemotherapeutic.

In such treatment methods, the detecting of circulating cancer stem cells involves first obtaining a sample from a patient (e.g., a blood sample and/or a bone marrow sample); then isolating a predetermined population of cells from the blood sample using at least one of the separation methods described herein. Such separation methods include, but are not limited to, flow cytometry, fluorescence activated cell sorting, antibody-dependent depletion, antibody-dependent solid phase capture, panning, affinity column separation and magnetic selection.

Chemotherapeutic agents useful in these methods are agent that targets cell surface molecules of cancer stem cells, e.g., a hematopoietic cancer stem cell. An exemplary agent is an antibody or fragment thereof and/or homolog thereof, such as a humanized or human antibody that binds specifically to a surface antigen of a cancer stem cell. In certain embodiments, the antigen is specific to a cancer stem cell, e.g., it is not present on the cell surface of cells that are differentiated from the cancer stem cell and/or it is not present on the surface of other types of cells. Exemplary antigens that are present on the cell surface of hematopoietic stem cells are further described herein. The following is a list of other antigens that may be present on the surface of cancer stem cells of B-cell malignancies: M34, antibodies, cancer antigens, CA15-3, carcinoembryonic antigen, CA125, cytokeratins, hMAM, MAGE, pancytokeratins, and HLA Class I or Class II antigens such as HLA-DR and HLA-D, MB, MT, MTe, Te, SB; CD5, CD6, CD10, CD19, CD20, CD21, CD22, CD23, CD24, CD25, CD26, CD28, CD30, CD32, CD35, CD37, CD38, CD39, CD40, CD43, CD45RO, CD45RA, CD45RB, CD49B, CD49C, CD49D, CD50, CD52, CD57, CD62L, CD69, CD70, CD72, CD73, CD74, CD75, CD77, CD79α,β, CD80, CD83, CDW84, CD86, CD89, CD97, CD98, CD119, CDW121B, CD122, CD124, CD125, CD126, CD127, CD130, CD132, CD135, CDW137, CD171, CD179A, CD179B, CD180, CD183, CDW197, CD200, CDW210, CD213A1 and CD213A2.

Examples of antigens that may be targeted for targeting cancer stem cells in T-cell malignancies include CD4, CD8, CD5, CD2, CD25, CD26, CD28, CD27, CD30, CD37, CD38, CD45RO, CD45RA, CD45RB, CD49A, CD49E, CD49F, CD50, CD52, CD56, CD57, CD62L, CD69, CD70, CD73, CD89, CD90, CD94, CD96, CD97, CD98, CD101, CD107A, CD107B, CD109, CD121A, CD122, CD124, CDW128, CD132, CD134, CDW137, CD148, CD152, CD153, CD154, CD160, CD161, CD165, CD166, CD171, CD178, CDW197, CDW210, CD212, CDW217, CD223, CD226, CD231, CD245 and CD247.

In certain embodiments of such methods, the cancer is a B cell malignancy, while in other embodiments the cancer is multiple myeloma. In certain embodiments of such methods, the cancer is Hodgkin's disease, while in other embodiments the cancer is non-Hodgkin's lymphoma. In certain embodiments of such methods, the cancer is not multiple myeloma. In certain embodiments of such methods, the cancer is not Hodgkin's disease, while in other embodiments the cancer is not non-Hodgkin's lymphoma.

In certain embodiments of such methods, the predetermined population of cells comprise one or more of the following markers: Hoechst (i.e. Hoechst Side Population), CD138$^-$, CD30$^-$, CD3$^-$, CD52$^+$, CD27$^+$, CD20$^+$, and CD19$^+$. While in other embodiments the predetermined population of cells comprise two or more of the following markers: Hoechst (i.e. Hoechst Side Population), CD138$^-$, CD30$^-$, CD3$^-$, CD52$^+$, CD27$^+$, CD20$^+$, and CD19$^+$. While in other embodiments the predetermined population of cells comprise three or more of the following markers: Hoechst (i.e. Hoechst Side Population), CD138$^-$, CD30$^-$, CD3$^-$, CD52$^+$, CD27$^+$, CD20$^+$, and CD19$^+$. While in other embodiments the predetermined population of cells comprise four or more of the following markers: Hoechst (i.e. Hoechst Side Population), CD138$^-$, CD30$^-$, CD3$^-$, CD52$^+$, CD27$^+$, CD20$^+$, and CD19$^+$. While in other embodiments the predetermined population of cells comprise five or more of the following markers: Hoechst (i.e. Hoechst Side Population), CD138$^-$, CD30$^-$, CD3$^-$, CD52$^+$, CD27$^+$, CD20$^+$, and CD19$^+$. While in other embodiments the predetermined population of cells are CD20$^+$. In certain embodiments of such methods, the predetermined population of cells are CD19$^+$, while in other embodiments the predetermined population of cells are CD27$^+$. In certain embodiments of such methods, the predetermined population of cells are Hoechst$^-$, while in other embodiments the isolated cells are ALDH$^+$. In certain embodiments of such methods, the predetermined population of cells are CD15$^-$, while in other embodiments the predetermined population of cells are CD30$^-$. In certain embodiments of such methods (e.g., in certain embodiments of leukemia), the predetermined population of cells are CD34$^+$. In other embodiments of such methods (e.g., in certain embodiments of multiple myeloma), the predetermined population of cells are CD34$^-$. In certain embodiments of such methods, the isolated cells are ALDH$^+$, while in other embodiments the isolated cells are CD138$^-$ or CD38$^-$.

In certain embodiments of such methods, the cancer is Hodgkin's Lymphoma (HL) and the cancer stem cells are CD138$^-$/CD19$^+$; CD138$^-$/CD20$^+$; CD138$^-$/CD27$^+$; CD138$^-$/CD15$^-$, CD138$^-$/CD52$^+$ and/or CD138$^-$/CD30$^-$. In certain embodiments of such methods, the cancer is Hodgkin's Lymphoma (HL) and the cancer stem cells are ALDH$^+$/CD138$^-$/CD19$^+$; ALDH$^+$/CD138$^-$/CD20$^+$;

ALDH$^+$/CD138$^-$/CD27$^+$; ALDH$^+$/CD138$^-$/CD15$^-$, ALDH$^+$/CD138$^-$/CD52$^+$ and/or ALDH$^+$/CD138$^-$/CD30$^-$. In some embodiments, the cancer is Hodgkin's Lymphoma and the cancer stem cells are CD19$^+$, CD20$^+$, CD27$^+$, CD15$^-$, CD52$^+$ and/or CD30$^-$.

In certain embodiments of such methods, the cancer is Multiple Myeloma and the cancer stem cells are CD138$^-$/CD27$^+$; CD138$^-$/CD34$^-$, CD138$^-$/CD19$^+$, CD138$^-$/CD52$^+$ and/or CD138$^-$/CD20$^+$. In certain embodiments of such methods, the cancer is Multiple Myeloma and the cancer stem cells are ALDH$^+$/CD138$^-$/CD27$^+$, ALDH$^+$/CD138$^-$/CD34$^-$, ALDH$^+$/CD138$^-$/CD52$^+$, ALDH$^+$/CD138$^-$/CD19$^+$, and/or ALDH$^+$/CD138$^-$/CD20$^+$. In some embodiments, the cancer is Multiple Myeloma and the cancer stem cells are CD138$^-$, CD27$^+$, CD19$^+$ and/or CD20$^+$.

In certain embodiments of such methods, the cancer is leukemia and the cancer stem cells are CD38$^-$/CD34$^+$ and/or CD38$^-$. In certain embodiments of such methods, the cancer is leukemia and the cancer stem cells are ALDH$^+$/CD38$^-$/CD34$^+$ and/or ALDH$^+$/CD38$^-$. In some embodiments, the cancer is leukemia and the cancer stem cells are ALDH$^+$/CD34$^+$, ALDH$^+$/CD38$^-$, CD34$^+$ or CD38$^-$.

In certain embodiments of such methods, the cancer is Non Hodgkin's Lymphoma and the cancer stem cells are CD138$^-$/CD19$^+$ and/or CD138$^-$/CD20$^+$. In certain embodiments of such methods, the cancer is Non Hodgkin's Lymphoma and the cancer stem cells are ALDH$^+$/CD138$^-$/CD19$^+$ and/or ALDH$^+$/CD138$^-$/CD20$^+$. In certain embodiments of such methods, the cancer is Non Hodgkin's Lymphoma and the cancer stem cells are ALDH$^+$/CD19$^+$ and/or ALDH$^+$/CD20$^+$.

In certain embodiments the sample is from the patient's blood, while certain embodiments the sample is from the patient's bone marrow.

In certain embodiments of such methods the chemotherapeutic is a cytotoxic agent, an antiproliferative, a targeting agent, a biologic agent, or combination thereof. In certain embodiments the targeting agent is a kinase inhibitor or cell cycle regulator. In certain embodiments the biologic agent is a cytokine, vaccine, viral agent or immunostimulant, while in other embodiments the immunostimulant is a BCG, hormone, monoclonal antibody or siRNA. In certain embodiments of such methods, the chemotherapeutic is an HDAC inhibitor.

In certain embodiments of such methods, the cancer treatment is a stem-cell targeted therapy, while in other embodiments the cancer treatment involves induction of terminal differentiation. In certain embodiments of such methods, the cancer treatment involves inhibition of telomerase, while in other embodiments the cancer treatment involves inhibition of developmental signaling pathways. In certain embodiments of such methods, the cancer treatment involves inhibition of intracellular signal transduction pathways, while in other embodiments the cancer treatment involves induction of active immunity to cellular antigens. In certain embodiments of such methods, the cancer treatment involves induction of passive immunity to cellular antigens. In certain embodiments of such methods the chemotherapeutic is a hedgehog inhibitor, while in other embodiments the chemotherapeutic is a telomerase inhibitor. In certain embodiments the chemotherapeutic is rituximab. In certain embodiments the chemotherapeutic is alemtuzumab.

In certain embodiments of such methods, a high expression level of ALDH in the isolated population predicts a therapeutic benefit for the administration of a chemotherapeutic, while in other embodiments of such methods, a high expression level of ALDH in the isolated population predicts no therapeutic benefit for the administration of a chemotherapeutic. In certain embodiments of such methods, a low expression level of ALDH in the isolated population predicts a therapeutic benefit for the administration of a chemotherapeutic, while in other embodiments of such methods, a low expression level of ALDH in the isolated population predicts no therapeutic benefit for the administration of a chemotherapeutic.

Treatment Methods for Decreasing Tumor Burden

Provided herein are methods for treating cancer in a subject, comprising administering to a subject in need thereof a therapeutically effective amount of a first agent that is cytostatic or cytotocxic to a cancer stem cell and a therapeutically effective amount of a second agent that decreases tumor burden. The first agent may be an agent that targets cell surface molecules of cancer stem cells, e.g., a hematopoietic cancer stem cell. An exemplary agent is an antibody or fragment thereof and/or homolog thereof, such as a humanized or human antibody that binds specifically to a surface antigen of a cancer stem cell. In certain embodiments of such treatment methods, the first agent is rituximab. In certain embodiments the chemotherapeutic is alemtuzumab.

In certain embodiments, the antigen is specific to a cancer stem cell, e.g., it is not present on the cell surface of cells that are differentiated from the cancer stem cell and/or it is not present on the surface of other types of cells. Exemplary antigens that are present on the cell surface of hematopoietic stem cells are further described herein. The following is a list of other antigens that may be present on the surface of cancer stem cells of B-cell malignancies: M34, antibodies, cancer antigens, CA15-3, carcinoembryonic antigen, CA125, cytokeratins, hMAM, MAGE, pancytokeratins, and HLA Class I or Class II antigens such as HLA-DR and HLA-D, MB, MT, MTe, Te, SB; CD5, CD6, CD10, CD19, CD20, CD21, CD22, CD23, CD24, CD25, CD26, CD28, CD30, CD32, CD35, CD37, CD38, CD39, CD40, CD43, CD45RO, CD45RA, CD45RB, CD49B, CD49C, CD49D, CD50, CD52, CD57, CD62L, CD69, CD70, CD72, CD73, CD74, CD75, CD77, CD79α,β, CD80, CD83, CDW84, CD86, CD89, CD97, CD98, CD119, CDW121B, CD122, CD124, CD125, CD126, CD127, CD130, CD132, CD135, CDW137, CD171, CD179A, CD179B, CD180, CD183, CDW197, CD200, CDW210, CD213A1 and CD213A2.

Examples of antigens that may be targeted for targeting cancer stem cells in T-cell malignancies include CD4, CD8, CD5, CD2, CD25, CD26, CD28, CD27, CD30, CD37, CD38, CD45RO, CD45RA, CD45RB, CD49A, CD49E, CD49F, CD50, CD52, CD56, CD57, CD62L, CD69, CD70, CD73, CD89, CD90, CD94, CD96, CD97, CD98, CD101, CD107A, CD107B, CD109, CD121A, CD122, CD124, CDW128, CD132, CD134, CDW137, CD148, CD152, CD153, CD154, CD160, CD161, CD165, CD166, CD171, CD178, CDW197, CDW210, CD212, CDW217, CD223, CD226, CD231, CD245 and CD247.

The second agent may be any agent that is known for reducing the tumor mass of a cancer, e.g., a B cell malignancy. Such treatment not only includes chemotherapy, but also radiation therapy and anti-angiogenic therapy among others.

In some embodiments, the cancer is a solid tumor. In certain embodiments, the cancer is a hematological cancer, such as a B-cell malignancy. In some embodiments, the hematological cancer, such as a B-cell malignancy, is a hematological cancer or B-cell malignancy, respectfully, with the proviso that the disease is not Hodgkin's lymphoma. In certain embodiments, e.g., in which a bone marrow cell is detected and/or isolated, a hematological cancer, such as a B-cell malignancy is a hematological cancer or B-cell malignancy, respectfully, with the proviso that the disease is not multiple myeloma.

In certain embodiments of such methods, the cancer is a B cell malignancy, while in other embodiments the cancer is multiple myeloma. In certain embodiments of such methods, the cancer is Hodgkin's disease, while in other embodiments the cancer is non-Hodgkin's lymphoma. In certain embodiments of such methods, the cancer is not multiple myeloma. In certain embodiments of such methods, the cancer is not Hodgkin's disease, while in other embodiments the cancer is not non-Hodgkin's lymphoma.

In certain embodiments of the present invention, the first agent that is cytostatic or cytotoxic to a cancer stem cell is an antibody. In other embodiments of the present invention, the first agent that is cytostatic or cytoxic to the cancer stem cell is a small molecule drug. In some embodiments, the chemotherapeutic is an anti-CD34 agent, an anti-CD19 agent, an anti-CD52 agent, an anti-CD20 agent, and/or an anti-CD27 agent.

In certain embodiments of such methods, the cancer stem cells are $CD34^-$ and $CD138^-$, while in other embodiments the cancer stem cells are $CD19^+$, $CD20^+$, $CD27^+$, CD15– and CD30–. In certain embodiments of such methods, the cancer stem cells are CD138–, $CD27^+$, $CD19^+$ and $CD20^+$, while in other embodiments the cancer stem cells are $CD19^+$ and $CD20^+$.

In some embodiments, the cancer cells that are CD138– have a different affinity towards a chemotherapeutic than the cancer cells that are $CD138^+$. In some embodiments, the chemotherapeutic is more effective against the CD138– cancer stem cells than the $CD138^+$ cancer cells. In some embodiments, the chemotherapeutic is less effective against the CD138– cancer stem cells than the $CD138^+$ cancer cells. In some embodiments, the difference in the effectiveness of the drug against the cancer stem cells and the normal cancer cells is, e.g., about 20%, 30%, 40%, 50%, 60%, 70% or greater than 80%.

In certain embodiments of such methods, the predetermined population of cells comprise one or more of the following markers: Hoechst (i.e. Hoechst Side Population), $CD138^-$, $CD30^-$, $CD3^-$, $CD52^+$, $CD27^+$, $CD20^+$, and $CD19^+$. While in other embodiments the predetermined population of cells comprise two or more of the following markers: Hoechst (i.e. Hoechst Side Population), $CD138^-$, $CD30^-$, $CD3^-$, $CD52^+$, $CD27^+$, $CD20^+$, and $CD19^+$. While in other embodiments the predetermined population of cells comprise three or more of the following markers: Hoechst (i.e. Hoechst Side Population), $CD138^-$, $CD30^-$, $CD3^-$, $CD52^+$, $CD27^+$, $CD20^+$, and $CD19^+$. While in other embodiments the predetermined population of cells comprise four or more of the following markers: Hoechst (i.e. Hoechst Side Population), $CD138^-$, $CD30^-$, $CD3^-$, $CD52^+$, $CD27^+$, $CD20^+$, and $CD19^+$. While in other embodiments the predetermined population of cells comprise five or more of the following markers: Hoechst (i.e. Hoechst Side Population), $CD138^-$, $CD30^-$, $CD3^-$, $CD52^+$, $CD27^+$, $CD20^+$, and $CD19^+$. While in other embodiments the predetermined population of cells are $CD20^+$. In certain embodiments of such methods, the predetermined population of cells are $CD19^+$, while in other embodiments the predetermined population of cells are $CD27^+$. In certain embodiments of such methods, the predetermined population of cells are Hoechst, while in other embodiments the isolated cells are $ALDH^+$. In certain embodiments of such methods, the predetermined population of cells are $CD15^-$, while in other embodiments the predetermined population of cells are $CD30^-$. In certain embodiments of such methods (e.g., in certain embodiments of leukemia), the predetermined population of cells are $CD34^+$. In other embodiments of such methods (e.g., in certain embodiments of multiple myeloma), the predetermined population of cells are $CD34^-$. In certain embodiments of such methods, the isolated cells are $ALDH^+$, while in other embodiments the isolated cells are $CD138^-$ or $CD38^-$.

In certain embodiments of such methods, the cancer is Hodgkin's Lymphoma (HL) and the cancer stem cells are $CD138^-/CD19$; $CD138^-/CD20^+$; $CD138^-/CD27^+$; $CD138^-/CD15^-$, $CD138^-/CD52^+$ and/or $CD138^-/CD30^-$. In certain embodiments of such methods, the cancer is Hodgkin's Lymphoma (HL) and the cancer stem cells are $ALDH^+/CD138^-/CD19^+$; $ALDH^+/CD138^-/CD20^+$; $ALDH^+/CD138^-/CD27^+$; $ALDH^+/CD138^-/CD15^-$, $ALDH^+/CD138^-/CD52^+$ and/or $ALDH^+/CD138^-/CD30^-$. In some embodiments, the cancer is Hodgkin's Lymphoma and the cancer stem cells are $CD19^+$, $CD20^+$, $CD27^+$, $CD15^-$, $CD52^+$ and/or $CD30^-$.

In certain embodiments of such methods, the cancer is Multiple Myeloma and the cancer stem cells are $CD138^-/CD27^+$; $CD138^-/CD34^-$, $CD138^-/CD19^+$, $CD138^-/CD52^+$ and/or $CD138^-/CD20^+$. In certain embodiments of such methods, the cancer is Multiple Myeloma and the cancer stem cells are $ALDH^+/CD138^-/CD27^+$, $ALDH^+/CD138^-/CD34^-$, $ALDH^+/CD138^-/CD52^+$, $ALDH^+/CD138^-/CD19^+$, and/or $ALDH^+/CD138^-/CD20^+$. In some embodiments, the cancer is Multiple Myeloma and the cancer stem cells are $CD138^-$, $CD27^+$, $CD19^+$ and/or $CD20^+$.

In certain embodiments of such methods, the cancer is leukemia and the cancer stem cells are $CD38^-/CD34^+$ and/or $CD38^-$. In certain embodiments of such methods, the cancer is leukemia and the cancer stem cells are $ALDH^+/CD38^-/CD34^+$ and/or $ALDH^+/CD38^-$. In some embodiments, the cancer is leukemia and the cancer stem cells are $ALDH^+/CD34^+$, $ALDH^+/CD38^-$, $CD34^+$ or $CD38^-$.

In certain embodiments of such methods, the cancer is Non Hodgkin's Lymphoma and the cancer stem cells are $CD138^-/CD19^+$ and/or $CD138^-/CD20^+$. In certain embodiments of such methods, the cancer is Non Hodgkin's Lymphoma and the cancer stem cells are $ALDH^+/CD138^-/CD19^+$ and/or $ALDH^+/CD138^-/CD20^+$. In certain embodiments of such methods, the cancer is Non Hodgkin's Lymphoma and the cancer stem cells are $ALDH^+/CD19^+$ and/or $ALDH^+/CD20^+$.

In certain embodiments the sample is from the patient's blood, while certain embodiments the sample is from the patient's bone marrow.

In certain embodiments of such methods, a high expression level of ALDH in the isolated population indicates the test agent is effective, while in other embodiments of such methods, a high expression level of ALDH in the isolated population predicts indicates the test agent is not effective. In certain embodiments of such methods, a low expression level of ALDH in the isolated population indicates the test agent is effective, while in other embodiments of such methods, a low expression level of ALDH in the isolated population predicts indicates the test agent is not effective.

Identifying Cytostatic or Cytotoxic Agents

The methods for isolating and identifying circulating undifferentiated cells, including circulating cancer stem cells, disclosed herein can be used in a method to identify an agent that is cytostatic or cytotoxic toward a cancer stem cell. Such methods include the steps of isolating a circulating cancer stem cell and optionally determining the ALDH expression level of such cancer stem cells, identifying the cancer; and contacting the isolated cancer stem cell with a test agent and determine whether the test agent inhibits the proliferation of or is toxic to the cancer stem cell. The expression level of ALDH is used to evaluate the effect of the test agent. In certain embodiments, cells with high ALDH ($ALDH^{high}$) expression levels are used to evaluate the effect of the test agent. In such methods, the isolating and identifying of the circulating cancer stem cells involves first obtaining a sample from a patient (e.g., a blood sample and/or a bone marrow sample); then isolating a predetermined population of cells from the blood sample using at least one of the separation methods described herein. Such separation methods include, but are not limited to, flow cytometry, fluorescence activated cell sorting, antibody-dependent depletion, antibody-dependent solid phase capture, panning, affinity column separation and magnetic selection.

In certain embodiments of such methods, the cancer is a B cell malignancy, while in other embodiments the cancer is multiple myeloma. In certain embodiments of such methods, the cancer is Hodgkin's disease, while in other embodiments the cancer is non-Hodgkin's lymphoma. In certain embodiments of such methods, the cancer is not multiple myeloma. In certain embodiments of such methods, the cancer is not Hodgkin's disease, while in other embodiments the cancer is not non-Hodgkin's lymphoma.

In certain embodiments, the cancer is a hematological cancer, such as a B-cell malignancy. In some embodiments, the hematological cancer, such as a B-cell malignancy, is a hematological cancer or B-cell malignancy, respectfully, with the proviso that the disease is not Hodgkin's lymphoma. In certain embodiments, e.g., in which a bone marrow cell is detected and/or isolated, a hematological cancer, such as a B-cell malignancy is a hematological cancer or B-cell malignancy, respectfully, with the proviso that the disease is not multiple myeloma.

In certain embodiments of such methods, the cancer stem cells are $CD34^-$ and $CD138^-$, while in other embodiments the isolated cancer stem cells are $CD19^+$, $CD20^+$, $CD27^+$, $CD15-$ and $CD30-$. In certain embodiments of such methods, the stem cells are $CD138-$, $CD27^+$, $CD19^+$ and $CD20^+$, while in other embodiments the cancer stem cells are $CD19^+$ and $CD20^+$.

In certain embodiments of such methods, the predetermined population of cells comprise one or more of the following markers: Hoechst (i.e. Hoechst Side Population), $CD138^-$, $CD30^-$, $CD3^-$, $CD52^+$, $CD27^+$, $CD20^+$, and $CD19^+$. While in other embodiments the predetermined population of cells comprise two or more of the following markers: Hoechst (i.e. Hoechst Side Population), $CD138^-$, $CD30^-$, $CD3^-$, $CD52^+$, $CD27^+$, $CD20^+$, and $CD19^+$. While in other embodiments the predetermined population of cells comprise three or more of the following markers: Hoechst (i.e. Hoechst Side Population), $CD138^-$, $CD30^-$, $CD3^-$, $CD52^+$, $CD27^+$, $CD20^+$, and $CD19^+$. While in other embodiments the predetermined population of cells comprise four or more of the following markers: Hoechst (i.e. Hoechst Side Population), $CD138^-$, $CD30^-$, $CD3^-$, $CD52^+$, $CD27^+$, $CD20^+$, and $CD19^+$. While in other embodiments the predetermined population of cells comprise five or more of the following markers: Hoechst (i.e. Hoechst Side Population), $CD138^-$, $CD30^-$, $CD3^-$, $CD52^+$, $CD27^+$, $CD20^+$, and $CD19^+$. While in other embodiments the predetermined population of cells are $CD20^+$. In certain embodiments of such methods, the predetermined population of cells are $CD19^+$, while in other embodiments the predetermined population of cells are $CD27^+$. In certain embodiments of such methods, the predetermined population of cells are Hoechst, while in other embodiments the isolated cells are $ALDH^+$. In certain embodiments of such methods, the predetermined population of cells are $CD15^-$, while in other embodiments the predetermined population of cells are $CD30^-$. In certain embodiments of such methods (e.g., in certain embodiments of leukemia), the predetermined population of cells are $CD34^+$. In other embodiments of such methods (e.g., in certain embodiments of multiple myeloma), the predetermined population of cells are $CD34^-$. In certain embodiments of such methods, the isolated cells are $ALDH^+$, while in other embodiments the isolated cells are $CD138^-$ or $CD38^-$.

In certain embodiments of such methods, the cancer is Hodgkin's Lymphoma (HL) and the cancer stem cells are $CD138^-/CD19$; $CD138^-/CD20^+$; $CD138^-/CD27^+$; $CD138^-/CD15^-$, $CD138^-/CD52^+$ and/or $CD138^-/CD30^-$. In certain embodiments of such methods, the cancer is Hodgkin's Lymphoma (HL) and the cancer stem cells are $ALDH^+/CD138^-/CD19^+$; $ALDH^+/CD138^-/CD20^+$; $ALDH^+/CD138^-/CD27^+$; $ALDH^+/CD138^-/CD15^-$, $ALDH^+/CD138^-/CD52^+$ and/or $ALDH^+/CD138^-/CD30^-$. In some embodiments, the cancer is Hodgkin's Lymphoma and the cancer stem cells are $CD19^+$, $CD20^+$, $CD27^+$, $CD15^-$, $CD52^+$ and/or $CD30^-$.

In certain embodiments of such methods, the cancer is Multiple Myeloma and the cancer stem cells are $CD138^-/CD27^+$; $CD138^-/CD34^-$, $CD138^-/CD19^+$, $CD138^-/CD52^+$ and/or $CD138^-/CD20^+$. In certain embodiments of such methods, the cancer is Multiple Myeloma and the cancer stem cells are $ALDH^+/CD138^-/CD27^+$, $ALDH^+/CD138^-/CD34^-$, $ALDH^+/CD138^-/CD52^+$, $ALDH^+/CD138^-/CD19^+$, and/or $ALDH^+/CD138^-/CD20^+$. In some embodiments, the cancer is Multiple Myeloma and the cancer stem cells are $CD138^-$, $CD27^+$, $CD19^+$ and/or $CD20^+$.

In certain embodiments of such methods, the cancer is leukemia and the cancer stem cells are $CD38^-/CD34^+$ and/or $CD38^-$. In certain embodiments of such methods, the cancer is leukemia and the cancer stem cells are $ALDH^+/CD38^-/CD34^+$ and/or $ALDH^+/CD38^-$. In some embodiments, the cancer is leukemia and the cancer stem cells are $ALDH^+/CD34^+$, $ALDH^+/CD38^-$, $CD34^+$ or $CD38^-$.

In certain embodiments of such methods, the cancer is Non Hodgkin's Lymphoma and the cancer stem cells are $CD138^-/CD19^+$ and/or $CD138^-/CD20^+$. In certain embodiments of such methods, the cancer is Non Hodgkin's Lymphoma and the cancer stem cells are $ALDH^+/CD138^-/CD19^+$ and/or $ALDH^+/CD138^-/CD20^+$. In certain embodiments of such methods, the cancer is Non Hodgkin's Lymphoma and the cancer stem cells are $ALDH^+/CD19^+$ and/or $ALDH^+/CD20^+$.

In certain embodiments the sample is from the patient's blood, while certain embodiments the sample is from the patient's bone marrow.

In certain embodiments of such methods, a high expression level of ALDH in the isolated population indicates the test agent is effective, while in other embodiments of such methods, a high expression level of ALDH in the isolated population predicts indicates the test agent is not effective. In certain embodiments of such methods, a low expression level of ALDH in the isolated population indicates the test agent is effective, while in other embodiments of such methods, a low expression level of ALDH in the isolated population predicts indicates the test agent is not effective.

Kits

Provided herein are kits used to isolating and identifying undifferentiated cells, including circulating cancer stem cells. In certain embodiments, such kits include one or more reagents for detecting one or more of the following biomarkers ALDH activity, Hoechst side population, CD34, CD38, CD138, CD19, CD20, CD27, CD15, CD30, CD34 and CD52. In certain embodiments the cancer stem cells are circulating cancer stem cells, while in other embodiments the cancer stem cells are from bone marrow. In certain embodiments of such kits the biomarker comprises ALDH. In certain embodiments of such kits, the kit is for identifying leukemia and the biomarkers are ALDH, CD34 and CD38. In certain embodiments of such kits, the kit is for identifying Hodgkin's Lymphoma and the biomarkers are ALDH, CD19, CD20, CD27, CD15 and CD30. In certain embodiments of such kits, the kit is for identifying Multiple Myeloma and the biomarkers are ALDH, CD138, CD27, CD19 and CD20. In certain embodiments of such kits, the kit is for identifying Non Hodgkin's Lymphoma and the biomarkers are ALDH, CD19 and CD20.

In certain embodiments of such kits, the kits include reagents for isolating a predetermined population of cells from the blood sample. In certain embodiments, such reagents are for immunomagnetic separation of cells, while in other embodiments such reagents are for flow cytometric separation of cells. In certain embodiments, such are for fluorescence activated cell sorting (FACS), while in other embodiments such reagents are for affinity column separation.

Chemotherapeutics

The methods described herein include the monitoring the effectiveness of a cancer treatment. In these embodiments, the cancer treatment can include any cancer treatment including surgery (such as cutting, abrading, ablating (by physical or chemical means or a combination of physical or chemical means), suturing, lasering or otherwise physically changing body tissues and organs), radiation therapy, administration of chemotherapeutic agents and combinations of any two or all of these methods.

The methods described herein provide methods for determining the effectiveness of a chemotherapeutic agent towards a cancer.

The methods described herein provide methods for treating cancer in a patient by administering a cancer therapy. Again, in these embodiments, the cancer treatment can include any cancer treatment including surgery (such as cutting, abrading, ablating (by physical or chemical means or a combination of physical or chemical means), suturing, lasering or otherwise physically changing body tissues and organs), radiation therapy, administration of chemotherapeutic agents and combinations of any two or all of these methods. In some embodiments the cancer therapy is administration of a chemotherapeutic agent.

The methods described herein describe methods for selecting patients predicted to benefit from a cancer therapy. In these embodiments, the cancer treatment can include any cancer treatment including surgery (such as cutting, abrading, ablating (by physical or chemical means or a combination of physical or chemical means), suturing, lasering or otherwise physically changing body tissues and organs), radiation therapy, administration of chemotherapeutic agents and combinations of any two or all of these methods. In some embodiments, the cancer therapy is administration of a chemotherapeutic agent.

Chemotherapeutic agents useful in these methods are agent that targets cell surface molecules of cancer stem cells, e.g., a hematopoietic cancer stem cell. An exemplary agent is an antibody or fragment thereof and/or homolog thereof, such as a humanized or human antibody that binds specifically to a surface antigen of a cancer stem cell. In certain embodiments, the antigen is specific to a cancer stem cell, e.g., it is not present on the cell surface of cells that are differentiated from the cancer stem cell and/or it is not present on the surface of other types of cells. Exemplary antigens that are present on the cell surface of hematopoietic stem cells are further described herein. The following is a list of other antigens that may be present on the surface of cancer stem cells of B-cell malignancies: M34, antibodies, cancer antigens, CA15-3, carcinoembryonic antigen, CA125, cytokeratins, hMAM, MAGE, pancytokeratins, and HLA Class I or Class II antigens such as HLA-DR and HLA-D, MB, MT, MTe, Te, SB; CD5, CD6, CD10, CD19, CD20, CD21, CD22, CD23, CD24, CD25, CD26, CD28, CD30, CD32, CD35, CD37, CD38, CD39, CD40, CD43, CD45RO, CD45RA, CD45RB, CD49B, CD49C, CD49D, CD50, CD52, CD57, CD62L, CD69, CD70, CD72, CD73, CD74, CD75, CD77, CD79α,β, CD80, CD83, CDW84, CD86, CD89, CD97, CD98, CD119, CDW121B, CD122, CD124, CD125, CD126, CD127, CD130, CD132, CD135, CDW137, CD171, CD179A, CD179B, CD180, CD183, CDW197, CD200, CDW210, CD213A1 and CD213A2.

Examples of antigens that may be targeted for targeting cancer stem cells in T-cell malignancies include CD4, CD8, CD5, CD2, CD25, CD26, CD28, CD27, CD30, CD37, CD38, CD45RO, CD45RA, CD45RB, CD49A, CD49E, CD49F, CD50, CD52, CD56, CD57, CD62L, CD69, CD70, CD73, CD89, CD90, CD94, CD96, CD97, CD98, CD101, CD107A, CD107B, CD109, CD121A, CD122, CD124, CDW128, CD132, CD134, CDW137, CD148, CD152, CD153, CD154, CD160, CD161, CD165, CD166, CD171, CD178, CDW197, CDW210, CD212, CDW217, CD223, CD226, CD231, CD245 and CD247.

Other chemotherapeutic agents useful in and contemplated by the present invention include, but are not limited to, anti-cancer agents, alkylating agents, cytotoxic agents, antimetabolic agents, hormonal agents, plant-derived agents, and biologic agents. In specific embodiments, the chemotherapeutic agent is a retinoid (e.g., a selective RXR agonist) or a methyltransferase inhibitor. Selective RXR agonists include, by way of non-limiting example, docosahexanoic acid (DHA), phytanic acid, methoprene acid, LG100268 (LG268), LG100324, LGD1057, SR11203, SR11217, SR11234, SR11236, SR11246, AGN194204, 3-methyl TTNEB, and bexarotene. In specific embodiments, the selective RXR agonist is bexarotene. Methyltransferase inhibitors include, by way of non-limiting example, 5-azacytidine, 5-aza-2'-deoxycytidine (decitabine), 1-beta-D-arabinofuranosyl-5-aza-cytosine, dihydro-5-aza-cytidine and MG98. In specific embodiments, the methyltransferase inhibitor is 5-azacytidine.

Anti-tumor substances are selected from, by way of non-limiting example, mitotic inhibitors (e.g., vinblastine), alkylating agents (e.g., cis-platin, carboplatin and cyclophosphamide), anti-metabolites (5-fluorouracil, cytosine arabinside and hydroxyurea), one of the anti-metabolites disclosed in European Patent Application No. 239362 (e.g., N-(5-[N-(3, 4-dihydro-2-methyl-4-oxoquinazolin-6-ylmethyl)-N-methylamino]-2-thenoyl)-L-glutamic acid), growth factor inhibitors, cell cycle inhibitors, intercalating antibiotics (e.g, adriamycin and bleomycin), enzymes (e.g., interferon), anti-hormones (e.g., anti-estrogens such as Nolvadex™ (tamoxifen) or anti-androgens such as Casodex™ (4'-cyano-3-(4-fluorophenylsulphonyl)-2-hydroxy-2-methyl-3'-(trifluoromethyl)propionanilide)). As with any treatment regiment described herein, these chemotherapeutic agents are administered, in various embodiments, simultaneous, sequential or separate from either or both of the first and second agents.

Alkylating agents include, by way of non-limiting example, bischloroethylamines (nitrogen mustards, e.g. chlorambucil, cyclophosphamide, ifosfamide, mechlorethamine, melphalan, uracil mustard), aziridines (e.g. thiotepa), alkyl alkone sulfonates (e.g. busulfan), nitrosoureas (e.g. carmustine, lomustine, streptozocin), non-classic alkylating agents (altretamine, dacarbazine, and procarbazine), platinum compounds (carboplastin and cisplatin).

Cytotoxic agents include, by way of non-limiting example, anthracyclines (e.g. doxorubicin, daunorubicin, epirubicin, idarubicin and anthracenedione), mitomycin C, bleomycin, dactinomycin, plicatomycin.

Antimetabolic agents are a group of drugs that interfere with metabolic processes vital to the physiology and proliferation of cancer cells. Antimetabolic agents include, by way of non-limiting example, fluorouracil (5-FU), floxuridine (5-FUdR), methotrexate, leucovorin, hydroxyurea, thioguanine (6-TG), mercaptopurine (6-MP), cytarabine, pentostatin, fludarabine phosphate, cladribine (2-CDA), asparaginase, and gemcitabine.

Hormonal agents are a group of drug that regulate the growth and development of their target organs. Hormonal agents include sex steroids and their derivatives and analogs thereof, such as estrogens, androgens, and progestins. Hormonal agents include, by way of non-limiting example, synthetic estrogens (e.g. diethylstibestrol), antiestrogens (e.g. tamoxifen, toremifene, fluoxymesterol and raloxifene), anti-androgens (bicalutamide, nilutamide, flutamide), aromatase inhibitors (e.g., aminoglutethimide, anastrozole and tetrazole), ketoconazole, goserelin acetate, leuprolide, megestrol acetate and mifepristone.

Plant-derived agents include, by way of non-limiting example, vinca alkaloids (e.g., vincristine, vinblastine, vindesine, vinzolidine and vinorelbine), podophyllotoxins (e.g., etoposide (VP-16) and teniposide (VM-26)), taxanes (e.g., paclitaxel and docetaxel). These plant-derived agents generally act as antimitotic agents that bind to tubulin and inhibit mitosis.

As used herein, the phrase "biologic agents" refers to a group of biomolecules that elicit cancer/tumor regression when used alone or in combination with chemotherapy and/or radiotherapy. Biologic agents include, by way of non-limiting example, immuno-modulating proteins such as cytokines, monoclonal antibodies against tumor antigens, tumor suppressor genes, and cancer vaccines.

Furthermore, in various embodiments of the present invention, the additional therapeutic agent (or chemotherapeutic agent) is selected from, by way of non-limiting example, aromatase inhibitors, antiestrogen, anti-androgen, corticosteroids, gonadorelin agonists, topoisomerase 1 and 2 inhibitors, microtubule active agents, alkylating agents, nitrosoureas, antineoplastic antimetabolites, platinum containing compounds, lipid or protein kinase targeting agents, IMiDs, protein or lipid phosphatase targeting agents, anti-angiogenic agents, Akt inhibitors, IGF-I inhibitors, FGF3 modulators, mTOR inhibitors, Smac mimetics, other HDAC inhibitors, agents that induce cell differentiation, bradykinin 1 receptor antagonists, angiotensin II antagonists, cyclooxygenase inhibitors, heparanase inhibitors, lymphokine inhibitors, cytokine inhibitors, IKK inhibitors, P38MAPK inhibitors, HSP90 inhibitors, multlikinase inhibitors, bisphosphanates, rapamycin derivatives, anti-apoptotic pathway inhibitors, apoptotic pathway agonists, PPAR agonists, inhibitors of Ras isoforms, telomerase inhibitors, protease inhibitors, metalloproteinase inhibitors, aminopeptidase inhibitors, dacarbazine (DTIC), actinomycins $C_2$, $C_3$, D, and $F_1$, cyclophosphamide, melphalan, estramustine, maytansinol, rifamycin, streptovaricin, doxorubicin, daunorubicin, epirubicin, idarubicin, detorubicin, caminomycin, idarubicin, epirubicin, esorubicin, mitoxantrone, bleomycins A, $A_2$, and B, camptothecin, Irinotecan®, Topotecan®, 9-aminocamptothecin, 10,11-methylenedioxycamptothecin, 9-nitrocamptothecin, bortezomib, temozolomide, TAS103, NPI0052, combretastatin, combretastatin A-2, combretastatin A-4, calicheamicins, neocarcinostatins, epothilones A B, C, and semi-synthetic variants, Herceptin®, rituxibam, (RITUXAN™), alemtuzumab, CD40 antibodies, asparaginase, interleukins, interferons, leuprolide, and pegaspargase, 5-fluorouracil, fluorodeoxyuridine, ptorafur, 5'-deoxyfluorouridine, UFT, MITC, S-1 capecitabine, diethylstilbestrol, tamoxifen, toremefine, tolmudex, thymitaq, flutamide, fluoxymesterone, bicalutamide, finasteride, estradiol, trioxifene, dexamethasone, leuproelin acetate, estramustine, droloxifene, medroxyprogesterone, megesterol acetate, aminoglutethimide, testolactone, testosterone, diethylstilbestrol, hydroxyprogesterone, mitomycins A, B and C, porfiromycin, cisplatin, carboplatin, oxaliplatin, tetraplatin, platinum-DACH, ormaplatin, thalidomide, lenalidomide, CI-973, telomestatin, CHIR258, Rad 001, SAHA, Tubacin, 17-AAG, sorafenib, JM-216, podophyllotoxin, epipodophyllotoxin, etoposide, teniposide, Tarceva®, Iressa®, Imatinib®, Miltefosine®, Perifosine®, aminopterin, methotrexate, methopterin, dichloro-methotrexate, 6-mercaptopurine, thioguanine, azattuoprine, allopurinol, cladribine, fludarabine, pentostatin, 2-chloroadenosine, deoxycytidine, cytosine arabinoside, cytarabine, azacitidine, 5-azacytosine, gencitabine, 5-azacytosine-arabinoside, vincristine, vinblastine, vinorelbine, leurosine, leurosidine and vindesine, paclitaxel, taxotere and docetaxel.

In further embodiments, additional therapeutic agents include interleukins. Specific interleukins include, by way of non-limiting example, interleukin 2 (IL-2), interleukin 4 (IL-4), and interleukin 12 (IL-12).

Interferons include more than 23 related subtypes with overlapping activities, all of the IFN subtypes within the scope of the present invention. IFN has demonstrated activity against many solid and hematologic malignancies, the later appearing to be particularly sensitive.

Other cytokines included within the scope of the additional therapeutic agent are cytokines that exert profound effects on hematopoiesis and immune functions. Examples of such cytokines include, by way of non-limiting example, erythropoietin, granulocyte-CSF (filgrastin), and granulocyte, macrophage-CSF (sargramostim).

Other immuno-modulating agents include, by way of non-limiting example, bacillus Calmette-Guerin, levamisole, and octreotide, a long-acting octapeptide that mimics the effects of the naturally occurring hormone somatostatin.

Monoclonal antibodies against tumor antigens are antibodies elicited against antigens expressed by tumors, including tumor-specific antigens. Monoclonal antibodies of the present invention include, by way of non-limiting example, HERCEPTINT™

As used herein, tumor suppressor genes are genes that function to inhibit the cell growth and division cycles, thus preventing the development of neoplasia. Tumor suppressor genes include, by way of non-limiting example, DPC-4, NF-1, NF-2, RB, p53, WT1, BRCA1 and BRCA2.

Cancer vaccines are a group of agents that induce the body's specific immune response to tumors. Most of cancer vaccines under research and development and clinical trials are tumor-associated antigens (TAAs). TAA are structures (i.e. proteins, enzymes or carbohydrates) which are present on tumor cells and relatively absent or diminished on normal cells. By virtue of being fairly unique to the tumor cell, TAAs provide targets for the immune system to recognize and cause their destruction. TAAs include, by way of non-limiting example, gangliosides (GM2), prostate specific antigen (PSA), alpha-fetoprotein (AFP), carcinoembryonic antigen (CEA) (produced by colon cancers and other adenocarcinomas, e.g. breast, lung, gastric, and pancreas cancer s), melanoma associated antigens (MART-1, gp 100, MAGE 1,3 tyrosinase), papillomavirus E6 and E7 fragments, whole cells or portions/lysates of antologous tumor cells and allogeneic tumor cells.

In some embodiments, the additional therapeutic agent is a proteasome inhibitor. Proteasome inhibitors include, by way of non-limiting example, bortezomib (Velcade, PS-341), PR-171, NPI-0052 (salinosporamide A), MG-132, omuralide, lactacystin and NEOSH101. In a specific embodiment, the first and second agents are administered concurrently or sequentially (in either order) and the proteasome inhibitor is administered after both the first and second agents have been administered. In certain embodiments, the proteasome inhibitor is bortezomib.

In certain embodiments, an adjuvant is used in the combination to augment the immune response to TAAs. Examples of adjuvants include, by way of non-limiting example, bacillus Calmette-Guerin (BCG), endotoxin lipopolysaccharides, keyhole limpet hemocyanin (GKLH), interleukin-2 (IL-2), granulocyte-macrophage colony-stimulating factor (GM-CSF) and cytoxan.

In other embodiments of the present invention, the additional therapeutic agent is, by way of non-limiting example, betamethasone dipropionate (augmented and nonaugmented), betamethasone valerate, clobetasol propionate, prednisone, methyl prednisolone, diflorasone diacetate, halobetasol propionate, amcinonide, dexamethasone, dexosimethasone, fluocinolone acetononide, fluocinonide, halocinonide, clocortalone pivalate, dexosimetasone, flurandrenalide, salicylates, ibuprofen, ketoprofen, etodolac, diclofenac, meclofenamate sodium, naproxen, piroxicam, celecoxib, cyclobenzaprine, baclofen, cyclobenzaprine/lidocaine, baclofen/cyclobenzaprine, cyclobenzaprine/lidocaine/ketoprofen, lidocaine, lidocaine/deoxy-D-glucose, prilocalne, EMLA Cream (Eutectic Mixture of Local Anesthetics (lidocaine 2.5% and prilocalne 2.5%), guaifenesin, guaifenesin/ketoprofen/cyclobenzaprine, amitryptiline, doxepin, desipramine, imipramine, amoxapine, clomipramine, nortriptyline, protriptyline, duloxetine, mirtazepine, nisoxetine, maprotiline, reboxetine, fluoxetine, fluvoxamine, carbamazepine, felbamate, lamotrigine, topiramate, tiagabine, oxcarbazepine, carbamezipine, zonisamide, mexiletine, gabapentin/clonidine, gabapentin/carbamazepine, carbamazepine/cyclobenzaprine, antihypertensives including clonidine, codeine, loperamide, tramadol, morphine, fentanyl, oxycodone, hydrocodone, levorphanol, butorphanol, menthol, oil of wintergreen, camphor, eucalyptus oil, turpentine oil; CB1/CB2 ligands, acetaminophen, infliximab) nitric oxide synthase inhibitors, inhibitors of inducible nitric oxide synthase; capsaicin or combinations thereof.

HDAC Inhibitors as a Chemotherapeutic

In certain embodiments, the chemotherapeutic agent is an HDAC inhibitor. In some embodiments, the HDAC inhibitor may be a Class I selective HDAC inhibitor. In these embodiments, the HDAC inhibitor inhibits at least one of HDAC-1, HDAC-2, HDAC-3, HDAC-8, or HDAC-11. In a specific embodiment, the HDAC inhibitor inhibits HDAC-1. In other embodiments, the HDAC inhibitor inhibits HDAC-2. In yet another embodiment, the HDAC inhibitor inhibits HDAC-3. In other embodiments, the HDAC inhibitor inhibits HDAC-11. In other embodiments, the HDAC inhibitor inhibits HDAC-1, HDAC-2, HDAC-3 and HDAC-11. In other embodiments, the HDAC inhibitor is, by way of non-limiting example, MGCD-0103 (N-(2-amino-phenyl)-4-[(4-pyridin-3-yl-pyrimidin-2-ylamino)-methyl]-benzamide) and derivatives of MGCD-0103, MS-275 (N-(2-aminophenyl)-4-(N-(pyridin-3-ylmethoxycarbonyl)aminomethyl)benzamide and derivatives of MS-275 (see, e.g., U.S. Pat. No. 6,174,905, the contents of which is incorporated by reference herein in its entirety), SNDX-275), FK228 and derivatives of FK228, spiruchostatin A and derivatives of spiruchostatin A, SK7041 and derivatives of SK704, SK7068 and derivatives of SK7068 and 6-amino nicotinamides and derivatives of 6-amino nicotinamides. In a specific non-limiting example, the HDAC inhibitor is MS-275.

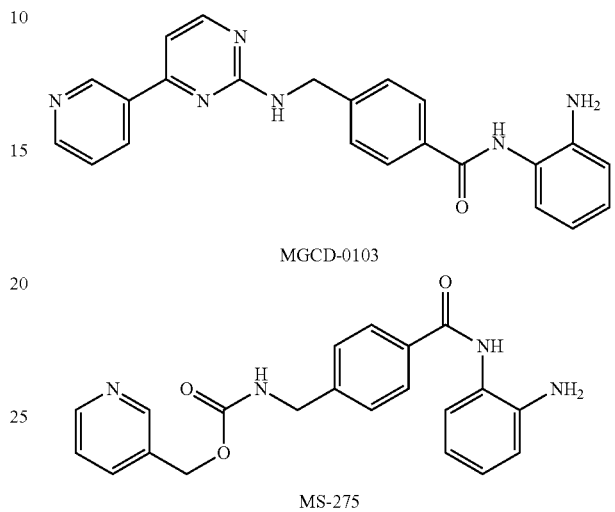

MGCD-0103

MS-275

In various embodiments, the HDAC inhibitor is a non-selective HDAC inhibitor. In these specific embodiments, the non-selective HDAC inhibitor is, by way of non-limiting example, N'-hydroxy-N-phenyl-octanediamide (suberoylanilide hydroxamic acid, SAHA), pyroxamide, CBHA, trichostatin A (TSA), trichostatin C, salicylihydroxamic acid (SBHA), azelaic bihydroxamic acid (ABHA), azelaic-1-hydroxamate-9-analide (AAHA), 6-(3-chlorophenylureido) carpoic hydroxamic acid (3Cl-UCHA), oxamflatin, A-161906, scriptaid, PXD-101, LAQ-824, CHAP, MW2796, LBH589 or MW2996, or derivatives of any of these compounds. In a specific embodiment, the HDAC inhibitor is SAHA.

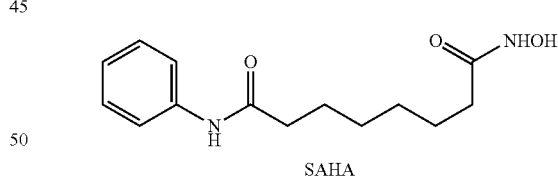

SAHA

In other embodiments, the HDAC inhibitor is selected from, by way of non-limiting example, hydroxamic acids, suberoylanilidine hydroxamic acid, TSA, TSC, m-carboxycinnamic acid bishydroxamide (CBHA), pyrozamide, salicylbishyudoxamic acid, suberoyl bishydroxamic acid (SBHA), azelaic bishydroxamic acid (ABHA), Azelaic-1-hydroxamate-9-anilide (AAHA), Oxamflatin, Scriptaid, CHAP, MW2996, MW2976, butanoic acid, valproic acid, 4-phenylbutanoic acid, N-acetyldinaline, CI-994 trapoxins, depeudecin, depsipeptide, FK 228, FR225497, Apicidin cyclic tetrapeptide, Apicidin Ia, Apicidin Ib, Apicidin Ic, Apicidin IIa, Apicidin IIb, sodium butyrate, isovalerate, valerate. 4-phenylbutyrate (4-PBA), phenylbutyrate (PB) propionate, butyaramide, isobutyramide, phylacetate, 3-bromopropionate, tributyrin, valproic acid, Valproate, Pivanex, Savicol, Baceca and LBH589, or derivatives of any of these compounds.

EXAMPLES

Example A

Multiple Myeloma (MM)

Patient Specimens, Cell Lines, and Cell Culture

Blood and bone marrow were obtained from 16 patients with active MM (8 newly diagnosed, 8 relapsed) granting informed consent as approved by the Johns Hopkins Medical Institutes Institutional Review Board. RPMI 8226 and NCI-H929 cell lines were obtained from American Type Tissue Collection (Manassas, Va.). Bone marrow mononuclear cells were isolated by density centrifugation and depleted of $CD138^+$ plasma cells and $CD34^+$ hematopoietic progenitors using anti-human CD34 and CD138 magnetic microbeads (Miltenyi Biotec, Auburn, Calif.). Secondary depletion of $CD138^-$ $CD34^-$ cells was performed using anti-human CD20, CD27, or CD3 microbeads. Peripheral blood B cells were isolated following density centrifugation using the B cell isolation kit (Miltenyi Biotec). For NOD/SCID mouse experiments, $CD27^+$ B cells were further isolated by positive magnetic selection with anti-human CD27 microbeads and two successive rounds of magnetic enrichment. Cell purity was assessed by flow cytometry and demonstrated less than 5% contamination by relevant antigen expressing cells.

Flow Cytometric Analyses

The following monoclonal antibodies were used: mouse anti-human CD138-PE, CD27-FITC, CD27-APC, CD19-APC, and either anti-human κ or λ Ig light chain-FITC or PE antibodies (BD Pharmingen). Following the addition of propidium iodide (PI, 2 μg/ml) to discriminate dead cells, cells were analyzed and/or sorted with a FACSAria, FACSVantage, or MoFlo fluorescent cell sorter as previously described. Post sorting analysis demonstrated >96% purity of cell populations with >98% cell viability.

For side population studies, RPMI 8226 and NCI-H929 cells ($10^6$/ml) were incubated with Hoechst 33342 (10 μg/ml, Invitrogen, Carlsbad, Calif.) for 60 minutes at 37° C. followed by staining for 30 minutes at 4° C. with anti CD138. Clinical B cell samples were stained with Hoechst 33342 (5 μg/ml) for 90 minutes at 37° C. followed by staining for 30 minutes at 4° C. with anti CD27 and anti Ig light chain antibodies. The concentration of Hoechst 33342 and incubations times were initially identified that provided the highest frequency of side population cells with the lowest cytotoxicity determined by PI staining. Side population cells were analyzed on a LSR flow cytometer equipped with 424/44 nm band pass and 670 nm long pass optical filters (Omega Optical, Brattleboro, Vt.). As a control, cells were incubated as above with the addition of 50 μM verapamil. Cells were stained for ALDH using the ALDEFLUOR® reagent (Stem Cell Technologies, Vancouver, BC) and CD138, CD27, or Ig light chains according to the manufacturer's instructions. Values are presented as mean fluorescence intensity (MFI) as previously described.

For cell cycle analysis, RPMI 8226 and NCI-H929 cells were fixed in 70% ethanol at 4° C. for 30 minutes then washed and labeled with anti-CD138-FITC antibodies for 30 minutes. Following removal of excess antibody, cells were incubated with RNAse (50 μg/ml) and PI (2.5 μg/ml) for 30 minutes at 4° C. followed by flow cytometry and DNA content analysis using the ModFit program (Verity, Topsham, Me.).

NOD/SCID Mice

The use of NOD/SCID mice was approved by the Johns Hopkins Medical Institutes Animal Care Committee. Six to 8-week old mice underwent pretreatment with 300 cGy irradiation (84 cGy/min using a $^{137}$Cs γ irradiator) 12-16 hours prior to dorsal tail vein injection. Mice were sacrificed when they exhibited symptoms including lethargy, anorexia, hind limb paralysis or, in the absence of symptoms, at 20-26 weeks. Bone marrow was harvested from the long bones and engraftment was determined by staining for human CD138, CD19 and either surface or cytoplasmic kappa or lambda Ig light chains. Cells were also stained for mouse CD4 and CD8 to ensure symptoms were not due to endogenous thymic lymphomas. For re-engraftment studies, $CD19^+CD27^+$ cells were isolated by FACS and injected into secondary recipients as above.

Immunoglobulin Gene Rearrangement Detection

DNA was extracted from plasma cells or isolated bone marrow aspirates using CD138 magnetic microbeads or engrafted NOD/SCID mouse bone marrow samples (1-100× $10^4$ cells) using the QIAamp micro DNA isolation kit (Qiagen, Valencia, Calif.). DNA aliquots were subjected to PCR using primers for the immunoglobulin heavy chain gene VDJ region (FR3a: 5'-ACACGGC(C/T)(G/C)TGTATTACT-GTG-3', VLJH: 5'-TGACCAGGGT(A/G/C/T)CCTTGGC-CCCAG-3') for 30-40 cycles. Distilled water or control DNA encoding a known monoclonal Ig heavy chain gene rearrangement were used as negative or positive controls respectively. PCR-amplified products were subjected to capillary electrophoresis on an ABI PRISM 3100 genetic analyzer and evaluated using the Genescan 2.1 software package (Applied Biosystems, Foster City, Calif.). For sequence analysis, PCR products were resolved on a 2% agarose gel and major products were isolated and ligated into the TOPO TA cloning vector (Invitrogen) followed by DNA sequence analysis.

Example B

Hodgkin's Lymphoma (HL)

Patient Specimens, Cell Lines, and Cell Culture

Blood, bone marrow, and lymph nodes were obtained from 5 patients with active HL granting informed consent as approved by the Johns Hopkins Medical Institutes Institutional Review Board. L428 and KM-H2 cell lines were obtained from American Type Tissue Collection (Manassas, Va.). Mononuclear cells were isolated by density centrifugation and B cells were isolated using the B cell isolation kit (Miltenyi Biotec). Hodgkins Reed-Sternberg cells were isolated using sequential magnetic enrichment using CD15 and CD30 magnetic microbeads (Miltenyi Biotec, Auburn, Calif.). Cell purity was assessed by flow cytometry and demonstrated less than 5% contamination by relevant antigen expressing cells.

Flow Cytometric Analyses

The following monoclonal antibodies were used: mouse anti-human CD138-PE, CD27-FITC, CD27-APC, CD19-APC, CD30-FITC, CD15PE and either anti-human κ or λ Ig light chain-FITC or PE antibodies (BD Pharmingen). Following the addition of propidium iodide (PI, 2 μg/ml) to discriminate dead cells, cells were analyzed and/or sorted with a FACSAria fluorescent cell sorter. Post sorting analysis demonstrated >96% purity of cell populations with >98% cell viability.

For side population studies, L428 and KM-H2 cells ($10^6$/ml) were incubated with Hoechst 33342 (10 µg/ml, Invitrogen, Carlsbad, Calif.) for 60 minutes at 37° C. followed by staining for 30 minutes at 4° C. with anti CD20. Clinical B cell samples were stained with Hoechst 33342 (5 µg/ml) for 90 minutes at 37° C. followed by staining for 30 minutes at 4° C. with anti CD27 and anti Ig light chain antibodies. The concentration of Hoechst 33342 and incubations times were initially identified that provided the highest frequency of side population cells with the lowest cytotoxicity determined by PI staining. Side population cells were analyzed on a LSR flow cytometer equipped with 424/44 nm band pass and 670 nm long pass optical filters (Omega Optical, Brattleboro, Vt.). As a control, cells were incubated as above with the addition of 50 µM verapamil. Cells were stained for ALDH using the ALDEFLUOR® reagent (Stem Cell Technologies, Vancouver, BC) and CD20, CD27, or Ig light chains according to the manufacturer's instructions.

Immunoglobulin Gene Rearrangement Detection

DNA was extracted from peripheral blood B cells isolated using CD20, CD19, CD27 and ALDH as well as Hodgkins Reed Sternberg cells isolated from lymph nodes using CD15 and CD30. DNA aliquots were subjected to PCR using primers for the immunoglobulin heavy chain gene VDJ region (FR3a: 5'-ACACGGC(C/T)(G/C)TGTATTACTGTG-3', VLJH: 5'-TGACCAGGGT(A/G/C/T)CCTTGGCCCAG-3') for 30-40 cycles. Distilled water or control DNA encoding a known monoclonal Ig heavy chain gene rearrangement were used as negative or positive controls respectively. PCR-amplified products were subjected to capillary electrophoresis on an ABI PRISM 3100 genetic analyzer and evaluated using the Genescan 2.1 software package (Applied Biosystems, Foster City, Calif.). For sequence analysis, PCR products were resolved on a 2% agarose gel and major products were isolated and ligated into the TOPO TA cloning vector (Invitrogen) followed by DNA sequence analysis.

Example C

Characterization of Clonogenic MM Cells

Many agents are active in multiple myeloma (MM), but the majority of patients relapse. This clinical pattern suggests most cancer cells are eliminated, but cells with the clonogenic potential to mediate tumor regrowth are relatively chemoresistant. Our previous data suggested that CD13S+ MM plasma cells cannot undergo long-term proliferation, but rather arise from clonogenic CD13Sneg B cells. We compared the relative sensitivity of these distinct cell types to clinical anti-myeloma agents and found that dexamethasone, lenadilomide, bortezomib and 4-hydroxycyclophosphamide inhibited CD13S+ MM plasma cells but had little effect on CD13Sneg precursors in vitro. We further characterized clonogenic MM cells and stained cell lines using the Hoechst side population and Aldefluor assays. Each assay identified CD138– ells suggesting that they possess high drug efflux capacity and intracellular drug detoxification activity. We also found that MM cells expressing the memory B cell markers CD20 and CD27 could give rise to clonogenic MM growth in vitro and engraft immunodeficient NOD/SCID mice during both primary and secondary transplantation. Furthermore, both the side population and Aldefluor assays were capable of identifying circulating clonotypic memory B cell populations within the peripheral blood of MM patients. Our results suggest that circulating clonotypic B cell populations represent MM stem cells. Furthermore, these cells resembled normal memory B cells and displayed cellular properties characteristic of normal stem cells.

MM Plasma Cells and Precursors Display Differential Drug Sensitivities

Figure 10:
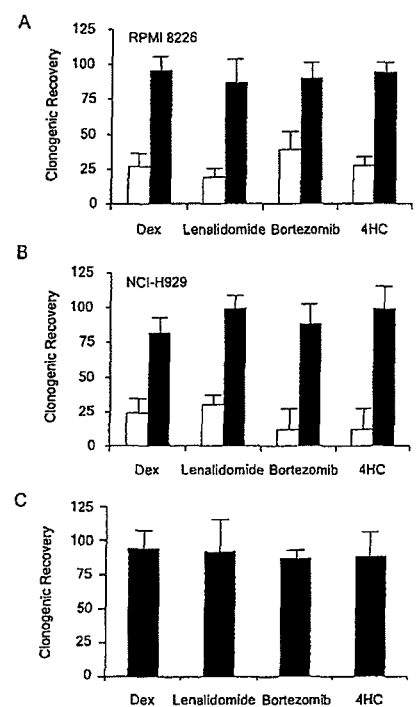
FIG. 10. MM cellular subsets display differential drug sensitivity. Clonogenic recovery of CD138+ (open bars) or CD138neg (black bars) cells from the MM cell lines (A) RPMI 8226 and (8) NCI-H929 or (C) CD138neg MM progenitors derived from 4 distinct clinical samples following treated with dexamethasone (Dex), lenalidomide, bortezomib or 4HC. Values represent the mean:t standard error of the mean (SEM) of 4 experiments.

We previously demonstrated that MM cells derived from primary clinical bone marrow specimens and capable of in vitro clonogenic growth lack expression of the characteristic plasma cell antigen CD138 (13, 18). Some MM cell lines appear to recapitulate the hierarchical cellular organization found within clinical specimens and contain small populations of CD138neg cells that express markers reminiscent of B cells and have relatively increased clonogenic growth potential in vitro compared to mature CD138+ plasma cells. To determine if MM precursors display relative drug resistance, CD138+ plasma cells and CD138neg progenitors were isolated from the RPMI 8226 and NCI-H929 mM cell lines and treated with 4 clinically active agents: the corticosteroid dexamethasone; the thalidomide analogue lenalidomide; the proteosome inhibitor bortezomib; or 4 hydroperoxycyclophosphamide (4HC) the active metabolite of the cytotoxic alkylator cyclophosphamide. Similar to their clinical activity, all 4 agents significantly inhibited the clonogenic growth of CD138+ plasma cells (FIGS. 10A and B; $P<0.02$ by student's t-test for all groups compared to the untreated control). In contrast, none of the 4 agents significantly inhibited the clonogenic growth of CD138neg progenitors from either cell line (FIGS. 10A and B; $P>0.1$). Although the lack of in vitro clonogenic growth limited our ability to study mature CD138+ plasma cells derived from primary clinical samples, we studied clonogenic MM precursors from 4 mM patients (2 newly diagnosed and 2 with relapsed disease) and found that they were not significantly affected by dexamethasone (mean 95%, range 77-125%), lenalidomide (mean 93%, range 71-143%), bortezomib (mean 89%, range 86-107%) or 4HC (mean 90%, range 81-105%; FIG. 10 C; $P>0.2$ for all groups compared to the untreated control). In addition, clonogenic precursors from newly diagnosed or relapsed patients were similarly resistant to each of these 4 agents.

MM Precursors Display Stem Cell Properties that Mediate Drug Resistance

Normal tissue-restricted adult stem cells are highly resistant to toxic injury that appears to be multi-factorial in nature. Furthermore, some of these processes serve as the basis for flow cytometric assays that can enrich for adult stem cells, and we examined whether these assays could distinguish cellular compartments in MM. The ATP binding cassette family of membrane transporters actively export xenobiotics thereby limiting the intracellular accumulation of these compounds. Furthermore, efflux of the DNA binding dye Hoechst 33342 by the ABCG2/BCRP transporter is required for detection of the "side population" phenotype that is characteristic of stem cells from many tissues. To examine whether the side population assay could identify clonogenic MM precursors we stained two human MM cell lines, RPMI 8226 and NCI-H929, with Hoechst 33342 and found that each contained small populations of side population cells (0.8-1.9% of total cells). Furthermore, co-staining for CD138 demonstrated that the side population cells were almost exclusively CD138– (97%) in comparison to the bulk of the population which was CD138$^+$.

Aldehyde dehydrogenase (ALDH), specifically ALDH1A1, mediates the biosynthesis of all-trans-retinoic acid as well as the detoxification of a variety of compounds such as ethanol and active metabolites of cyclophosphamide. Normal adult stem cells typically exhibit higher relative levels of ALDH activity than their differentiated progeny, and the fluorescently labelled ALDH substrate Aldefluor can isolate stem cells from a number of adult tissues. Staining of the RPMI 8226 and NCI-H929 cells revealed small populations of ALDH+ cells accounting for 3.7% and 4.3% of cells, respectively. Furthermore, co-staining cells for CD138 expression demonstrated that the CD138− cells had significantly higher levels of ALDH activity than CD138+ plasma cells.

Cellular quiescence is exhibited by most normal adult stem cells, and this property is thought to be a major mechanism of drug resistance. To determine whether MM precursors are relatively quiescent, immature CD138− cells or CD138+ plasma cells were isolated from the RPMI 8226 and NCI-H929 cell lines and stained with PI to evaluate their cell cycle status. Similar to normal adult stem cells, we found that nearly all 98%) of the CD138− cells in both cell lines were in G0/G1, compared to only 72% or 77% of the CD138 cells.

Clonogenic MM Cells Resemble Memory B Cells.

In human acute myeloid leukemia (AML) and brain tumors, cancer stem cells phenotypically resemble normal hematopoietic and neural stem cells. These findings suggest that human cancers may arise from normal cellular compartments capable of self-renewal. Unlike normal hematopoietic and neural stem cells with the ability to generate multiple cell types, B cells that give rise to plasma cells lack multi-lineage potential. However, in contrast to the hematopoietic and neural systems in which self-renewal is restricted to the most primitive cellular compartments, self-renewal is maintained during multiple stages of B cell development that permits the generation of clones producing the highest affinity antibodies as part of the adaptive immune response.

Clonogenic MM precursors resemble memory B cells in depleted primary bone marrow specimens of cells expressing the B cell surface antigen CD20 and the memory B cell surface marker CD27. Compared to the starting population of CD138− CD34− cells, depletion of CD20 or CD27 from the CD138− CD34− cell population significantly limited clonogenic MM growth (88% and 83%, respectively, FIG. 8A; P<0.001). In contrast, the removal of CD3 T cells did not have a significant effect on the clonogenic recovery of MM colonies (FIG. 8A; P>0.1). Thus, the phenotype of MM cells with in vitro clonogenic potential, CD138−CD20+CD27, parallels normal memory B cells.

Clonogenic Potential of MM Cells is Inhibited by Antibodies that Target CD20 and CD52

Rituximab and alemtuzumab, two humanized monoclonal antibodies that target the B-cell antigens CD20 and CD52, respectively, inhibit clonogenic MM cells. CD138− precursors or CD138+ plasma cells were isolated from the RPMI 8226 or NCI-H929 cell lines and treated with each of the two humanized monoclonal antibodies, rituximab or alemtuzumab, and in combination with human complement that strongly enhances their in vitro activity through complement dependent cytoxicity. Neither complement alone nor the monoclonal antibodies with or without complement affected the clonogenic growth of CD138+ plasma cells that lack the target antigens (FIG. 8B; P>0.3 for all groups compared to the untreated control). However, both antibodies significantly inhibited the clonogenic recovery of CD138− mM progenitors from both cell lines when combined with complement (FIG. 8B; P<0.01 for each combination compared to the complement alone or untreated control groups). Similarly, each combination of monoclonal B cell antibody and complement significantly inhibited the clonogenic recovery of CD138− mM progenitors isolated from 4 primary patient specimens (FIG. 8C; P<0.001).

Clonogenic MM Cells Arise from Memory B Cells.

Hypermutation without intraclonal variation suggesting that MM arises from a postgerminal center B cell. During the post-germinal stage of B cell development, selfrenewal is most evident in memory B cells and serves to maintain reactive B cell clones during repeated rounds of antigen exposure. Therefore, we hypothesized that clonogenic MM precursors resemble memory B cells and depleted primary bone marrow specimens of cells expressing the B cell surface antigen CD20 or the memory B cell surface marker CD27. Compared to the starting population of CD138− CD34− cells, the removal of either CD20+ or CD27+ cells significantly limited clonogenic MM growth by 88% and 83%, respectively. In contrast, the removal of CD3+ T cells did not have a significant effect on the clonogenic recovery of MM colonies. Thus, the phenotype of MM cells with in vitro clonogenic potential, CD138−CD20+CD27+, parallels normal memory B cells.

Circulating Clonotypic Memory B Cells from MM Patients Engraft NOD/SCID

B cells sharing Ig gene sequences and idiotype specificity with MM plasma cells have been detected in the blood and bone marrow of MM patients. We studied the functional growth capacity of these cells and injected CD19+CD27+ B cells isolated from the peripheral blood of 4 patients with MM into NOD/SCID mice. All recipient animals developed hind limb paralysis, along with detectable human CD138 plasma cells (6.6-15% of the total bone marrow cells) 4 to 6 months after injection. In contrast, no engraftment was detected following the injection of $1 \times 10^7$ of the corresponding CD138+ plasma cells isolated from each MM patient consistent with our previous studies. Furthermore, the human plasma cells were clonally related to the original MM plasma cells by Ig light chain expression, Ig heavy chain gene CDR3 length restriction and CDR3 DNA sequence. Small populations of Ig light chain-restricted CD19+CD27+ cells were also detected (0.01-0.06% of total bone marrow cells), and injection of these cells ($10.8-100 \times 10^3$ cells) into secondary recipients similarly produced MM engraftment after 4 to 6 months.

Clonotypic B Cells in MM Exhibit Stem Cell Properties

Since the side population and ALDH assays identified CD138− precursors within MM cell lines, we examined whether these assays could identify MM precursors in primary clinical specimens. We stained CD19+ B cells isolated from the peripheral blood of 4 mM patients with Hoechst 33342 and detected small numbers of side population cells (0.18-0.83% of total B cells). Further surface staining demonstrated that the majority (89-97%) of the side population B cells expressed CD27 and clonal surface Ig light chain restriction that matched each patient's MM plasma cells. In contrast, non-side population cells contained a mixture of CD27+ memory and CD27− naïve B cells expressing both Ig light chains (G1). We also stained these peripheral blood CD19+ B cells with Aldefluor and found small populations of ALDH+ cells. Similar to the side population B cells, most (86-93%) of the ALDH B+ cells expressed CD27 and clonotypic surface Ig light chain. In contrast, ALDH− cells contained a mixture of non-clonal CD27 positive and negative cells expressing both kappa and lambda Ig light chains.

Discussion

Highly clonogenic cell populations have been identified in several human cancers that are able to phenotypically recapitulate the original tumor in NOD/SCID mice. These cells can also be isolated from engrafted animals and retransplanted into secondary recipients; therefore, they have the capacity to produce differentiated progeny and undergo self-renewal, two defining characteristics of normal stem cells. We found that clonotypic cells isolated from MM patients and expressing normal memory B cell surface antigens were capable of producing MM in NOD/SCID mice upon primary and secondary transplantation. These results suggest that MM is organized in a hierarchical manner that parallels normal tissue development similar to AML and brain tumors in which cancer stem cells phenotypically resembling their normal counterparts give rise to differentiated progeny.

Others have similarly reported that clonotypic B cells from clinical specimens can generate disease in NOD/SCID mice. In contrast, Yaccoby et al. have reported that CD138+ MM plasma cells can be successfully xenografted into SCID mice implanted with human fetal bone fragments. However, engraftment of mature plasma cells in these SCID-hu mice may primarily reflect the ability of the human bone marrow to support implanted plasma cells and/or plasma blasts given the important role that the microenvironment plays in the survival of these cells. In a similar fashion, the bone fragments within SCID-hu mice have been found to support relatively mature AML blasts expressing the myeloid antigen CD33, whereas only CD34+ cells lacking markers of lineage commitment engraft NOD/SCID mice.

Although stem cells have been identified in an increasing number of human cancers, the clinical relevance and implications of these findings remain unclear. Standard response criteria used to measure the clinical efficacy of anti-cancer treatments primarily reflect changes in disease bulk and activity against mature tumor cells. Since cancer stem cells are a relatively low frequency population in most tumor types, the true inhibition of these cells is likely to be difficult to assess early following treatment, and a prolongation of disease remission would be required to establish such activity. The initial clinical responses induced by dexamethasone, lenalidomide, bortezomib and cyclophosphamide seen as decreased bone marrow plasmacytosis and monoclonal Ig levels in MM likely reflect the activity of these agents against mature MM plasma cells. However, the inability of dexamethasone or standard cytotoxic chemotherapy to produce sustained clinical remissions suggests that clonogenic cells responsible for tumor regrowth are insensitive to these agents and supports our data that MM stem cells are not inhibited by these drugs. It is unknown whether lenalidomide or bortezomib can produce durable remissions in MM since they have been only recently introduced for clinical use, but we found that clonogenic MM progenitors are similarly resistant to these agents. It is well known that the anti-tumor activity of these agents is mediated in part by modulating the interaction between myeloma plasma cells and bone marrow stromal cells. Therefore, it is possible that our in vitro studies failed to adequately assess the effects of these agents on the bone marrow microenvironment, but similar to other studies we found that clonogenic MM precursors could be isolated from the peripheral blood where these factors have little influence.

Our results complement a recent report describing the relative radioresistance of glioblastoma cancer stem cells compared to the differentiated cells that make up the bulk of the tumor mass. The stark biological differences between cancer stem cells and mature tumor cells is likely to be representative of many other malignancies as the clinical pattern of relapse following effective treatment can be seen in most human cancers. Therefore, therapeutic strategies that target the specific biology of cancer stem cells are likely required to prevent the continued production of mature tumor cells and produce sustained remissions. Monoclonal antibodies directed against B cell surface antigens limited MM progenitor clonogenic growth in vitro suggesting that specific biological properties exhibited by MM cancer stem cells may effectively serve as anti-tumor targets. Furthermore, we recently demonstrated that the developmental signalling pathway Hedgehog is up regulated in MM stem cells and regulates cell fate decisions. Therefore, optimal clinical strategies may require combining agents active against MM plasma cells to decrease tumor burden and alleviate symptoms with those that target MM cancer stem cells to prevent tumor regrowth and relapse.

The combined use of surface phenotype with flow cytometric based functional stem cell properties facilitates the identification of these cells within the circulation of MM patients. Therefore, it is possible that these methods may allow the quantification of these cells to be used as a surrogate marker for clinical response during cancer stem cell directed therapies. These results also suggest that inherent properties that distinguish normal adult stem cells from their differentiated progeny, such as quiescence and high expression of ABC transporters and intracellular detoxifying enzymes, contribute to their relative resistance to toxic injury. The precise mechanisms responsible for the resistance of clonogenic MM cells to dexamethasone, 4HC, lena lid om ide, and bortezomib are unknown, but resistance to individual drugs usually occurs through multiple cellular processes (45). Our data suggest that these same stem cell properties contribute to the drug resistance of MM cancer stem cells allowing them to persist and mediate disease relapse in MM patients initially responding to therapy.

What is claimed is:

1. A method for monitoring the effectiveness of a cancer treatment in a patient, wherein the cancer treatment is for leukemia, comprising the steps of:
   (a) obtaining a blood sample from the patient;
   (b) isolating a predetermined population of cells from the blood sample, wherein the isolated cells are CD34+ and CD38−, using at least one of flow cytometry, fluorescence activated cell sorting, antibody-dependent depletion, antibody-dependent solid phase capture, panning, affinity column separation, and magnetic selection;
   (c) determining whether the isolated cells are ALDH+; and
   (d) comparing the number of ALDH+ cells with the number of ALDH+ cells determined at an earlier time in the cancer treatment.

2. A method for monitoring the effectiveness of a cancer treatment in a patient, wherein the cancer treatment is for multiple myeloma, comprising the steps of:
   (a) obtaining a blood sample from the patient;
   (b) isolating a predetermined population of cells from the blood sample, wherein the isolated cells are CD138−, CD27+, CD19+ and CD20+, using at least one of flow cytometry, fluorescence activated cell sorting, antibody-dependent depletion, antibody-dependent solid phase capture, panning, affinity column separation, and magnetic selection;
   (c) determining whether the isolated cells are ALDH+; and
   (d) comparing the number of ALDH+ cells with the number of ALDH+ cells determined at an earlier time in the cancer treatment.

3. The method of claim 2, wherein the isolated cells are also CD52+.

4. The method of claim 2, wherein the isolated cells are also CD34−.

5. A method for monitoring the effectiveness of a cancer treatment in a patient, wherein the cancer treatment is for Non-Hodgkin's lymphoma, comprising the steps of:
   (a) obtaining a blood sample from the patient;
   (b) isolating a predetermined population of cells from the blood sample, wherein the isolated cells are CD19+ and CD20+, using at least one of flow cytometry, fluorescence activated cell sorting, antibody-dependent depletion, antibody-dependent solid phase capture, panning, affinity column separation, and magnetic selection;
(c) determining whether the isolated cells are ALDH; and
(d) comparing the number of ALDH$^+$ cells with the number of ALDH$^+$ cells determined at an earlier time in the cancer treatment.

6. The method of any one of claims 1-5, wherein the cancer treatment is a stem-cell targeted therapy, induction of terminal differentiation, inhibition of telomerase, inhibition of developmental signaling pathways, inhibition of intracellular signal transduction pathways, induction of active immunity to cellular antigens, induction of passive immunity to cellular antigens, a hedgehog inhibitor, a cytotoxic agent, an antiproliferative agent, a targeting agent, a biologic agent, rituximab, alemtuzumab, or an HDAC inhibitor.

7. The method of claim 6, wherein the targeting agent is a kinase inhibitor or a cell cycle regulator.

8. The method of claim 6, wherein the biologic agent is a cytokine, vaccine, viral agent, or immunostimulant.

* * * * *